(12) United States Patent
Wang et al.

(10) Patent No.: US 11,401,329 B2
(45) Date of Patent: Aug. 2, 2022

(54) ANTI-CD47 ANTIBODIES AND USES THEREOF

(71) Applicant: Phanes Therapeutics, Inc., San Diego, CA (US)

(72) Inventors: Minghan Wang, San Diego, CA (US); Hui Zou, Dallas, TX (US); Joshua Oaks, San Diego, CA (US); Haiqun Jia, San Diego, CA (US)

(73) Assignee: Phanes Therapeutics, Inc., San Diego, CA (US)

( * ) Notice: Subject to any disclaimer, the term of this patent is extended or adjusted under 35 U.S.C. 154(b) by 122 days.

(21) Appl. No.: 16/633,730

(22) PCT Filed: Jul. 30, 2018

(86) PCT No.: PCT/US2018/044384
§ 371 (c)(1),
(2) Date: Jan. 24, 2020

(87) PCT Pub. No.: WO2019/027903
PCT Pub. Date: Feb. 7, 2019

(65) Prior Publication Data
US 2020/0207853 A1 Jul. 2, 2020

Related U.S. Application Data

(60) Provisional application No. 62/657,094, filed on Apr. 13, 2018, provisional application No. 62/540,118, filed on Aug. 2, 2017.

(51) Int. Cl.
*C07K 16/28* (2006.01)

(52) U.S. Cl.
CPC ...... *C07K 16/2803* (2013.01); *C07K 2317/21* (2013.01); *C07K 2317/24* (2013.01); *C07K 2317/31* (2013.01); *C07K 2317/565* (2013.01); *C07K 2317/73* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 6,180,370 B1 * | 1/2001 | Queen | A61P 31/12 435/69.6 |
| 11,059,910 B2 * | 7/2021 | Masternak | C07K 16/461 |
| 2003/0026803 A1 | 2/2003 | Barclay et al. | |
| 2004/0147731 A1 | 7/2004 | Parkos et al. | |
| 2006/0135749 A1 | 6/2006 | Matozaki et al. | |
| 2007/0113297 A1 | 5/2007 | Yang et al. | |
| 2007/0148201 A1 | 6/2007 | Skerra et al. | |
| 2008/0107654 A1 | 5/2008 | Kikuchi et al. | |
| 2008/0131431 A1 | 6/2008 | Smith et al. | |
| 2009/0162381 A1 | 6/2009 | Freyberg et al. | |
| 2009/0191202 A1 | 7/2009 | Jamieson et al. | |
| 2010/0239578 A1 | 9/2010 | Danska et al. | |
| 2010/0239579 A1 | 9/2010 | Smith et al. | |
| 2011/0014119 A1 | 1/2011 | Jaiswal et al. | |
| 2011/0038870 A1 | 2/2011 | Van Den Berg et al. | |
| 2011/0206696 A1 | 8/2011 | Frazier et al. | |
| 2011/0237498 A1 | 9/2011 | Raymond et al. | |
| 2012/0156724 A1 | 6/2012 | Kikuchi et al. | |
| 2012/0189625 A1 | 7/2012 | Wang et al. | |
| 2012/0282174 A1 | 11/2012 | Weissman et al. | |
| 2012/0282277 A1 | 11/2012 | Freyberg et al. | |
| 2012/0295956 A1 | 11/2012 | Isenberg et al. | |
| 2012/0295957 A1 | 11/2012 | Isenberg et al. | |
| 2013/0011401 A1 | 1/2013 | Huber et al. | |
| 2013/0142786 A1 | 6/2013 | Liu et al. | |
| 2013/0189253 A1 | 7/2013 | Danska et al. | |
| 2013/0224188 A1 | 8/2013 | Eckelman et al. | |
| 2014/0065169 A1 | 3/2014 | Jaiswal et al. | |
| 2014/0127269 A1 | 5/2014 | Masli et al. | |
| 2014/0140989 A1 | 5/2014 | Eckelman et al. | |
| 2014/0161799 A1 | 6/2014 | Frazier et al. | |
| 2014/0161805 A1 | 6/2014 | Jamieson | |
| 2014/0161825 A1 | 6/2014 | Jaiswal et al. | |
| 2014/0193408 A1 | 7/2014 | Huber et al. | |
| 2014/0199308 A1 | 7/2014 | Van Den Berg et al. | |
| 2014/0271683 A1 | 9/2014 | Chao et al. | |
| 2014/0296477 A1 | 10/2014 | Dedieu et al. | |
| 2014/0303354 A1 | 10/2014 | Masternak et al. | |
| 2014/0369924 A1 | 12/2014 | Weissman et al. | |
| 2015/0017130 A1 | 1/2015 | Yang et al. | |
| 2015/0183874 A1 | 7/2015 | Liu et al. | |
| 2015/0238604 A1 | 8/2015 | Eckelman et al. | |
| 2015/0266942 A1 | 9/2015 | Tian et al. | |
| 2015/0274826 A1 | 10/2015 | Frazier et al. | |
| 2015/0353642 A1 | 12/2015 | Tykocinski et al. | |
| 2015/0376288 A1 | 12/2015 | Weiskopf et al. | |

(Continued)

FOREIGN PATENT DOCUMENTS

| | | | | |
|---|---|---|---|---|
| CA | 2972604 A1 | * | 7/2016 | ............ A61K 45/06 |
| WO | 1997027873 A1 | | 8/1997 | |
| WO | 2001048020 A1 | | 7/2001 | |
| WO | 2005019254 A1 | | 3/2005 | |
| WO | 2007033221 A2 | | 3/2007 | |

(Continued)

OTHER PUBLICATIONS

Rudikoff, S et al. Proceedings of the National Academy of Sciences of the United States of America vol. 79,6 (1982): 1979-83 (Year: 1982).*

(Continued)

*Primary Examiner* — Michael Szperka
*Assistant Examiner* — Lia E Taylor
(74) *Attorney, Agent, or Firm* — Ice Miller LLP

(57) ABSTRACT

Anti-CD47 antibodies and antigen-binding fragments thereof are described. Also described are nucleic acids encoding the antibodies, compositions comprising the antibodies, and methods of producing the antibodies and using the antibodies for treating or preventing diseases such as cancer, inflammatory disease, infectious disease, atherosclerosis, cardiovascular disease, metabolic disease, radiation-induced injury, and/or autoimmune disease.

17 Claims, 18 Drawing Sheets

Specification includes a Sequence Listing.

(56) References Cited

U.S. PATENT DOCUMENTS

| | | |
|---|---|---|
| 2016/0008429 A1 | 1/2016 | Willingham et al. |
| 2016/0009814 A1 | 1/2016 | Jaiswal et al. |
| 2016/0009815 A1 | 1/2016 | Jaiswal et al. |
| 2016/0069898 A1 | 3/2016 | Weiskopf et al. |
| 2016/0137733 A1 | 5/2016 | Frazier et al. |
| 2016/0137734 A1 | 5/2016 | Frazier et al. |
| 2016/0144009 A1 | 5/2016 | Tseng et al. |
| 2016/0157470 A1 | 6/2016 | Gurer et al. |
| 2016/0176976 A1 | 6/2016 | Jaiswal et al. |
| 2016/0176978 A1 | 6/2016 | Jaiswal et al. |
| 2016/0177276 A1 | 6/2016 | Lo et al. |
| 2016/0319256 A9 | 6/2016 | Deming et al. |
| 2016/0194406 A1 | 7/2016 | Leeper et al. |
| 2016/0251435 A1 | 9/2016 | Eckelman et al. |
| 2016/0257751 A1 | 9/2016 | Swanson et al. |
| 2016/0289326 A1 | 10/2016 | Chao et al. |
| 2016/0304609 A1 | 10/2016 | Liu et al. |
| 2016/0333093 A1 | 11/2016 | Weiskopf et al. |
| 2016/0345549 A1 | 12/2016 | Gurer et al. |
| 2017/0029524 A1 | 2/2017 | Liu et al. |
| 2017/0073414 A1 | 3/2017 | Weiskopf et al. |
| 2017/0369572 A1 | 12/2017 | Sato et al. |
| 2018/0051081 A1 | 2/2018 | Frazier et al. |
| 2018/0057592 A1 | 3/2018 | Frazier et al. |
| 2018/0127480 A1 | 5/2018 | Ho et al. |
| 2018/0148512 A1 | 5/2018 | Tykocinski et al. |

FOREIGN PATENT DOCUMENTS

| | | | |
|---|---|---|---|
| WO | 2007133811 A2 | 11/2007 | |
| WO | 2008060785 A2 | 5/2008 | |
| WO | 2009046541 A1 | 4/2009 | |
| WO | 2009091601 A1 | 7/2009 | |
| WO | 2009131453 A1 | 10/2009 | |
| WO | 2010070047 A1 | 6/2010 | |
| WO | 2010083253 A2 | 7/2010 | |
| WO | 2010130053 A1 | 11/2010 | |
| WO | 2011034969 A1 | 3/2011 | |
| WO | 2011042548 A1 | 4/2011 | |
| WO | 2011076781 A1 | 6/2011 | |
| WO | 2011143624 A2 | 11/2011 | |
| WO | 2012031273 A2 | 3/2012 | |
| WO | 2012088309 A1 | 6/2012 | |
| WO | 2012172521 A1 | 12/2012 | |
| WO | 2013104918 A2 | 7/2013 | |
| WO | 2013109752 A1 | 7/2013 | |
| WO | 2013119714 A1 | 8/2013 | |
| WO | 2014078373 A1 | 5/2014 | |
| WO | 2014087248 A2 | 6/2014 | |
| WO | 2014093678 A2 | 6/2014 | |
| WO | 2014094122 A1 | 6/2014 | |
| WO | 2014121093 A1 | 8/2014 | |
| WO | 2014123580 A1 | 8/2014 | |
| WO | 2014124028 A1 | 8/2014 | |
| WO | 2014149477 A1 | 9/2014 | |
| WO | 2014179132 A1 | 11/2014 | |
| WO | 2014186761 A2 | 11/2014 | |
| WO | 2015041987 A1 | 3/2015 | |
| WO | 2015105995 A2 | 7/2015 | |
| WO | 2015138600 A2 | 9/2015 | |
| WO | 2015148416 A1 | 10/2015 | |
| WO | 2015191861 A1 | 12/2015 | |
| WO | 2016023001 A1 | 2/2016 | |
| WO | 2016023040 A1 | 2/2016 | |
| WO | 2016024021 A1 | 2/2016 | |
| WO | 2016033201 A1 | 3/2016 | |
| WO | 2016044021 A1 | 3/2016 | |
| WO | 2016063233 A1 | 4/2016 | |
| WO | 2016065329 A1 | 4/2016 | |
| WO | 2016081423 A1 | 6/2016 | |
| WO | 2016089692 A1 | 6/2016 | |
| WO | 2016109415 A1 | 7/2016 | |
| WO | 2016118754 A1 | 7/2016 | |
| WO | WO-2016109415 A1 * | 7/2016 | ....... A61K 39/39541 |
| WO | 2016138306 A1 | 9/2016 | |
| WO | 2016141328 A2 | 9/2016 | |
| WO | 2016141357 A1 | 9/2016 | |
| WO | 2016179399 A1 | 11/2016 | |
| WO | 2016187226 A1 | 11/2016 | |
| WO | 2017049251 A2 | 3/2017 | |
| WO | 2017053423 A1 | 3/2017 | |
| WO | 2017121771 A1 | 7/2017 | |
| WO | 2017165464 A1 | 9/2017 | |
| WO | 2017178653 A2 | 10/2017 | |
| WO | 2018009499 A1 | 1/2018 | |
| WO | 2018014067 A1 | 1/2018 | |
| WO | 2018057669 A1 | 3/2018 | |
| WO | 2018075857 A1 | 4/2018 | |
| WO | 2018075960 A1 | 4/2018 | |
| WO | 2018081897 A1 | 5/2018 | |
| WO | 2018081898 A1 | 5/2018 | |
| WO | 2018089508 A2 | 5/2018 | |
| WO | 2018107058 A1 | 6/2018 | |

OTHER PUBLICATIONS

Sela-Culang et al. Frontiers in immunology 4 (2013): 302 (Year: 2013).*

Han, May H., et al. Journal of Experimental Medicine 209.7 (2012): 1325-1334). (Year: 2012).*

Roberts, David D, and Jeffrey S Isenberg. American journal of physiology. Cell physiology vol. 321,2 (2021) (Year: 2021).*

Kipriyanov, Sergey M., and Fabrice Le Gall. "Generation and production of engineered antibodies." Molecular biotechnology 26.1 (2004): 39-60.(Year: 2004).*

Janeway, Charles A. "Immunobiology: The Immune System in Health and Disease." 2001 (Year: 2001).*

International Search Report and Written Opinion dated Nov. 26, 2018 in International Application No. PCT/US2018/044384.

* cited by examiner

ANTI-CD47 ANTIBODIES AND USES THEREOF

CROSS REFERENCE TO RELATED APPLICATIONS

This application is a Section 371 of International Application No. PCT/US2018/044384, filed Jul. 30, 2018, which published in the English language on Feb. 7, 2019 under International Publication No. WO 2019/027903 A1, which claims priority to U.S. Provisional Application No. 62/540,118, filed on Aug. 2, 2017, and U.S. Provisional Application No. 62/657,094, filed on Apr. 13, 2018. Each disclosure is incorporated herein by reference in its entirety.

FIELD OF THE INVENTION

This invention relates to monoclonal anti-CD47 antibodies, nucleic acids and expression vectors encoding the antibodies, recombinant cells containing the vectors, and compositions comprising the antibodies. Methods of making the antibodies, and methods of using the antibodies to treat diseases including cancer, inflammatory diseases, infectious diseases, atherosclerosis, cardiovascular disease, metabolic diseases, radiation-induced injury, and/or autoimmune diseases are also provided.

REFERENCE TO SEQUENCE LISTING SUBMITTED ELECTRONICALLY

This application contains a sequence listing, which is submitted electronically via EFS-Web as an ASCII formatted sequence listing with a file name "689204.2U1 Sequence Listing" and a creation date of Jan. 21, 2020, and having a size of 95 kb. The sequence listing submitted via EFS-Web is part of the specification and is herein incorporated by reference in its entirety.

BACKGROUND OF THE INVENTION

Cancer cells can evolve various canning capabilities to avoid the attack by the host, including that from the immune system. They either adopt the native appearance on cell surface as normal human cells or interrupt the immune attack upon capture by immune cells. The latter mechanism has been firmly vindicated by the astonishing success of therapeutic monoclonal antibodies targeting immune suppressors CTLA-4, PD-1 and PD-L1. These antibodies inactivate the immune checkpoint and allow T-cells to organize effective attacks on cancer cells, resulting in durable efficacy in some patients. The early success of these antibodies rejuvenated the field of immuno-oncology and inspired research and development of more therapeutics to mobilize the human immune system to fight cancer.

The human immune system consists of adaptive and innate immunities. Current checkpoint blockers and tumor microenvironment modulators in clinical practice or in pharmaceutical development target the adaptive immunity. The checkpoint blockers and tumor microenvironment modulators mobilize T-cells by rescuing helper T-cells and killer T-cells from exhaustion, depleting immunosuppressive regulatory T-cells, or blocking the formation of the immune-suppressive tumor microenvironment. More recently, emerging evidence indicates that tumor cells also suppress innate immunity and alleviating such suppression has demonstrated great therapeutic potential in vitro and in vivo in treating cancers.

Innate immunity is the first line defense against invading pathogens. It is made up of defensive mechanisms and antigen engulfing leukocytes. Among them, the macrophages remove dysfunctional aged and infected host cells by phagocytosis. Tumor cells also evade macrophage attack by overexpressing cluster of differentiation 47 (CD47) (also known as integrin-associated protein), a marker that is also ubiquitously expressed on the surface of normal cells. Remarkably, in the presence of antibodies that specifically block CD47, macrophages attack tumor cells in vitro in phagocytosis assay and eradicate tumors in vivo in xenograft models. Currently, several therapeutic agents that target CD47 have entered clinical phase of drug development.

CD47, first identified as an integrin associated protein, is a receptor-ligand and interacts with many proteins. CD47 is the receptor to thrombospondin-1 (TSP1), one of the best characterized secreted ligands. On the other hand, CD47 is the ligand to signal regulatory protein alpha (SIRPα), an inhibitory receptor expressed on the surface of macrophages. It is the latter binding that prevents macrophage from ingesting cancer cells.

As of all cancer immunotherapies, blocking CD47 may induce unintended immune attack on normal cells, causing dose-limiting toxicity. Indeed, a CD47 blocking antibody, B6H12, causes hemagglutination, presumably by binding to CD47 on the red blood cells. Remarkably, this antibody blocks the binding of both TSP1 and SIRPα to CD47. It is unclear, however, whether the blocking of TSP1 interaction by B6H12 is responsible for the hemagglutination. Furthermore, it is proposed that macrophages may attack normal cells when their surface CD47 molecules are masked by systematically administrated anti-CD47 antibodies. Therefore, it is of great importance to develop anti-CD47 antibodies that have increased specificity to tumor cells and reduced toxicity to normal cells.

BRIEF SUMMARY OF THE INVENTION

In one general aspect, the invention relates to isolated monoclonal antibodies or antigen-binding fragments thereof that bind CD47.

Provided are isolated monoclonal antibodies or antigen-binding fragments thereof comprising a heavy chain complementarity determining region 1 (HCDR1), HCDR2, HCDR3, a light chain complementarity determining region 1 (LCDR1), LCDR2, and LCDR3, having the polypeptide sequences of:
  (1) SEQ ID NOs:177, 46, 47, 178, 112, and 179, respectively;
  (2) SEQ ID NOs:51, 52, 53, 117, 118, and 119, respectively;
  (3) SEQ ID NOs:54, 55, 56, 120, 121, and 122, respectively;
  (4) SEQ ID NOs:57, 58, 59, 123, 124, and 125, respectively;
  (5) SEQ ID NOs:60, 61, 62, 126, 127, and 128, respectively;
  (6) SEQ ID NOs:180, 181, 182, 129, 130, and 131, respectively;
  (7) SEQ ID NOs:72, 73, 74, 138, 139, and 140, respectively;
  (8) SEQ ID NOs:78, 79, 80, 144, 145, and 146, respectively;
  (9) SEQ ID NOs:81, 82, 83, 147, 148, and 149, respectively;
  (10) SEQ ID NOs:84, 85, 86, 150, 151, and 152, respectively;

(11) SEQ ID NOs:87, 88, 89, 153, 154, and 155, respectively;
(12) SEQ ID NOs:90, 91, 92, 156, 157, and 158, respectively;
(13) SEQ ID NOs:93, 94, 95, 159, 160, and 161, respectively;
(14) SEQ ID NOs:96, 97, 98, 162, 163, and 164, respectively;
(15) SEQ ID NOs:99, 100, 101, 165, 166, and 167, respectively;
(16) SEQ ID NOs:102, 103, 104, 168, 169, and 170, respectively;
(17) SEQ ID NOs:105, 106, 107, 171, 172, and 173, respectively;
(18) SEQ ID NOs:108, 109, 110, 174, 175, and 176, respectively; or
(19) SEQ ID NOs:201, 202, 203, 204, 205, and 206, respectively;

wherein the antibody or antigen-binding fragment thereof specifically binds CD47, preferably human CD47. SEQ ID NO:177 is represented by the amino acid sequence GYTFTX$_1$YY, wherein X$_1$ is an amino acid selected from D or A. SEQ ID NO:178 is represented by the amino acid sequence X$_1$NVGTY, wherein X$_1$ is an amino acid selected from D or E. SEQ ID NO:179 is represented by the amino acid sequence GQX$_1$YSYPLT, wherein X$_1$ is an amino acid selected from S or T. SEQ ID NO:180 is represented by the amino acid sequence GYTFTSX$_1$W, wherein X$_1$ is an amino acid selected from S or Y. SEQ ID NO:181 is represented by the amino acid sequence IDPSDSEX$_1$, wherein X$_1$ is an amino acid selected from T or A. SEQ ID NO:182 is represented by the amino acid sequence X$_1$RWGYYGKSAX$_2$DY, wherein X$_1$ is an amino acid selected from A or S and X$_2$ is an amino acid selected from I or M.

In certain embodiments, the isolated monoclonal antibody or antigen-binding fragment comprises a heavy chain variable region having a polypeptide sequence at least 95% identical to SEQ ID NO:1, 3, 5, 7, 9, 11, 13, 15, 17, 19, 21, 23, 25, 27, 29, 31, 33, 35, 37, 39, 41, or 43, or a light chain variable region having a polypeptide sequence at least 95% identical to SEQ ID NO:2, 4, 6, 8, 10, 12, 14, 16, 18, 20, 22, 24, 26, 28, 30, 32, 34, 36, 38, 40, 42, or 44.

In certain embodiments, the isolated monoclonal antibody or antigen-binding fragment comprises:
(a) a heavy chain variable region having the polypeptide sequence of SEQ ID NO:1, and a light chain variable region having the polypeptide sequence of SEQ ID NO:2;
(b) a heavy chain variable region having the polypeptide sequence of SEQ ID NO:3, and a light chain variable region having the polypeptide sequence of SEQ ID NO:4;
(c) a heavy chain variable region having the polypeptide sequence of SEQ ID NO:5, and a light chain variable region having the polypeptide sequence of SEQ ID NO:6;
(d) a heavy chain variable region having the polypeptide sequence of SEQ ID NO:7, and a light chain variable region having the polypeptide sequence of SEQ ID NO:8;
(e) a heavy chain variable region having the polypeptide sequence of SEQ ID NO:9, and a light chain variable region having the polypeptide sequence of SEQ ID NO:10;
(f) a heavy chain variable region having the polypeptide sequence of SEQ ID NO:11, and a light chain variable region having the polypeptide sequence of SEQ ID NO:12;
(g) a heavy chain variable region having the polypeptide sequence of SEQ ID NO:13, and a light chain variable region having the polypeptide sequence of SEQ ID NO:14;
(h) a heavy chain variable region having the polypeptide sequence of SEQ ID NO:15, and a light chain variable region having the polypeptide sequence of SEQ ID NO:16;
(i) a heavy chain variable region having the polypeptide sequence of SEQ ID NO:17, and a light chain variable region having the polypeptide sequence of SEQ ID NO:18;
(j) a heavy chain variable region having the polypeptide sequence of SEQ ID NO:19, and a light chain variable region having the polypeptide sequence of SEQ ID NO:20;
(k) a heavy chain variable region having the polypeptide sequence of SEQ ID NO:21, and a light chain variable region having the polypeptide sequence of SEQ ID NO:22;
(l) a heavy chain variable region having the polypeptide sequence of SEQ ID NO:23, and a light chain variable region having the polypeptide sequence of SEQ ID NO:24;
(m) a heavy chain variable region having the polypeptide sequence of SEQ ID NO:25, and a light chain variable region having the polypeptide sequence of SEQ ID NO:26;
(n) a heavy chain variable region having the polypeptide sequence of SEQ ID NO:27, and a light chain variable region having the polypeptide sequence of SEQ ID NO:28;
(o) a heavy chain variable region having the polypeptide sequence of SEQ ID NO:29, and a light chain variable region having the polypeptide sequence of SEQ ID NO:30;
(p) a heavy chain variable region having the polypeptide sequence of SEQ ID NO:31, and a light chain variable region having the polypeptide sequence of SEQ ID NO:32;
(q) a heavy chain variable region having the polypeptide sequence of SEQ ID NO:33, and a light chain variable region having the polypeptide sequence of SEQ ID NO:34;
(r) a heavy chain variable region having the polypeptide sequence of SEQ ID NO:35, and a light chain variable region having the polypeptide sequence of SEQ ID NO:36;
(s) a heavy chain variable region having the polypeptide sequence of SEQ ID NO:37, and a light chain variable region having the polypeptide sequence of SEQ ID NO:38;
(t) a heavy chain variable region having the polypeptide sequence of SEQ ID NO:39, and a light chain variable region having the polypeptide sequence of SEQ ID NO:40;
(u) a heavy chain variable region having the polypeptide sequence of SEQ ID NO:41, and a light chain variable region having the polypeptide sequence of SEQ ID NO:42; or (v) a heavy chain variable region having the polypeptide sequence of SEQ ID NO:43, and a light chain variable region having the polypeptide sequence of SEQ ID NO:44.

In certain embodiments, the isolated monoclonal antibody or antigen-binding fragment thereof is chimeric.

In certain embodiments, the isolated monoclonal antibody or antigen-binding fragment thereof is human or humanized. In certain embodiments, the humanized monoclonal antibody or antigen-binding fragment thereof comprises:
a. a heavy chain variable region having the polypeptide sequence of SEQ ID NO:183, and a light chain variable region having the polypeptide sequence of SEQ ID NO:191;
b. a heavy chain variable region having the polypeptide sequence of SEQ ID NO:183, and a light chain variable region having the polypeptide sequence of SEQ ID NO:192;
c. a heavy chain variable region having the polypeptide sequence of SEQ ID NO:183, and a light chain variable region having the polypeptide sequence of SEQ ID NO:193;
d. a heavy chain variable region having the polypeptide sequence of SEQ ID NO:184, and a light chain variable region having the polypeptide sequence of SEQ ID NO:190;
e. a heavy chain variable region having the polypeptide sequence of SEQ ID NO:184, and a light chain variable region having the polypeptide sequence of SEQ ID NO:192;
f. a heavy chain variable region having the polypeptide sequence of SEQ ID NO:184, and a light chain variable region having the polypeptide sequence of SEQ ID NO:193;
g. a heavy chain variable region having the polypeptide sequence of SEQ ID NO:185, and a light chain variable region having the polypeptide sequence of SEQ ID NO:190;
h. a heavy chain variable region having the polypeptide sequence of SEQ ID NO:185, and a light chain variable region having the polypeptide sequence of SEQ ID NO:191;
i. a heavy chain variable region having the polypeptide sequence of SEQ ID NO:185, and a light chain variable region having the polypeptide sequence of SEQ ID NO:193;
j. a heavy chain variable region having the polypeptide sequence of SEQ ID NO:185, and a light chain variable region having the polypeptide sequence of SEQ ID NO:198;
k. a heavy chain variable region having the polypeptide sequence of SEQ ID NO:187, and a light chain variable region having the polypeptide sequence of SEQ ID NO:194;
l. a heavy chain variable region having the polypeptide sequence of SEQ ID NO:188, and a light chain variable region having the polypeptide sequence of SEQ ID NO:194;
m. a heavy chain variable region having the polypeptide sequence of SEQ ID NO:188, and a light chain variable region having the polypeptide sequence of SEQ ID NO:196;
n. a heavy chain variable region having the polypeptide sequence of SEQ ID NO:188, and a light chain variable region having the polypeptide sequence of SEQ ID NO:197; or
o. a heavy chain variable region having the polypeptide sequence of SEQ ID NO:199, and a light chain variable region having the polypeptide sequence of SEQ ID NO:200.

In certain embodiments, the isolated monoclonal antibody or antigen-binding fragment thereof is capable of blocking binding of CD47 to thrombospondin-1 (TSP1) and/or to signal regulatory protein alpha (SIRPα).

In certain embodiments, the isolated monoclonal antibody or antigen-binding fragment thereof is capable of inducing macrophage-mediated phagocytosis of cancer cells.

In certain embodiments, the isolated monoclonal antibody or antigen-binding fragment thereof is capable of binding cancer cells with minimal to undetectable binding to red blood cells.

Also provided are isolated nucleic acids encoding the monoclonal antibodies or antigen-binding fragments thereof of the invention.

Also provided are vectors comprising the isolated nucleic acids encoding the monoclonal antibodies or antigen-binding fragments thereof of the invention.

Also provided are host cells comprising the vectors comprising the isolated nucleic acids encoding the monoclonal antibodies or antigen-binding fragments thereof of the invention.

In certain embodiments, provided is a pharmaceutical composition comprising the isolated monoclonal antibody or antigen-binding fragment thereof of the invention and a pharmaceutically acceptable carrier.

Also provided are methods of blocking binding of CD47 to thrombospondin-1 (TSP1) and/or CD47 to signal regulatory protein alpha (SIRPα) in a subject in need thereof, comprising administering to the subject the pharmaceutical compositions of the invention.

Also provided are methods of treating cancer in a subject in need thereof, comprising administering to the subject the pharmaceutical compositions of the invention. The cancer can be any liquid or solid cancer, for example, it can be selected from but not limited to, a lung cancer, a gastric cancer, a colon cancer, a hepatocellular carcinoma, a renal cell carcinoma, a bladder urothelial carcinoma, a metastatic melanoma, a breast cancer, an ovarian cancer, a cervical cancer, a head and neck cancer, a pancreatic cancer, a glioma, a glioblastoma, and other solid tumors, and a non-Hodgkin's lymphoma (NHL), an acute lymphocytic leukemia (ALL), a chronic lymphocytic leukemia (CLL), a chronic myelogenous leukemia (CIVIL), a multiple myeloma (MM), an acute myeloid leukemia (AML), and other liquid tumors.

Also provided are methods of treating an inflammatory disease in a subject in need thereof, comprising administering to the subject the pharmaceutical compositions of the invention.

Also provided are methods of treating an infectious disease in a subject in need thereof, comprising administering to the subject the pharmaceutical compositions of the invention.

Also provided are methods of treating atherosclerosis in a subject in need thereof, comprising administering to the subject the pharmaceutical compositions of the invention.

Also provided are methods of treating a cardiovascular disease in a subject in need thereof, comprising administering to the subject the pharmaceutical compositions of the invention.

Also provided are methods of treating a metabolic disease in a subject in need thereof, comprising administering to the subject the pharmaceutical compositions of the invention.

Also provided are methods of treating a radiation-induced injury in a subject in need thereof, comprising administering to the subject the pharmaceutical compositions of the invention.

Also provided are methods of treating an autoimmune disease in a subject in need thereof, comprising administering to the subject the pharmaceutical compositions of the invention.

Also provided are methods of determining a level of CD47 in a subject. The methods comprise (a) obtaining a sample from the subject; (b) contacting the sample with an antibody or antigen-binding fragment thereof of the invention; and (c) determining a level of CD47 in the subject. In certain embodiments, the sample is a tissue or blood sample. The tissue sample can, for example, be a cancer tissue sample. The blood sample can, for example, comprise cancer cells.

Also provided are methods of producing the monoclonal antibody or antigen-binding fragment thereof of the invention, comprising culturing a cell comprising a nucleic acid encoding the monoclonal antibody or antigen-binding fragment under conditions to produce the monoclonal antibody or antigen-binding fragment, and recovering the antibody or antigen-binding fragment from the cell or culture.

Also provided are methods of producing a pharmaceutical composition comprising the monoclonal antibody or antigen-binding fragment thereof of the invention, comprising combining the monoclonal antibody or antigen-binding fragment with a pharmaceutically acceptable carrier to obtain the pharmaceutical composition.

BRIEF DESCRIPTION OF THE DRAWINGS

The foregoing summary, as well as the following detailed description of preferred embodiments of the present application, will be better understood when read in conjunction with the appended drawings. It should be understood, however, that the application is not limited to the precise embodiments shown in the drawings.

FIG. 2A shows a graph of the activity of the anti-CD47 mAb 15G23A. FIG. 2P shows a graph of the activity of the anti-CD47 mAb 18M19A (chimeric with human IgG4 heavy chain and kappa light chain).

FIG. 3A shows the results of the hemagglutination assay for anti-CD47 mAbs 14P6A, 11F6A, 18M19A, 19L14A, 305A, 10123A, 14N13A, 14O18A, 13C4A, 16M17A, and 17O12A. FIG. 3B shows the results of the hemagglutination assay for anti-CD47 mAbs 12B18A, 4M8A, 13B18A, 11G2A, 5D24A, 14D18A, 17C6A, 17N8A, 9O23A, 15G23A, and 1J7A and controls PBS and B6H12.

FIG. 4A shows the in vivo anti-tumor activity of 13B18A-huIgG1 in a RAJI xenograft mouse model; rituximab was used as positive control. FIG. 4B shows the body weight data of the animals in different groups during the study. FIG. 4C shows the serum exposure of 13B18A-huIgG1 in mAb-treated groups 2 days after the final dose.

DETAILED DESCRIPTION OF THE INVENTION

Figure 1:
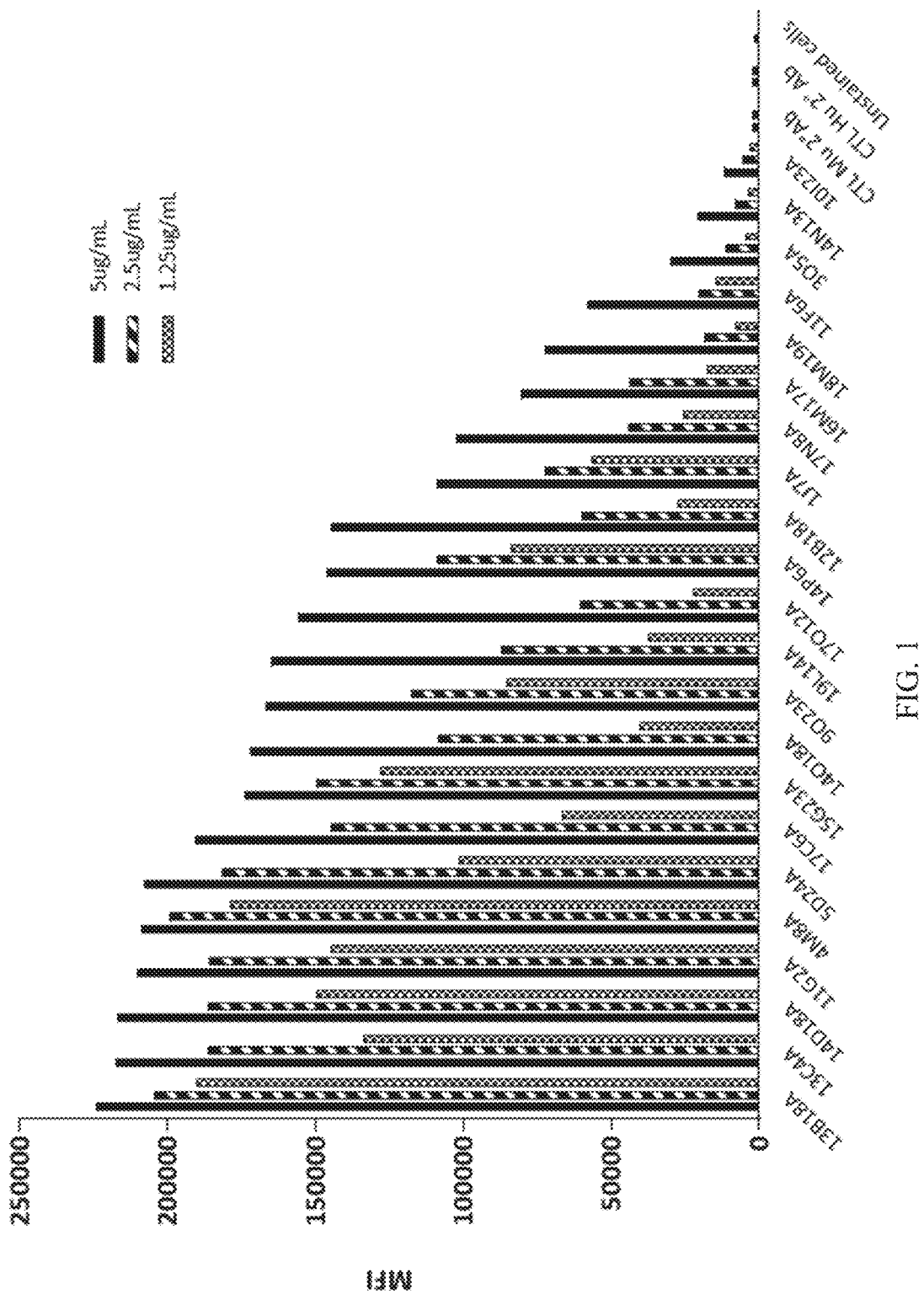
FIG. 1 shows a graph of the binding of anti-CD47 mAbs to RAJI cells by FACS analysis. The control groups "CTL Mu 2° Ab" and "CTL Hu 2° Ab" were not treated with primary antibodies, but were treated with AlexaFluor488-conjugated anti-mouse and anti-human IgG secondary Abs, respectively.

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the invention. Such discussion is not an admission that any or all of these matters form part of the prior art with respect to any inventions disclosed or claimed.

Unless defined otherwise, all technical and scientific terms used herein have the same meaning as commonly understood to one of ordinary skill in the art to which this invention pertains. Otherwise, certain terms used herein have the meanings as set forth in the specification.

It must be noted that as used herein and in the appended claims, the singular forms "a," "an," and "the" include plural reference unless the context clearly dictates otherwise.

Unless otherwise stated, any numerical values, such as a concentration or a concentration range described herein, are to be understood as being modified in all instances by the term "about." Thus, a numerical value typically includes ±10% of the recited value. For example, a concentration of 1 mg/mL includes 0.9 mg/mL to 1.1 mg/mL. Likewise, a concentration range of 1% to 10% (w/v) includes 0.9% (w/v) to 11% (w/v). As used herein, the use of a numerical range expressly includes all possible subranges, all individual numerical values within that range, including integers within such ranges and fractions of the values unless the context clearly indicates otherwise.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the invention.

As used herein, the terms "comprises," "comprising," "includes," "including," "has," "having," "contains" or "containing," or any other variation thereof, will be understood to imply the inclusion of a stated integer or group of integers but not the exclusion of any other integer or group of integers and are intended to be non-exclusive or open-ended. For example, a composition, a mixture, a process, a method, an article, or an apparatus that comprises a list of elements is not necessarily limited to only those elements but can include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

As used herein, the conjunctive term "and/or" between multiple recited elements is understood as encompassing both individual and combined options. For instance, where two elements are conjoined by "and/or," a first option refers to the applicability of the first element without the second. A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or."

As used herein, the term "consists of," or variations such as "consist of" or "consisting of," as used throughout the specification and claims, indicate the inclusion of any recited integer or group of integers, but that no additional integer or group of integers can be added to the specified method, structure, or composition.

As used herein, the term "consists essentially of," or variations such as "consist essentially of" or "consisting essentially of," as used throughout the specification and claims, indicate the inclusion of any recited integer or group of integers, and the optional inclusion of any recited integer or group of integers that do not materially change the basic or novel properties of the specified method, structure or composition. See M.P.E.P. § 2111.03.

As used herein, "subject" means any animal, preferably a mammal, most preferably a human. The term "mammal" as used herein, encompasses any mammal. Examples of mammals include, but are not limited to, cows, horses, sheep, pigs, cats, dogs, mice, rats, rabbits, guinea pigs, monkeys, humans, etc., more preferably a human.

The words "right," "left," "lower," and "upper" designate directions in the drawings to which reference is made.

It should also be understood that the terms "about," "approximately," "generally," "substantially," and like terms, used herein when referring to a dimension or characteristic of a component of the preferred invention, indicate that the described dimension/characteristic is not a strict boundary or parameter and does not exclude minor variations therefrom that are functionally the same or similar, as would be understood by one having ordinary skill in the art. At a minimum, such references that include a numerical parameter would include variations that, using mathematical and industrial principles accepted in the art (e.g., rounding, measurement or other systematic errors, manufacturing tolerances, etc.), would not vary the least significant digit.

The terms "identical" or percent "identity," in the context of two or more nucleic acids or polypeptide sequences (e.g., anti-CD47 antibodies, CD47 polypeptides, and polynucleotides that encode them), refer to two or more sequences or subsequences that are the same or have a specified percentage of amino acid residues or nucleotides that are the same, when compared and aligned for maximum correspondence, as measured using one of the following sequence comparison algorithms or by visual inspection.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, Current Protocols in Molecular Biology, F. M. Ausubel et al., eds., Current Protocols, a joint venture between Greene Publishing Associates, Inc. and John Wiley & Sons, Inc., (1995 Supplement) (Ausubel)).

Examples of algorithms that are suitable for determining percent sequence identity and sequence similarity are the BLAST and BLAST 2.0 algorithms, which are described in Altschul et al. (1990) J. Mol. Biol. 215: 403-410 and Altschul et al. (1997) Nucleic Acids Res. 25: 3389-3402, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased.

Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, Proc. Natl. Acad. Sci. USA 89:10915 (1989)).

In addition to calculating percent sequence identity, the BLAST algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences or polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions.

As used herein, the terms "inhibit," "inhibiting," and "inhibition," mean to decrease an activity, response, condition, disease or other biological parameter. This can include, but is not limited to complete ablation of the activity, response, condition, or disease. This may also include, for example, a 10% reduction in the activity, response, condition, or disease as compared to the native or control level. Thus, the reduction can be a 10, 20, 30, 40, 50, 60, 70, 80, 90, 100%, or any amount of reduction in between, as compared to native or control levels. By way of a non-limiting example, an antibody of the invention can inhibit the activity of a CD47 protein. The activity of the CD47 protein can be reduced or ablated relative to the native CD47 protein activity.

Antibodies

The invention generally relates to isolated anti-CD47 antibodies, nucleic acids and expression vectors encoding the antibodies, recombinant cells containing the vectors, and compositions comprising the antibodies. Methods of making the antibodies, and methods of using the antibodies to treat diseases including cancer, inflammatory diseases, autoimmune diseases, atherosclerosis, cardiovascular disease, metabolic diseases, radiation-induced injury, and/or infectious diseases are also provided. The antibodies of the invention possess one or more desirable functional properties, including but not limited to high-affinity binding to CD47, high specificity to CD47, the ability and/or inability to block the binding of CD47 to thrombospondin-1 (TSP1), the ability to block the binding of CD47 to signal regulatory protein alpha (SIRPα), the ability to induce phagocytosis of CD47 expressing cells associated with disease or disorder (including, but not limited to, cancer and atherosclerosis), and the ability to inhibit tumor growth in animal models and subjects when administered alone or in combination with other anti-cancer therapies, and the inability to induce hemagglutination.

In a general aspect, the invention relates to isolated monoclonal antibodies or antigen-binding fragments thereof that bind CD47.

As used herein, the term "antibody" is used in a broad sense and includes immunoglobulin or antibody molecules including human, humanized, composite and chimeric antibodies and antibody fragments that are monoclonal or polyclonal. In general, antibodies are proteins or peptide chains that exhibit binding specificity to a specific antigen. Antibody structures are well known. Immunoglobulins can be assigned to five major classes (i.e., IgA, IgD, IgE, IgG and IgM), depending on the heavy chain constant domain amino acid sequence. IgA and IgG are further sub-classified as the isotypes IgA1, IgA2, IgG1, IgG2, IgG3 and IgG4. Accordingly, the antibodies of the invention can be of any of the five major classes or corresponding sub-classes. Preferably, the antibodies of the invention are IgG1, IgG2, IgG3 or IgG4. Antibody light chains of vertebrate species can be assigned to one of two clearly distinct types, namely kappa and lambda, based on the amino acid sequences of their constant domains. Accordingly, the antibodies of the invention can contain a kappa or lambda light chain constant domain. According to particular embodiments, the antibodies of the invention include heavy and/or light chain constant regions from rat or human antibodies. In addition to the heavy and light constant domains, antibodies contain an antigen-binding region that is made up of a light chain variable region and a heavy chain variable region, each of which contains three domains (i.e., complementarity determining regions 1-3; (CDR1, CDR2, and CDR3)). The light chain variable region domains are alternatively referred to as LCDR1, LCDR2, and LCRD3, and the heavy chain variable region domains are alternatively referred to as HCDR1, HCRD2, and HCDR3.

As used herein, the term an "isolated antibody" refers to an antibody which is substantially free of other antibodies having different antigenic specificities (e.g., an isolated antibody that specifically binds to CD47 is substantially free of antibodies that do not bind to CD47). In addition, an isolated antibody is substantially free of other cellular material and/or chemicals.

As used herein, the term "monoclonal antibody" refers to an antibody obtained from a population of substantially homogeneous antibodies, i.e., the individual antibodies comprising the population are identical except for possible naturally occurring mutations that may be present in minor amounts. The monoclonal antibodies of the invention can be made by the hybridoma method, phage display technology, single lymphocyte gene cloning technology, or by recombinant DNA methods. For example, the monoclonal antibodies can be produced by a hybridoma which includes a B cell obtained from a transgenic nonhuman animal, such as a transgenic mouse or rat, having a genome comprising a human heavy chain transgene and a light chain transgene.

As used herein, the term "antigen-binding fragment" refers to an antibody fragment such as, for example, a diabody, a Fab, a Fab', a F(ab')2, an Fv fragment, a disulfide stabilized Fv fragment (dsFv), a (dsFv)$_2$, a bispecific dsFv (dsFv-dsFv'), a disulfide stabilized diabody (ds diabody), a single-chain antibody molecule (scFv), a single domain antibody (sdab) an scFv dimer (bivalent diabody), a multispecific antibody formed from a portion of an antibody comprising one or more CDRs, a camelized single domain antibody, a nanobody, a domain antibody, a bivalent domain antibody, or any other antibody fragment that binds to an antigen but does not comprise a complete antibody structure. An antigen-binding fragment is capable of binding to the same antigen to which the parent antibody or a parent antibody fragment binds. According to particular embodiments, the antigen-binding fragment comprises a light chain variable region, a light chain constant region, and an Fd segment of the heavy chain. According to other particular embodiments, the antigen-binding fragment comprises Fab and F(ab').

As used herein, the term "single-chain antibody" refers to a conventional single-chain antibody in the field, which comprises a heavy chain variable region and a light chain variable region connected by a short peptide of about 15 to about 20 amino acids. As used herein, the term "single domain antibody" refers to a conventional single domain antibody in the field, which comprises a heavy chain variable region and a heavy chain constant region or which comprises only a heavy chain variable region.

As used herein, the term "human antibody" refers to an antibody produced by a human or an antibody having an amino acid sequence corresponding to an antibody produced by a human made using any technique known in the art. This definition of a human antibody includes intact or full-length antibodies, fragments thereof, and/or antibodies comprising at least one human heavy and/or light chain polypeptide.

As used herein, the term "humanized antibody" refers to a non-human antibody that is modified to increase the sequence homology to that of a human antibody, such that the antigen-binding properties of the antibody are retained, but its antigenicity in the human body is reduced.

As used herein, the term "chimeric antibody" refers to an antibody wherein the amino acid sequence of the immunoglobulin molecule is derived from two or more species. The variable region of both the light and heavy chains often corresponds to the variable region of an antibody derived from one species of mammal (e.g., mouse, rat, rabbit, etc.) having the desired specificity, affinity, and capability, while the constant regions correspond to the sequences of an antibody derived from another species of mammal (e.g., human) to avoid eliciting an immune response in that species.

As used herein, the term "multispecific antibody" refers to an antibody that comprises a plurality of immunoglobulin variable domain sequences, wherein a first immunoglobulin variable domain sequence of the plurality has binding specificity for a first epitope and a second immunoglobulin variable domain sequence of the plurality has binding specificity for a second epitope. In an embodiment, the first and second epitopes are on the same antigen, e.g., the same protein (or subunit of a multimeric protein). In an embodiment, the first and second epitopes overlap or substantially overlap. In an embodiment, the first and second epitopes do not overlap or do not substantially overlap. In an embodiment, the first and second epitopes are on different antigens, e.g., the different proteins (or different subunits of a multimeric protein). In an embodiment, a multispecific antibody comprises a third, fourth, or fifth immunoglobulin variable domain. In an embodiment, a multispecific antibody is a bispecific antibody molecule, a trispecific antibody, or a tetraspecific antibody molecule.

As used herein, the term "bispecifc antibody" refers to a multispecific antibody that binds no more than two epitopes or two antigens. A bispecific antibody is characterized by a first immunoglobulin variable domain sequence which has binding specificity for a first epitope and a second immunoglobulin variable domain sequence that has binding specificity for a second epitope. In an embodiment, the first and second epitopes are on the same antigen, e.g., the same protein (or subunit of a multimeric protein). In an embodiment, the first and second epitopes overlap or substantially overlap. In an embodiment the first and second epitopes are on different antigens, e.g., the different proteins (or different subunits of a multimeric protein). In an embodiment a bispecific antibody comprises a heavy chain variable domain sequence and a light chain variable domain sequence which have binding specificity for a first epitope and a heavy chain variable domain sequence and a light chain variable domain sequence which have binding specificity for a second epitope. In an embodiment, a bispecific antibody comprises a half antibody, or fragment thereof, having binding specificity for a first epitope and a half antibody, or fragment thereof, having binding specificity for a second epitope. In an embodiment, a bispecific antibody comprises a scFv, or fragment thereof, having binding specificity for a first epitope, and a scFv, or fragment thereof, having binding specificity for a second epitope. In an embodiment, the first epitope is located on CD47 and the second epitope is located on PD-1, PD-L1, LAG-3, TIM-3, CTLA-4, EGFR, HER-2, CD19, CD20, CD33, CD73, apelin, DLL3, claudin18.2, TIP-1, folate receptor alpha, CD3 and/or other tumor associated immune suppressors or surface antigens.

As used herein, the term "CD47" refers to a multi-spanning transmembrane receptor belonging to the immunoglobulin superfamily, which has been indicated to be involved in multiple cellular process, including cell migration, adhesion, and T cell function. CD47, also known as integrin-associated protein (IAP), ovarian cancer antigen (OA3), Rh-related antigen, and MER6, was originally identified as a tumor antigen on human ovarian cancer and was subsequently shown to be expressed on multiple human tumor types, including both hematologic and solid tumors. The interaction between CD47 and signal regulatory protein alpha (SIRPα), an inhibitory protein expressed on macrophages, prevents phagocytosis of CD47-expressing cells. CD47 is additionally expressed at low levels on virtually all non-malignant cells. The term "human CD47" refers to a CD47 originated from a human. An exemplary amino acid sequence of a human CD47 is represented in GenBank Accession No. NP_001768.1 (SEQ ID NO:207).

As used herein, an antibody that "specifically binds to CD47" refers to an antibody that binds to a CD47, preferably a human CD47, with a KD of $1 \times 10^{-7}$ M or less, preferably $1 \times 10^{-8}$ M or less, more preferably $5 \times 10^{-9}$ M or less, $1 \times 10^{-9}$ M or less, $5 \times 10^{-10}$ M or less, or $1 \times 10^{-10}$ M or less. The term "KD" refers to the dissociation constant, which is obtained from the ratio of Kd to Ka (i.e., Kd/Ka) and is expressed as a molar concentration (M). KD values for antibodies can be determined using methods in the art in view of the present disclosure. For example, the KD of an antibody can be determined by using surface plasmon resonance, such as by using a biosensor system, e.g., a Biacore® system, or by using bio-layer interferometry technology, such as a Octet RED96 system.

The smaller the value of the KD of an antibody, the higher affinity that the antibody binds to a target antigen.

According to a particular aspect, the invention relates to an isolated monoclonal antibody or antigen-binding fragment thereof comprising a heavy chain complementarity determining region 1 (HCDR1), a HCDR2, a HCDR3, a light chain complementarity determining region 1 (LCDR1), a LCDR2, and a LCDR3, having the polypeptide sequences of:
- (1) SEQ ID NOs:177, 46, 47, 178, 112, and 179, respectively;
- (2) SEQ ID NOs:51, 52, 53, 117, 118, and 119, respectively;
- (3) SEQ ID NOs:54, 55, 56, 120, 121, and 122, respectively;
- (4) SEQ ID NOs:57, 58, 59, 123, 124, and 125, respectively;
- (5) SEQ ID NOs:60, 61, 62, 126, 127, and 128, respectively;
- (6) SEQ ID NOs:180, 181, 182, 129, 130, and 131, respectively;
- (7) SEQ ID NOs:72, 73, 74, 138, 139, and 140, respectively;
- (8) SEQ ID NOs:78, 79, 80, 144, 145, and 146, respectively;
- (9) SEQ ID NOs:81, 82, 83, 147, 148, and 149, respectively;
- (10) SEQ ID NOs:84, 85, 86, 150, 151, and 152, respectively;
- (11) SEQ ID NOs:87, 88, 89, 153, 154, and 155, respectively;
- (12) SEQ ID NOs:90, 91, 92, 156, 157, and 158, respectively;
- (13) SEQ ID NOs:93, 94, 95, 159, 160, and 161, respectively;
- (14) SEQ ID NOs:96, 97, 98, 162, 163, and 164, respectively;
- (15) SEQ ID NOs:99, 100, 101, 165, 166, and 167, respectively;
- (16) SEQ ID NOs:102, 103, 104, 168, 169, and 170, respectively;
- (17) SEQ ID NOs:105, 106, 107, 171, 172, and 173, respectively;
- (18) SEQ ID NOs:108, 109, 110, 174, 175, and 176, respectively; or
- (19) SEQ ID NOs:201, 202, 203, 204, 205, and 206, respectively;

wherein the antibody or antigen-binding fragment thereof specifically binds CD47, preferably human CD47.

SEQ ID NO:177 is represented by the amino acid sequence GYTFTX$_1$YY, wherein X$_1$ is an amino acid selected from D or A.

SEQ ID NO:178 is represented by the amino acid sequence X$_1$NVGTY, wherein X$_1$ is an amino acid selected from D or E.

SEQ ID NO:179 is represented by the amino acid sequence GQX$_1$YSYPLT, wherein X$_1$ is an amino acid selected from S or T.

SEQ ID NO:180 is represented by the amino acid sequence GYTFTSX$_1$W, wherein X$_1$ is an amino acid selected from S or Y.

SEQ ID NO:181 is represented by the amino acid sequence IDPSDSEX$_1$, wherein X$_1$ is an amino acid selected from T or A.

SEQ ID NO:182 is represented by the amino acid sequence X$_1$RWGYYGKSAX$_2$DY, wherein X$_1$ is an amino acid selected from A or S and X$_2$ is an amino acid selected from I or M.

According to another particular aspect, the invention relates to an isolated monoclonal antibody or antigen-binding fragment thereof comprising a heavy chain variable region having a polypeptide sequence at least 85%, preferably 90%, more preferably 95% identical to one of SEQ ID NOs:1, 3, 5, 7, 9, 11, 13, 15, 17, 19, 21, 23, 25, 27, 29, 31, 33, 35, 37, 39, 41, or 43, or a light chain variable region having a polypeptide sequence at least 85%, preferably 90%, more preferably 95% identical to one of SEQ ID NOs:2, 4, 6, 8, 10, 12, 14, 16, 18, 20, 22, 24, 26, 28, 30, 32, 34, 36, 38, 40, 42, or 44. According to one preferred embodiment, the isolated monoclonal antibody or antigen-binding fragment thereof of the invention comprises a heavy chain variable region having the polypeptide sequence at least 85%, preferably 90%, more preferably 95% identical to SEQ ID NO:1, 3, 5, 7, 9, 11, 13, 15, 17, 19, 21, 23, 25, 27, 29, 31, 33, 35, 37, 39, 41, or 43, and a light chain variable region having a polypeptide sequence at least 85%, preferably 90%, more preferably 95% identical to SEQ ID NO:2, 4, 6, 8, 10, 12, 14, 16, 18, 20, 22, 24, 26, 28, 30, 32, 34, 36, 38, 40, 42, or 44, respectively.

According to another particular aspect, the invention relates to an isolated monoclonal antibody or antigen-binding fragment thereof of the invention, comprising:
- a. a heavy chain variable region having the polypeptide sequence of SEQ ID NO:1, and a light chain variable region having the polypeptide sequence of SEQ ID NO:2;
- b. a heavy chain variable region having the polypeptide sequence of SEQ ID NO:3, and a light chain variable region having the polypeptide sequence of SEQ ID NO:4;
- c. a heavy chain variable region having the polypeptide sequence of SEQ ID NO:5, and a light chain variable region having the polypeptide sequence of SEQ ID NO:6;
- d. a heavy chain variable region having the polypeptide sequence of SEQ ID NO:7, and a light chain variable region having the polypeptide sequence of SEQ ID NO:8;
- e. a heavy chain variable region having the polypeptide sequence of SEQ ID NO:9, and a light chain variable region having the polypeptide sequence of SEQ ID NO:10;
- f. a heavy chain variable region having the polypeptide sequence of SEQ ID NO:11, and a light chain variable region having the polypeptide sequence of SEQ ID NO:12;
- g. a heavy chain variable region having the polypeptide sequence of SEQ ID NO:13, and a light chain variable region having the polypeptide sequence of SEQ ID NO:14;
- h. a heavy chain variable region having the polypeptide sequence of SEQ ID NO:15, and a light chain variable region having the polypeptide sequence of SEQ ID NO:16;
- i. a heavy chain variable region having the polypeptide sequence of SEQ ID NO:17, and a light chain variable region having the polypeptide sequence of SEQ ID NO:18;
- j. a heavy chain variable region having the polypeptide sequence of SEQ ID NO:19, and a light chain variable region having the polypeptide sequence of SEQ ID NO:20;
- k. a heavy chain variable region having the polypeptide sequence of SEQ ID NO:21, and a light chain variable region having the polypeptide sequence of SEQ ID NO:22;
- l. a heavy chain variable region having the polypeptide sequence of SEQ ID NO:23, and a light chain variable region having the polypeptide sequence of SEQ ID NO:24;

m. a heavy chain variable region having the polypeptide sequence of SEQ ID NO:25, and a light chain variable region having the polypeptide sequence of SEQ ID NO:26;
n. a heavy chain variable region having the polypeptide sequence of SEQ ID NO:27, and a light chain variable region having the polypeptide sequence of SEQ ID NO:28;
o. a heavy chain variable region having the polypeptide sequence of SEQ ID NO:29, and a light chain variable region having the polypeptide sequence of SEQ ID NO:30;
p. a heavy chain variable region having the polypeptide sequence of SEQ ID NO:31, and a light chain variable region having the polypeptide sequence of SEQ ID NO:32;
q. a heavy chain variable region having the polypeptide sequence of SEQ ID NO:33, and a light chain variable region having the polypeptide sequence of SEQ ID NO:34;
r. a heavy chain variable region having the polypeptide sequence of SEQ ID NO:35, and a light chain variable region having the polypeptide sequence of SEQ ID NO:36;
s. a heavy chain variable region having the polypeptide sequence of SEQ ID NO:37, and a light chain variable region having the polypeptide sequence of SEQ ID NO:38;
t. a heavy chain variable region having the polypeptide sequence of SEQ ID NO:39, and a light chain variable region having the polypeptide sequence of SEQ ID NO:40;
u. a heavy chain variable region having the polypeptide sequence of SEQ ID NO:41, and a light chain variable region having the polypeptide sequence of SEQ ID NO:42; or
v. a heavy chain variable region having the polypeptide sequence of SEQ ID NO:43, and a light chain variable region having the polypeptide sequence of SEQ ID NO:44.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:45, 46, 47, 111, 112, and 113, respectively. In another embodiment, the isolated monoclonal antibody or antigen-binding fragment thereof comprises a heavy chain variable region having a polypeptide sequence at least 85%, preferably 90%, more preferably 95% identical to SEQ ID NO:1, and a light chain variable region having a polypeptide sequence at least 85%, preferably 90%, more preferably 95% identical to SEQ ID NO:2. Preferably, the isolated monoclonal antibody or antigen-binding fragment thereof comprises a heavy chain variable region having the polypeptide sequence of SEQ ID NO:1; and a light chain variable region having the polypeptide sequence of SEQ ID NO:2.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:48, 49, 50, 114, 115, and 116, respectively. In another embodiment, the isolated monoclonal antibody or antigen-binding fragment thereof comprises a heavy chain variable region having a polypeptide sequence at least 85%, preferably 90%, more preferably 95% identical to SEQ ID NO:3, and a light chain variable region having a polypeptide sequence at least 85%, preferably 90%, more preferably 95% identical to SEQ ID NO:4. Preferably, the isolated monoclonal antibody or antigen-binding fragment thereof comprises a heavy chain variable region having the polypeptide sequence of SEQ ID NO:3; and a light chain variable region having the polypeptide sequence of SEQ ID NO:4.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:51, 52, 53, 117, 118, and 119, respectively. In another embodiment, the isolated monoclonal antibody or antigen-binding fragment thereof comprises a heavy chain variable region having a polypeptide sequence at least 85%, preferably 90%, more preferably 95% identical to SEQ ID NO:5, and a light chain variable region having a polypeptide sequence at least 85%, preferably 90%, more preferably 95% identical to SEQ ID NO:6. Preferably, the isolated monoclonal antibody or antigen-binding fragment thereof comprises a heavy chain variable region having the polypeptide sequence of SEQ ID NO:5; and a light chain variable region having the polypeptide sequence of SEQ ID NO:6.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:54, 55, 56, 120, 121, and 122, respectively. In another embodiment, the isolated monoclonal antibody or antigen-binding fragment thereof comprises a heavy chain variable region having a polypeptide sequence at least 85%, preferably 90%, more preferably 95% identical to SEQ ID NO:7, and a light chain variable region having a polypeptide sequence at least 85%, preferably 90%, more preferably 95% identical to SEQ ID NO:8. Preferably, the isolated monoclonal antibody or antigen-binding fragment thereof comprises a heavy chain variable region having the polypeptide sequence of SEQ ID NO:7; and a light chain variable region having the polypeptide sequence of SEQ ID NO:8.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:57, 58, 59, 123, 124, and 125, respectively. In another embodiment, the isolated monoclonal antibody or antigen-binding fragment thereof comprises a heavy chain variable region having a polypeptide sequence at least 85%, preferably 90%, more preferably 95% identical to SEQ ID NO:9, and a light chain variable region having a polypeptide sequence at least 85%, preferably 90%, more preferably 95% identical to SEQ ID NO:10. Preferably, the isolated monoclonal antibody or antigen-binding fragment thereof comprises a heavy chain variable region having the polypeptide sequence of SEQ ID NO:9; and a light chain variable region having the polypeptide sequence of SEQ ID NO:10.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:60, 61, 62, 126, 127, and 128, respectively. In another embodiment, the isolated monoclonal antibody or antigen-binding fragment thereof comprises a heavy chain variable region having a polypeptide sequence at least 85%, preferably 90%, more preferably 95% identical to SEQ ID NO:11, and a light chain variable region having a polypeptide sequence at least 85%, preferably 90%, more preferably 95% identical to SEQ ID NO:12. Preferably, the isolated monoclonal antibody or antigen-binding fragment thereof comprises a heavy chain variable region having the polypeptide sequence of SEQ ID NO:11; and a light chain variable region having the polypeptide sequence of SEQ ID NO:12.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:63, 64, 65, 129, 130, and 131, respectively. In another embodiment, the isolated monoclonal antibody or antigen-binding fragment thereof comprises a heavy chain variable region having a polypeptide sequence at least 85%, preferably 90%, more preferably 95% identical to SEQ ID NO:13, and a light chain variable region having a polypeptide sequence at least 85%, preferably 90%, more preferably 95% identical to SEQ ID NO:14. Preferably, the isolated monoclonal antibody or antigen-binding fragment thereof comprises a heavy chain variable region having the polypeptide sequence of SEQ ID NO:13; and a light chain variable region having the polypeptide sequence of SEQ ID NO:14.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:66, 67, 68, 132, 133, and 134, respectively. In another embodiment, the isolated monoclonal antibody or antigen-binding fragment thereof comprises a heavy chain variable region having a polypeptide sequence at least 85%, preferably 90%, more preferably 95% identical to SEQ ID NO:15, and a light chain variable region having a polypeptide sequence at least 85%, preferably 90%, more preferably 95% identical to SEQ ID NO:16. Preferably, the isolated monoclonal antibody or antigen-binding fragment thereof comprises a heavy chain variable region having the polypeptide sequence of SEQ ID NO:15; and a light chain variable region having the polypeptide sequence of SEQ ID NO:16.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:69, 70, 71, 135, 136, and 137, respectively. In another embodiment, the isolated monoclonal antibody or antigen-binding fragment thereof comprises a heavy chain variable region having a polypeptide sequence at least 85%, preferably 90%, more preferably 95% identical to SEQ ID NO:17, and a light chain variable region having a polypeptide sequence at least 85%, preferably 90%, more preferably 95% identical to SEQ ID NO:18. Preferably, the isolated monoclonal antibody or antigen-binding fragment thereof comprises a heavy chain variable region having the polypeptide sequence of SEQ ID NO:17; and a light chain variable region having the polypeptide sequence of SEQ ID NO:18.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:72, 73, 74, 138, 139, and 140, respectively. In another embodiment, the isolated monoclonal antibody or antigen-binding fragment thereof comprises a heavy chain variable region having a polypeptide sequence at least 85%, preferably 90%, more preferably 95% identical to SEQ ID NO:19, and a light chain variable region having a polypeptide sequence at least 85%, preferably 90%, more preferably 95% identical to SEQ ID NO:20. Preferably, the isolated monoclonal antibody or antigen-binding fragment thereof comprises a heavy chain variable region having the polypeptide sequence of SEQ ID NO:19; and a light chain variable region having the polypeptide sequence of SEQ ID NO:20.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:75, 76, 77, 141, 142, and 143, respectively. In another embodiment, the isolated monoclonal antibody or antigen-binding fragment thereof comprises a heavy chain variable region having a polypeptide sequence at least 85%, preferably 90%, more preferably 95% identical to SEQ ID NO:21, and a light chain variable region having a polypeptide sequence at least 85%, preferably 90%, more preferably 95% identical to SEQ ID NO:22. Preferably, the isolated monoclonal antibody or antigen-binding fragment thereof comprises a heavy chain variable region having the polypeptide sequence of SEQ ID NO:21; and a light chain variable region having the polypeptide sequence of SEQ ID NO:22.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:78, 79, 80, 144, 145, and 146, respectively. In another embodiment, the isolated monoclonal antibody or antigen-binding fragment thereof comprises a heavy chain variable region having a polypeptide sequence at least 85%, preferably 90%, more preferably 95% identical to SEQ ID NO:23, and a light chain variable region having a polypeptide sequence at least 85%, preferably 90%, more preferably 95% identical to SEQ ID NO:24. Preferably, the isolated monoclonal antibody or antigen-binding fragment thereof comprises a heavy chain variable region having the polypeptide sequence of SEQ ID NO:23; and a light chain variable region having the polypeptide sequence of SEQ ID NO:24.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:81, 82, 83, 147, 148, and 149, respectively. In another embodiment, the isolated monoclonal antibody or antigen-binding fragment thereof comprises a heavy chain variable region having a polypeptide sequence at least 85%, preferably 90%, more preferably 95% identical to SEQ ID NO:25, and a light chain variable region having a polypeptide sequence at least 85%, preferably 90%, more preferably 95% identical to SEQ ID NO:26. Preferably, the isolated monoclonal antibody or antigen-binding fragment thereof comprises a heavy chain variable region having the polypeptide sequence of SEQ ID NO:25; and a light chain variable region having the polypeptide sequence of SEQ ID NO:26.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:84, 85, 86, 150, 151, and 152, respectively. In another embodiment, the isolated monoclonal antibody or antigen-binding fragment thereof comprises a heavy chain variable region having a polypeptide sequence at least 85%, preferably 90%, more preferably 95% identical to SEQ ID NO:27, and a light chain variable region having a polypeptide sequence at least 85%, preferably 90%, more preferably 95% identical to SEQ ID NO:28. Preferably, the isolated monoclonal antibody or antigen-binding fragment thereof comprises a heavy chain variable region having the polypeptide sequence of SEQ ID NO:27; and a light chain variable region having the polypeptide sequence of SEQ ID NO:28.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:87, 88, 89, 153, 154, and 155, respectively. In another embodiment, the isolated monoclonal antibody or antigen-binding fragment thereof comprises a heavy chain variable region having a polypeptide sequence at least 85%, preferably 90%, more preferably 95% identical to SEQ ID NO:29, and a light chain variable region having a polypeptide sequence at least 85%, preferably 90%, more preferably 95% identical to SEQ ID NO:30. Preferably, the isolated monoclonal antibody or antigen-binding fragment thereof comprises a heavy chain variable region having the polypeptide sequence of SEQ ID NO:29; and a light chain variable region having the polypeptide sequence of SEQ ID NO:30.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:90, 91, 92, 156, 157, and 158, respectively. In another embodiment, the isolated monoclonal antibody or antigen-binding fragment thereof comprises a heavy chain variable region having a polypeptide sequence at least 85%, preferably 90%, more preferably 95% identical to SEQ ID NO:31, and a light chain variable region having a polypeptide sequence at least 85%, preferably 90%, more preferably 95% identical to SEQ ID NO:32. Preferably, the isolated monoclonal antibody or antigen-binding fragment thereof comprises a heavy chain variable region having the polypeptide sequence of SEQ ID NO:31; and a light chain variable region having the polypeptide sequence of SEQ ID NO:32.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:93, 94, 95, 159, 160, and 161, respectively. In another embodiment, the isolated monoclonal antibody or antigen-binding fragment thereof comprises a heavy chain variable region having a polypeptide sequence at least 85%, preferably 90%, more preferably 95% identical to SEQ ID NO:33, and a light chain variable region having a polypeptide sequence at least 85%, preferably 90%, more preferably 95% identical to SEQ ID NO:34. Preferably, the isolated monoclonal antibody or antigen-binding fragment thereof comprises a heavy chain variable region having the polypeptide sequence of SEQ ID NO:33; and a light chain variable region having the polypeptide sequence of SEQ ID NO:34.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:96, 97, 98, 162, 163, and 164, respectively. In another embodiment, the isolated monoclonal antibody or antigen-binding fragment thereof comprises a heavy chain variable region having a polypeptide sequence at least 85%, preferably 90%, more preferably 95% identical to SEQ ID NO:35, and a light chain variable region having a polypeptide sequence at least 85%, preferably 90%, more preferably 95% identical to SEQ ID NO:36. Preferably, the isolated monoclonal antibody or antigen-binding fragment thereof comprises a heavy chain variable region having the polypeptide sequence of SEQ ID NO:35; and a light chain variable region having the polypeptide sequence of SEQ ID NO:36.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:99, 100, 101, 165, 166, and 167, respectively. In another embodiment, the isolated monoclonal antibody or antigen-binding fragment thereof comprises a heavy chain variable region having a polypeptide sequence at least 85%, preferably 90%, more preferably 95% identical to SEQ ID NO:37, and a light chain variable region having a polypeptide sequence at least 85%, preferably 90%, more preferably 95% identical to SEQ ID NO:38. Preferably, the isolated monoclonal antibody or antigen-binding fragment thereof comprises a heavy chain variable region having the polypeptide sequence of SEQ ID NO:37; and a light chain variable region having the polypeptide sequence of SEQ ID NO:38.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:102, 103, 104, 168, 169, and 170, respectively. In another embodiment, the isolated monoclonal antibody or antigen-binding fragment thereof comprises a heavy chain variable region having a polypeptide sequence at least 85%, preferably 90%, more preferably 95% identical to SEQ ID NO:39, and a light chain variable region having a polypeptide sequence at least 85%, preferably 90%, more preferably 95% identical to SEQ ID NO:40. Preferably, the isolated monoclonal antibody or antigen-binding fragment thereof comprises a heavy chain variable region having the polypeptide sequence of SEQ ID NO:39; and a light chain variable region having the polypeptide sequence of SEQ ID NO:40.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:105, 106, 107, 171, 172, and 173, respectively. In another embodiment, the isolated monoclonal antibody or antigen-binding fragment thereof comprises a heavy chain variable region having a polypeptide sequence at least 85%, preferably 90%, more preferably 95% identical to SEQ ID NO:41, and a light chain variable region having a polypeptide sequence at least 85%, preferably 90%, more preferably 95% identical to SEQ ID NO:42. Preferably, the isolated monoclonal antibody or antigen-binding fragment thereof comprises a heavy chain variable region having the polypeptide sequence of SEQ ID NO:41; and a light chain variable region having the polypeptide sequence of SEQ ID NO:42.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:108, 109, 110, 174, 175, and 176, respectively. In another embodiment, the isolated monoclonal antibody or antigen-binding fragment thereof comprises a heavy chain variable region having a polypeptide sequence at least 85%, preferably 90%, more preferably 95% identical to SEQ ID NO:43, and a light chain variable region having a polypeptide sequence at least 85%, preferably 90%, more preferably 95% identical to SEQ ID NO:44. Preferably, the isolated monoclonal antibody or antigen-binding fragment thereof comprises a heavy chain variable region having the polypeptide sequence of SEQ ID NO:43; and a light chain variable region having the polypeptide sequence of SEQ ID NO:44.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:201, 202, 203, 204, 205, and 206, respectively. In another embodiment, the isolated monoclonal antibody or antigen-binding fragment thereof comprises a heavy chain variable region having a polypeptide sequence at least 85%, preferably 90%, more preferably 95% identical to SEQ ID NO:199, and a light chain variable region having a polypeptide sequence at least 85%, preferably 90%, more preferably 95% identical to SEQ ID NO:200. Preferably, the isolated monoclonal antibody or antigen-binding fragment thereof comprises a heavy chain variable region having the polypeptide sequence of SEQ ID NO:199; and a light chain variable region having the polypeptide sequence of SEQ ID NO:200.

According to another particular aspect, the invention relates to an isolated monoclonal antibody or antigen-binding fragment thereof of the invention, wherein the antibody or antigen-binding fragment thereof is chimeric.

According to another particular aspect, the invention relates to an isolated monoclonal antibody or antigen-binding fragment thereof of the invention, wherein the antibody or antigen-binding fragment thereof is human or humanized.

According to another particular aspect, the invention relates to an isolated humanized monoclonal antibody or antigen-binding fragment thereof, wherein the isolated humanized antibody or antigen-binding fragment thereof comprises:

a. a heavy chain variable region having the polypeptide sequence of SEQ ID NO:183, and a light chain variable region having the polypeptide sequence of SEQ ID NO:191;
  b. a heavy chain variable region having the polypeptide sequence of SEQ ID NO:183, and a light chain variable region having the polypeptide sequence of SEQ ID NO:192;
  c. a heavy chain variable region having the polypeptide sequence of SEQ ID NO:183, and a light chain variable region having the polypeptide sequence of SEQ ID NO:193;
  d. a heavy chain variable region having the polypeptide sequence of SEQ ID NO:184, and a light chain variable region having the polypeptide sequence of SEQ ID NO:190;
  e. a heavy chain variable region having the polypeptide sequence of SEQ ID NO:184, and a light chain variable region having the polypeptide sequence of SEQ ID NO:192;
  f. a heavy chain variable region having the polypeptide sequence of SEQ ID NO:184, and a light chain variable region having the polypeptide sequence of SEQ ID NO:193;
  g. a heavy chain variable region having the polypeptide sequence of SEQ ID NO:185, and a light chain variable region having the polypeptide sequence of SEQ ID NO:190;
  h. a heavy chain variable region having the polypeptide sequence of SEQ ID NO:185, and a light chain variable region having the polypeptide sequence of SEQ ID NO:191;
  i. a heavy chain variable region having the polypeptide sequence of SEQ ID NO:185, and a light chain variable region having the polypeptide sequence of SEQ ID NO:193;
  j. a heavy chain variable region having the polypeptide sequence of SEQ ID NO:185, and a light chain variable region having the polypeptide sequence of SEQ ID NO:198;
  k. a heavy chain variable region having the polypeptide sequence of SEQ ID NO:187, and a light chain variable region having the polypeptide sequence of SEQ ID NO:194;
  l. a heavy chain variable region having the polypeptide sequence of SEQ ID NO:188, and a light chain variable region having the polypeptide sequence of SEQ ID NO:194;
  m. a heavy chain variable region having the polypeptide sequence of SEQ ID NO:188, and a light chain variable region having the polypeptide sequence of SEQ ID NO:196;
  n. a heavy chain variable region having the polypeptide sequence of SEQ ID NO:188, and a light chain variable region having the polypeptide sequence of SEQ ID NO:197; or
  o. a heavy chain variable region having the polypeptide sequence of SEQ ID NO:199, and a light chain variable region having the polypeptide sequence of SEQ ID NO:200.

According to another particular aspect, the invention relates to an isolated monoclonal antibody or antigen-binding fragment thereof, wherein the antibody or antigen-binding fragment thereof is capable of blocking binding of CD47 to thrombospondin-1 (TSP1) and/or to signal regulatory protein alpha (SIRPα).

According to another particular aspect, the invention relates to an isolated monoclonal antibody or antigen-binding fragment thereof, wherein the antibody or antigen-binding fragment thereof is capable of inducing macrophage-mediated phagocytosis of cancer cells.

According to another particular aspect, the invention relates to an isolated monoclonal antibody or antigen-binding fragment thereof, wherein the antibody or antigen-binding fragment thereof is capable of binding cancer cells with minimal to undetectable binding to red blood cells. Binding of cancer cells by the isolated monoclonal antibody or antigen-binding fragment thereof of the invention can be determined using methods known in the art.

In another general aspect, the invention relates to an isolated nucleic acid encoding a monoclonal antibody or antigen-binding fragment thereof of the invention. It will be appreciated by those skilled in the art that the coding sequence of a protein can be changed (e.g., replaced, deleted, inserted, etc.) without changing the amino acid sequence of the protein. Accordingly, it will be understood by those skilled in the art that nucleic acid sequences encoding monoclonal antibodies or antigen-binding fragments thereof of the invention can be altered without changing the amino acid sequences of the proteins.

In another general aspect, the invention relates to a vector comprising an isolated nucleic acid encoding a monoclonal antibody or antigen-binding fragment thereof of the invention. Any vector known to those skilled in the art in view of the present disclosure can be used, such as a plasmid, a cosmid, a phage vector or a viral vector. In some embodiments, the vector is a recombinant expression vector such as a plasmid. The vector can include any element to establish a conventional function of an expression vector, for example, a promoter, ribosome binding element, terminator, enhancer, selection marker, and origin of replication. The promoter can be a constitutive, inducible, or repressible promoter. A number of expression vectors capable of delivering nucleic acids to a cell are known in the art and can be used herein for production of an antibody or antigen-binding fragment thereof in the cell. Conventional cloning techniques or artificial gene synthesis can be used to generate a recombinant expression vector according to embodiments of the invention.

In another general aspect, the invention relates to a host cell comprising an isolated nucleic acid encoding a monoclonal antibody or antigen-binding fragment thereof of the invention. Any host cell known to those skilled in the art in view of the present disclosure can be used for recombinant expression of antibodies or antigen-binding fragments thereof of the invention. In some embodiments, the host cells are E. coli TG1 or BL21 cells (for expression of, e.g., an scFv or Fab antibody), CHO-DG44 or CHO-K1 cells or HEK293 cells (for expression of, e.g., a full-length IgG antibody). According to particular embodiments, the recombinant expression vector is transformed into host cells by conventional methods such as chemical transfection, heat shock, or electroporation, where it is stably integrated into the host cell genome such that the recombinant nucleic acid is effectively expressed.

In another general aspect, the invention relates to a method of producing a monoclonal antibody or antigen-binding fragment thereof of the invention, comprising culturing a cell comprising a nucleic acid encoding the monoclonal antibody or antigen-binding fragment thereof under conditions to produce a monoclonal antibody or antigen-binding fragment thereof of the invention, and recovering the antibody or antigen-binding fragment thereof from the cell or cell culture (e.g., from the supernatant). Expressed antibodies or antigen-binding fragments thereof can be harvested from the cells and purified according to conventional techniques known in the art and as described herein.

Pharmaceutical Compositions

In another general aspect, the invention relates to a pharmaceutical composition, comprising an isolated monoclonal antibody or antigen-binding fragment thereof of the invention and a pharmaceutically acceptable carrier. The term "pharmaceutical composition" as used herein means a product comprising an antibody of the invention together with a pharmaceutically acceptable carrier. Antibodies of the invention and compositions comprising them are also useful in the manufacture of a medicament for therapeutic applications mentioned herein.

As used herein, the term "carrier" refers to any excipient, diluent, filler, salt, buffer, stabilizer, solubilizer, oil, lipid, lipid containing vesicle, microsphere, liposomal encapsulation, or other material well known in the art for use in pharmaceutical formulations. It will be understood that the characteristics of the carrier, excipient or diluent will depend on the route of administration for a particular application. As used herein, the term "pharmaceutically acceptable carrier" refers to a non-toxic material that does not interfere with the effectiveness of a composition according to the invention or the biological activity of a composition according to the invention. According to particular embodiments, in view of the present disclosure, any pharmaceutically acceptable carrier suitable for use in an antibody pharmaceutical composition can be used in the invention.

The formulation of pharmaceutically active ingredients with pharmaceutically acceptable carriers is known in the art, e.g., Remington: The Science and Practice of Pharmacy (e.g. 21st edition (2005), and any later editions). Non-limiting examples of additional ingredients include: buffers, diluents, solvents, tonicity regulating agents, preservatives, stabilizers, and chelating agents. One or more pharmaceutically acceptable carrier may be used in formulating the pharmaceutical compositions of the invention.

In one embodiment of the invention, the pharmaceutical composition is a liquid formulation. A preferred example of a liquid formulation is an aqueous formulation, i.e., a formulation comprising water. The liquid formulation may comprise a solution, a suspension, an emulsion, a microemulsion, a gel, and the like. An aqueous formulation typically comprises at least 50% w/w water, or at least 60%, 70%, 75%, 80%, 85%, 90%, or at least 95% w/w of water.

In one embodiment, the pharmaceutical composition may be formulated as an injectable which can be injected, for example, via an injection device (e.g., a syringe or an infusion pump). The injection may be delivered subcutaneously, intramuscularly, intraperitoneally, intravitreally, or intravenously, for example.

In another embodiment, the pharmaceutical composition is a solid formulation, e.g., a freeze-dried or spray-dried composition, which may be used as is, or whereto the physician or the patient adds solvents, and/or diluents prior to use. Solid dosage forms may include tablets, such as compressed tablets, and/or coated tablets, and capsules (e.g., hard or soft gelatin capsules). The pharmaceutical composition may also be in the form of sachets, dragees, powders, granules, lozenges, or powders for reconstitution, for example.

The dosage forms may be immediate release, in which case they may comprise a water-soluble or dispersible carrier, or they may be delayed release, sustained release, or modified release, in which case they may comprise water-insoluble polymers that regulate the rate of dissolution of the dosage form in the gastrointestinal tract or under the skin.

In other embodiments, the pharmaceutical composition may be delivered intranasally, intrabuccally, or sublingually.

The pH in an aqueous formulation can be between pH 3 and pH 10. In one embodiment of the invention, the pH of the formulation is from about 7.0 to about 9.5. In another embodiment of the invention, the pH of the formulation is from about 3.0 to about 7.0.

In another embodiment of the invention, the pharmaceutical composition comprises a buffer. Non-limiting examples of buffers include: arginine, aspartic acid, bicine, citrate, disodium hydrogen phosphate, fumaric acid, glycine, glycylglycine, histidine, lysine, maleic acid, malic acid, sodium acetate, sodium carbonate, sodium dihydrogen phosphate, sodium phosphate, succinate, tartaric acid, tricine, and tris(hydroxymethyl)-aminomethane, and mixtures thereof. The buffer may be present individually or in the aggregate, in a concentration from about 0.01 mg/ml to about 50 mg/ml, for example from about 0.1 mg/ml to about 20 mg/ml. Pharmaceutical compositions comprising each one of these specific buffers constitute alternative embodiments of the invention.

In another embodiment of the invention, the pharmaceutical composition comprises a preservative. Non-limiting examples of preservatives include: benzethonium chloride, benzoic acid, benzyl alcohol, bronopol, butyl 4-hydroxybenzoate, chlorobutanol, chlorocresol, chlorhexidine, chlorphenesin, o-cresol, m-cresol, p-cresol, ethyl 4-hydroxybenzoate, imidurea, methyl 4-hydroxybenzoate, phenol, 2-phenoxyethanol, 2-phenylethanol, propyl 4-hydroxybenzoate, sodium dehydroacetate, thiomerosal, and mixtures thereof. The preservative may be present individually or in the aggregate, in a concentration from about 0.01 mg/ml to about 50 mg/ml, for example from about 0.1 mg/ml to about 20 mg/ml. Pharmaceutical compositions comprising each one of these specific preservatives constitute alternative embodiments of the invention.

In another embodiment of the invention, the pharmaceutical composition comprises an isotonic agent. Non-limiting examples of the embodiment include a salt (such as sodium chloride), an amino acid (such as glycine, histidine, arginine, lysine, isoleucine, aspartic acid, tryptophan, and threonine), an alditol (such as glycerol, 1,2-propanediol propyleneglycol), 1,3-propanediol, and 1,3-butanediol), polyethyleneglycol (e.g. PEG400), and mixtures thereof. Another example of an isotonic agent includes a sugar. Non-limiting examples of sugars may be mono-, di-, or polysaccharides, or water-soluble glucans, including for example fructose, glucose, mannose, sorbose, xylose, maltose, lactose, sucrose, trehalose, dextran, pullulan, dextrin, cyclodextrin, alpha and beta-HPCD, soluble starch, hydroxyethyl starch, and sodium carboxymethylcellulose. Another example of an isotonic agent is a sugar alcohol, wherein the term "sugar alcohol" is defined as a C(4-8) hydrocarbon having at least one —OH group. Non-limiting examples of sugar alcohols include mannitol, sorbitol, inositol, galactitol, dulcitol, xylitol, and arabitol. Pharmaceutical compositions comprising each isotonic agent listed in this paragraph constitute alternative embodiments of the invention. The isotonic agent may be present individually or in the aggregate, in a concentration from about 0.01 mg/ml to about 50 mg/ml, for example from about 0.1 mg/ml to about 20 mg/ml. Pharmaceutical compositions comprising each one of these specific isotonic agents constitute alternative embodiments of the invention.

In another embodiment of the invention, the pharmaceutical composition comprises a chelating agent. Non-limiting examples of chelating agents include citric acid, aspartic acid, salts of ethylenediaminetetraacetic acid (EDTA), and mixtures thereof. The chelating agent may be present individually or in the aggregate, in a concentration from about 0.01 mg/ml to about 50 mg/ml, for example from about 0.1 mg/ml to about 20 mg/ml. Pharmaceutical compositions comprising each one of these specific chelating agents constitute alternative embodiments of the invention.

In another embodiment of the invention, the pharmaceutical composition comprises a stabilizer. Non-limiting examples of stabilizers include one or more aggregation inhibitors, one or more oxidation inhibitors, one or more surfactants, and/or one or more protease inhibitors.

In another embodiment of the invention, the pharmaceutical composition comprises a stabilizer, wherein said stabilizer is carboxy-/hydroxycellulose and derivates thereof (such as HPC, HPC-SL, HPC-L and HPMC), cyclodextrins, 2-methylthioethanol, polyethylene glycol (such as PEG 3350), polyvinyl alcohol (PVA), polyvinyl pyrrolidone, salts (such as sodium chloride), sulphur-containing substances such as monothioglycerol), or thioglycolic acid. The stabilizer may be present individually or in the aggregate, in a concentration from about 0.01 mg/ml to about 50 mg/ml, for example from about 0.1 mg/ml to about 20 mg/ml. Pharmaceutical compositions comprising each one of these specific stabilizers constitute alternative embodiments of the invention.

In further embodiments of the invention, the pharmaceutical composition comprises one or more surfactants, preferably a surfactant, at least one surfactant, or two different surfactants. The term "surfactant" refers to any molecules or ions that are comprised of a water-soluble (hydrophilic) part, and a fat-soluble (lipophilic) part. The surfactant may, for example, be selected from the group consisting of anionic surfactants, cationic surfactants, nonionic surfactants, and/or zwitterionic surfactants. The surfactant may be present individually or in the aggregate, in a concentration from about 0.1 mg/ml to about 20 mg/ml. Pharmaceutical compositions comprising each one of these specific surfactants constitute alternative embodiments of the invention.

In a further embodiment of the invention, the pharmaceutical composition comprises one or more protease inhibitors, such as, e.g., EDTA, and/or benzamidine hydrochloric acid (HCl). The protease inhibitor may be present individually or in the aggregate, in a concentration from about 0.1 mg/ml to about 20 mg/ml. Pharmaceutical compositions comprising each one of these specific protease inhibitors constitute alternative embodiments of the invention.

In another general aspect, the invention relates to a method of producing a pharmaceutical composition comprising a monoclonal antibody or antigen-binding fragment thereof of the invention, comprising combining a monoclonal antibody or antigen-binding fragment thereof with a pharmaceutically acceptable carrier to obtain the pharmaceutical composition.

Methods of Use

In another general aspect, the invention relates to a method of blocking the binding of CD47 to thrombospondin-1 (TSP1), or a method of blocking the binding of CD47 to signal regulatory protein alpha (SIRPα), the method comprising administering to the subject a pharmaceutical composition of the invention.

The functional activity of antibodies and antigen-binding fragments thereof that bind CD47 can be characterized by methods known in the art and as described herein. Methods for characterizing antibodies and antigen-binding fragments thereof that bind CD47 include, but are not limited to, affinity and specificity assays including Biacore, ELISA, and OctetRed analysis; receptor ligand binding assays to detect blocking of the binding of CD47 to TSP1 and/or SIRPα; phagocytosis assays where CD47-expressing cells are fluorescently labeled and incubated with macrophages to detect the effect of blocking CD47 binding to SIRPα on the phagocytosis of the CD47-expressing cells by macrophages; hemagglutination assays to detect the effect of anti-CD47 on red blood cells, and cell-based assays to detect the effect of blocking the TSP1-CD47 interaction on downstream eNOS/NO/cGMP signaling in endothelial cells. According to particular embodiments, the methods for characterizing antibodies and antigen-binding fragments thereof that bind CD47 include those described below.

In another general aspect, the invention relates to a method of treating a cancer in a subject in need thereof, comprising administering to the subject a pharmaceutical composition of the invention. The cancer can be any liquid or solid cancer, for example, it can be selected from but not limited to, a lung cancer, a gastric cancer, a colon cancer, a hepatocellular carcinoma, a renal cell carcinoma, a bladder urothelial carcinoma, a metastatic melanoma, a breast cancer, an ovarian cancer, a cervical cancer, a head and neck cancer, a pancreatic cancer, a glioma, a glioblastoma, and other solid tumors, and a non-Hodgkin's lymphoma (NHL), an acute lympocytic leukemia (ALL), a chronic lymphocytic leukemia (CLL), a chronic myelogenous leukemia (CIVIL), a multiple myeloma (MM), an acute myeloid leukemia (AML), and other liquid tumors.

In another general aspect, the invention relates to a method of treating an inflammatory disease in a subject in need thereof, comprising administering to the subject a pharmaceutical composition of the invention.

In another general aspect, the invention relates to a method of treating an infectious disease in a subject in need thereof, comprising administering to the subject a pharmaceutical composition of the invention.

In another general aspect, the invention relates to a method of treating atherosclerosis in a subject in need thereof, comprising administering to the subject a pharmaceutical composition of the invention.

In another general aspect, the invention relates to a method of treating a cardiovascular disease in a subject in need thereof, comprising administering to the subject a pharmaceutical composition of the invention.

In another general aspect, the invention relates to a method of treating a metabolic disease in a subject in need thereof, comprising administering to the subject a pharmaceutical composition of the invention.

In another general aspect, the invention relates to a method of a radiation-induced injury in a subject in need thereof, comprising administering to the subject a pharmaceutical composition of the invention.

In another general aspect, the invention relates to a method of treating an autoimmune disease in a subject in need thereof, comprising administering to the subject a pharmaceutical composition of the invention.

According to embodiments of the invention, the pharmaceutical composition comprises a therapeutically effective amount of the anti-CD47 antibody or antigen-binding fragment thereof. As used herein, the term "therapeutically effective amount" refers to an amount of an active ingredient or component that elicits the desired biological or medicinal response in a subject. A therapeutically effective amount can be determined empirically and in a routine manner, in relation to the stated purpose.

As used herein with reference to anti-CD47 antibodies or antigen-binding fragments thereof, a therapeutically effective amount means an amount of the anti-CD47 antibody or antigen-binding fragment thereof that modulates an immune response in a subject in need thereof. Also as used herein with reference to anti-CD47 antibodies or antigen-binding fragments thereof, a therapeutically effective amount means an amount of the anti-CD47 antibody or antigen-binding fragment thereof that results in treatment of a disease, disorder, or condition; prevents or slows the progression of the disease, disorder, or condition; or reduces or completely alleviates symptoms associated with the disease, disorder, or condition.

According to particular embodiments, the disease, disorder or condition to be treated is cancer, preferably a cancer selected from the group consisting of lung cancer, gastric cancer, colon cancer, hepatocellular carcinoma, renal cell carcinoma, bladder urothelial carcinoma, metastatic melanoma, breast cancer, ovarian cancer, cervical cancer, head and neck cancer, pancreatic cancer, glioma, glioblastoma, and other solid tumors, and non-Hodgkin's lymphoma (NHL), acute lymphocytic leukemia (ALL), chronic lymphocytic leukemia (CLL), chronic myelogenous leukemia (CML), multiple myeloma (MM), acute myeloid leukemia (AML), and other liquid tumors. According to other particular embodiments, the disease, disorder or condition to be treated is an inflammatory disease, an infectious disease, atherosclerosis, cardiovascular disease, metabolic diseases, radiation-induced injury, an immune disease, and/or an autoimmune disease.

According to particular embodiments, a therapeutically effective amount refers to the amount of therapy which is sufficient to achieve one, two, three, four, or more of the following effects: (i) reduce or ameliorate the severity of the disease, disorder or condition to be treated or a symptom associated therewith; (ii) reduce the duration of the disease, disorder or condition to be treated, or a symptom associated therewith; (iii) prevent the progression of the disease, disorder or condition to be treated, or a symptom associated therewith; (iv) cause regression of the disease, disorder or condition to be treated, or a symptom associated therewith; (v) prevent the development or onset of the disease, disorder or condition to be treated, or a symptom associated therewith; (vi) prevent the recurrence of the disease, disorder or condition to be treated, or a symptom associated therewith; (vii) reduce hospitalization of a subject having the disease, disorder or condition to be treated, or a symptom associated therewith; (viii) reduce hospitalization length of a subject having the disease, disorder or condition to be treated, or a symptom associated therewith; (ix) increase the survival of a subject with the disease, disorder or condition to be treated, or a symptom associated therewith; (xi) inhibit or reduce the disease, disorder or condition to be treated, or a symptom associated therewith in a subject; and/or (xii) enhance or improve the prophylactic or therapeutic effect(s) of another therapy.

The therapeutically effective amount or dosage can vary according to various factors, such as the disease, disorder or condition to be treated, the means of administration, the target site, the physiological state of the subject (including, e.g., age, body weight, health), whether the subject is a human or an animal, other medications administered, and whether the treatment is prophylactic or therapeutic. Treatment dosages are optimally titrated to optimize safety and efficacy.

According to particular embodiments, the compositions described herein are formulated to be suitable for the intended route of administration to a subject. For example, the compositions described herein can be formulated to be suitable for intravenous, subcutaneous, or intramuscular administration.

As used herein, the terms "treat," "treating," and "treatment" are all intended to refer to an amelioration or reversal of at least one measurable physical parameter related to a cancer, an immune disease, disorder or condition, an autoimmune disease, disorder or condition, or an inflammatory disease, disorder or condition, an infectious disease, disorder or condition, an atherosclerosis, disorder or condition, a cardiovascular disease, disorder or condition, a metabolic disease disorder or condition, a radiation-induced injury, disorder or condition, which is not necessarily discernible in the subject, but can be discernible in the subject. The terms "treat," "treating," and "treatment," can also refer to causing regression, preventing the progression, or at least slowing down the progression of the disease, disorder, or condition. In a particular embodiment, "treat," "treating," and "treatment" refer to an alleviation, prevention of the development or onset, or reduction in the duration of one or more symptoms associated with the disease, disorder, or condition, such as a tumor or more preferably a cancer. In a particular embodiment, "treat," "treating," and "treatment" refer to prevention of the recurrence of the disease, disorder, or condition. In a particular embodiment, "treat," "treating," and "treatment" refer to an increase in the survival of a subject having the disease, disorder, or condition. In a particular embodiment, "treat," "treating," and "treatment" refer to elimination of the disease, disorder, or condition in the subject.

According to particular embodiments, a composition used in the treatment of a cancer, an immune disease, disorder or condition, an autoimmune disease, disorder or condition, an inflammatory disease, disorder or condition, an infectious disease, disorder or condition, an atherosclerosis, disorder or condition, a cardiovascular disease, disorder or condition, a metabolic disease, disorder or condition, a radiation-induced injury, disorder or condition, can be used in combination with another treatment. For cancer treatment, the composition can be used in combination with another treatment including, but not limited to, a chemotherapy, an anti-CD20 mAb, an anti-CTLA-4 antibody, an anti-LAG-3 mAb, an anti-EGFR mAb, an anti-HER-2 mAb, an anti-CD19 mAb, an anti-CD33 mAb, an anti-CD73 mAb, an anti-CD47 mAb, an anti-DLL-3 mAb, an anti-apelin mAb, an anti-TIP-1 mAb, an anti-CLDN18.2 mAb, an anti-FOLR1 mAb, an anti-PD-L1 antibody, an anti-PD-1 antibody, a PD-1/PD-L1 therapy, or other immuno-oncology drug, a targeted therapy, an antiangiogenic agent, a radiation therapy, or other anticancer drugs. Anti-CD47 antibodies can be used to construct bispecific antibodies with partner mAbs against PD-1, PD-L1, LAG3, TIM-3, CTLA-4, EGFR, HER-2, CD19, CD20, CD33, CD73, apelin, DLL3, claudin18.2, TIP-1, CD3, folate receptor alpha and/or other tumor surface antigens to treat cancers/tumors that express both CD47 and the specific tumor associated antigen.

As used herein, the term "in combination," in the context of the administration of two or more therapies to a subject, refers to the use of more than one therapy. The use of the term "in combination" does not restrict the order in which therapies are administered to a subject. For example, a first therapy (e.g., a composition described herein) can be administered prior to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy to a subject.

In another general aspect, the invention relates to a method of determining a level of CD47 in a subject. The methods comprise (a) obtaining a sample from the subject; (b) contacting the sample with an antibody or antigen-binding fragment thereof of the invention; and (c) determining a level of CD47 in the subject.

As used herein, "sample" refers to a biological sample isolated from a subject and can include, but is not limited to, whole blood, serum, plasma, blood cells, endothelial cells, tissue biopsies (e.g., a cancer tissue, a hepatic tissue, etc.), lymphatic fluid, ascites fluid, interstitial fluid, bone marrow, cerebrospinal fluid, saliva, mucous, sputum, sweat, urine, or any other secretion, excretion, or other bodily fluids. A "blood sample" refers to whole blood or any fraction thereof, including blood cells, serum, and plasma. A "blood sample" can, for example, comprise cancer cells.

In certain embodiments, the level of CD47 in the subject can be determined utilizing assays selected from, but not limited to, a Western blot assay, an ELISA assay, a FACS assay, and/or an immunohistochemistry (IHC). Relative protein levels can be determined by utilizing Western blot analysis, FACS assay, and immunohistochemistry (IHC), and absolute protein levels can be determined by utilizing an ELISA assay. When determining the relative levels of CD47, the levels of CD47 can be determined between at least two samples, e.g., between samples from the same subject at different time points, between samples from different tissues in the same subject, and/or between samples from different subjects. Alternatively, when determining absolute levels of CD47, such as by an ELISA assay, the absolute level of CD47 in the sample can be determined by creating a standard for the ELISA assay prior to testing the sample. A person skilled in the art would understand which analytical techniques to utilize to determine the level of CD47 in a sample from the subject utilizing the antibodies or antigen-binding fragments thereof of the invention.

Utilizing methods of determining a level of CD47 in a sample from a subject can lead to the diagnosis of abnormal (elevated, reduced, or insufficient) CD47 levels in a disease and making appropriate therapeutic decisions. Such a disease can be selected from, but not limited to, a cancer, preferably a cancer selected from the group consisting of lung cancer, gastric cancer, colon cancer, hepatocellular carcinoma, renal cell carcinoma, bladder urothelial carcinoma, metastatic melanoma, breast cancer, ovarian cancer, cervical cancer, head and neck cancer, pancreatic cancer, glioma, glioblastoma, and other solid tumors, and non-Hodgkin's lymphoma (NHL), acute lymphocytic leukemia (ALL), chronic lymphocytic leukemia (CLL), chronic myelogenous leukemia (CML), multiple myeloma (MM), acute myeloid leukemia (AML), and other liquid tumors, an inflammatory disease, an infectious disease, atherosclerosis, cardiovascular disease, metabolic diseases, radiation-induced injury, an immune disease, and/or an autoimmune disease.

Embodiments

The invention provides also the following non-limiting embodiments.

Embodiment 1 is an isolated monoclonal antibody or antigen-binding fragment thereof comprising a heavy chain complementarity determining region 1 (HCDR1), HCDR2, HCDR3, a light chain complementarity determining region 1 (LCDR1), LCDR2, and LCDR3, having the polypeptide sequences of:

(1) SEQ ID NOs:177, 46, 47, 178, 112, and 179, respectively;
(2) SEQ ID NOs:51, 52, 53, 117, 118, and 119, respectively;
(3) SEQ ID NOs:54, 55, 56, 120, 121, and 122, respectively;
(4) SEQ ID NOs:57, 58, 59, 123, 124, and 125, respectively;
(5) SEQ ID NOs:60, 61, 62, 126, 127, and 128, respectively;
(6) SEQ ID NOs:180, 181, 182, 129, 130, and 131, respectively;
(7) SEQ ID NOs:72, 73, 74, 138, 139, and 140, respectively;
(8) SEQ ID NOs:78, 79, 80, 144, 145, and 146, respectively;
(9) SEQ ID NOs:81, 82, 83, 147, 148, and 149, respectively;
(10) SEQ ID NOs:84, 85, 86, 150, 151, and 152, respectively;
(11) SEQ ID NOs:87, 88, 89, 153, 154, and 155, respectively;

(12) SEQ ID NOs:90, 91, 92, 156, 157, and 158, respectively;
(13) SEQ ID NOs:93, 94, 95, 159, 160, and 161, respectively;
(14) SEQ ID NOs:96, 97, 98, 162, 163, and 164, respectively;
(15) SEQ ID NOs:99, 100, 101, 165, 166, and 167, respectively;
(16) SEQ ID NOs:102, 103, 104, 168, 169, and 170, respectively;
(17) SEQ ID NOs:105, 106, 107, 171, 172, and 173, respectively;
(18) SEQ ID NOs:108, 109, 110, 174, 175, and 176, respectively; or
(19) SEQ ID NOs:201, 202, 203, 204, 205, and 206, respectively wherein the antibody or antigen-binding fragment thereof specifically binds CD47, preferably human CD47.

Embodiment 2 is the isolated monoclonal antibody or antigen-binding fragment of embodiment 1, comprising a heavy chain variable region having a polypeptide sequence at least 95% identical to SEQ ID NO:1, 3, 5, 7, 9, 11, 13, 15, 17, 19, 21, 23, 25, 27, 29, 31, 33, 35, 37, 39, 41, or 43, or a light chain variable region having a polypeptide sequence at least 95% identical to SEQ ID NO:2, 4, 6, 8, 10, 12, 14, 16, 18, 20, 22, 24, 26, 28, 30, 32, 34, 36, 38, 40, 42, or 44.

Embodiment 3 is the isolated monoclonal antibody or antigen-binding fragment of embodiment 1 or 2, comprising
(a) a heavy chain variable region having the polypeptide sequence of SEQ ID NO:1, and a light chain variable region having the polypeptide sequence of SEQ ID NO:2;
(b) a heavy chain variable region having the polypeptide sequence of SEQ ID NO:3, and a light chain variable region having the polypeptide sequence of SEQ ID NO:4;
(c) a heavy chain variable region having the polypeptide sequence of SEQ ID NO:5, and a light chain variable region having the polypeptide sequence of SEQ ID NO:6;
(d) a heavy chain variable region having the polypeptide sequence of SEQ ID NO:7, and a light chain variable region having the polypeptide sequence of SEQ ID NO:8;
(e) a heavy chain variable region having the polypeptide sequence of SEQ ID NO:9, and a light chain variable region having the polypeptide sequence of SEQ ID NO:10;
(f) a heavy chain variable region having the polypeptide sequence of SEQ ID NO:11, and a light chain variable region having the polypeptide sequence of SEQ ID NO:12;
(g) a heavy chain variable region having the polypeptide sequence of SEQ ID NO:13, and a light chain variable region having the polypeptide sequence of SEQ ID NO:14;
(h) a heavy chain variable region having the polypeptide sequence of SEQ ID NO:15, and a light chain variable region having the polypeptide sequence of SEQ ID NO:16;
(i) a heavy chain variable region having the polypeptide sequence of SEQ ID NO:17, and a light chain variable region having the polypeptide sequence of SEQ ID NO:18;
(j) a heavy chain variable region having the polypeptide sequence of SEQ ID NO:19, and a light chain variable region having the polypeptide sequence of SEQ ID NO:20;
(k) a heavy chain variable region having the polypeptide sequence of SEQ ID NO:21, and a light chain variable region having the polypeptide sequence of SEQ ID NO:22;
(l) a heavy chain variable region having the polypeptide sequence of SEQ ID NO:23, and a light chain variable region having the polypeptide sequence of SEQ ID NO:24;
(m) a heavy chain variable region having the polypeptide sequence of SEQ ID NO:25, and a light chain variable region having the polypeptide sequence of SEQ ID NO:26;
(n) a heavy chain variable region having the polypeptide sequence of SEQ ID NO:27, and a light chain variable region having the polypeptide sequence of SEQ ID NO:28;
(o) a heavy chain variable region having the polypeptide sequence of SEQ ID NO:29, and a light chain variable region having the polypeptide sequence of SEQ ID NO:30;
(p) a heavy chain variable region having the polypeptide sequence of SEQ ID NO:31, and a light chain variable region having the polypeptide sequence of SEQ ID NO:32;
(q) a heavy chain variable region having the polypeptide sequence of SEQ ID NO:33, and a light chain variable region having the polypeptide sequence of SEQ ID NO:34;
(r) a heavy chain variable region having the polypeptide sequence of SEQ ID NO:35, and a light chain variable region having the polypeptide sequence of SEQ ID NO:36;
(s) a heavy chain variable region having the polypeptide sequence of SEQ ID NO:37, and a light chain variable region having the polypeptide sequence of SEQ ID NO:38;
(t) a heavy chain variable region having the polypeptide sequence of SEQ ID NO:39, and a light chain variable region having the polypeptide sequence of SEQ ID NO:40;
(u) a heavy chain variable region having the polypeptide sequence of SEQ ID NO:41, and a light chain variable region having the polypeptide sequence of SEQ ID NO:42; or
(v) a heavy chain variable region having the polypeptide sequence of SEQ ID NO:43, and a light chain variable region having the polypeptide sequence of SEQ ID NO:44.

Embodiment 4 is the isolated monoclonal antibody or antigen-binding fragment of any one of embodiments 1 to 3, wherein the antibody or antigen-binding fragment thereof inhibits the interaction of CD47 and thrombospondin-1 (TSP-1) and/or CD47 and SIRPα.

Embodiment 5 is the isolated monoclonal antibody or antigen-binding fragment of any one of embodiments 1 to 4, wherein the antibody or antigen-binding fragment thereof is chimeric.

Embodiment 6 is the isolated monoclonal antibody or antigen-binding fragment of any one of embodiments 1 to 5, wherein the antibody or antigen-binding fragment thereof is human or humanized.

Embodiment 7 is the isolated monoclonal antibody or antigen-binding fragment thereof of embodiment 6, wherein the antibody or antigen-binding fragment thereof comprises:
a. a heavy chain variable region having the polypeptide sequence of SEQ ID NO:183, and a light chain variable region having the polypeptide sequence of SEQ ID NO:191;
b. a heavy chain variable region having the polypeptide sequence of SEQ ID NO:183, and a light chain variable region having the polypeptide sequence of SEQ ID NO:192;
c. a heavy chain variable region having the polypeptide sequence of SEQ ID NO:183, and a light chain variable region having the polypeptide sequence of SEQ ID NO:193;
d. a heavy chain variable region having the polypeptide sequence of SEQ ID NO:184, and a light chain variable region having the polypeptide sequence of SEQ ID NO:190;
e. a heavy chain variable region having the polypeptide sequence of SEQ ID NO:184, and a light chain variable region having the polypeptide sequence of SEQ ID NO:192;
f. a heavy chain variable region having the polypeptide sequence of SEQ ID NO:184, and a light chain variable region having the polypeptide sequence of SEQ ID NO:193;
g. a heavy chain variable region having the polypeptide sequence of SEQ ID NO:185, and a light chain variable region having the polypeptide sequence of SEQ ID NO:190;
h. a heavy chain variable region having the polypeptide sequence of SEQ ID NO:185, and a light chain variable region having the polypeptide sequence of SEQ ID NO:191;
i. a heavy chain variable region having the polypeptide sequence of SEQ ID NO:185, and a light chain variable region having the polypeptide sequence of SEQ ID NO:193;
j. a heavy chain variable region having the polypeptide sequence of SEQ ID NO:185, and a light chain variable region having the polypeptide sequence of SEQ ID NO:198;
k. a heavy chain variable region having the polypeptide sequence of SEQ ID NO:187, and a light chain variable region having the polypeptide sequence of SEQ ID NO:194;
l. a heavy chain variable region having the polypeptide sequence of SEQ ID NO:188, and a light chain variable region having the polypeptide sequence of SEQ ID NO:194;
m. a heavy chain variable region having the polypeptide sequence of SEQ ID NO:188, and a light chain variable region having the polypeptide sequence of SEQ ID NO:196;
n. a heavy chain variable region having the polypeptide sequence of SEQ ID NO:188, and a light chain variable region having the polypeptide sequence of SEQ ID NO:197; or
o. a heavy chain variable region having the polypeptide sequence of SEQ ID NO:199, and a light chain variable region having the polypeptide sequence of SEQ ID NO:200.

Embodiment 8 is the isolated monoclonal antibody or antigen-binding fragment of any one of embodiments 1 to 7, wherein the antibody or antigen-binding fragment thereof is capable of blocking binding of CD47 to thrombospondin-1 (TSP1) and/or to signal regulatory protein alpha (SIRPα).

Embodiment 9 is the isolated monoclonal antibody or antigen-binding fragment of any one of embodiments 1 to 7, wherein the antibody or antigen-binding fragment thereof is capable of inducing macrophage-mediated phagocytosis of cancer cells.

Embodiment 10 is the isolated monoclonal antibody or antigen-binding fragment of any one of embodiments 1 to 7, wherein the antibody or antigen-binding fragment thereof is capable of binding cancer cells with minimal to undetectable binding to red blood cells.

Embodiment 11 is an isolated nucleic acid encoding the monoclonal antibody or antigen-binding fragment of any one of embodiments 1 to 10.

Embodiment 12 is a vector comprising the isolated nucleic acid of embodiment 11.

Embodiment 13 is a host cell comprising the vector of embodiment 12.

Embodiment 14 is a pharmaceutical composition, comprising the isolated monoclonal antibody or antigen-binding fragment of any one of embodiments 1 to 10 and a pharmaceutically acceptable carrier.

Embodiment 15 is a method of blocking binding of CD47 to thrombospondin-1 (TSP1) in a subject in need thereof, comprising administering to the subject the pharmaceutical composition of embodiment 14.

Embodiment 16 is a method of blocking binding of CD47 to signal regulatory protein alpha (SIRPα) in a subject in need thereof, comprising administering to the subject the pharmaceutical composition of embodiment 14.

Embodiment 17 is a method of treating cancer in a subject in need thereof, comprising administering to the subject the pharmaceutical composition of embodiment 14.

Embodiment 18 is a method of treating an inflammatory disease in a subject in need thereof, comprising administering to the subject the pharmaceutical composition of embodiment 14.

Embodiment 19 is a method of treating an infectious disease in a subject in need thereof, comprising administering to the subject the pharmaceutical composition of embodiment 14.

Embodiment 20 is a method of treating atherosclerosis in a subject in need thereof, comprising administering to the subject the pharmaceutical composition of embodiment 14.

Embodiment 21 is a method of treating a cardiovascular disease in a subject in need thereof, comprising administering to the subject the pharmaceutical composition of embodiment 14.

Embodiment 22 is a method of treating a metabolic disease in a subject in need thereof, comprising administering to the subject the pharmaceutical composition of embodiment 14.

Embodiment 23 is a method of treating a radiation-induced injury in a subject in need thereof, comprising administering to the subject the pharmaceutical composition of embodiment 14.

Embodiment 24 is a method of treating an autoimmune disease in a subject in need thereof, comprising administering to the subject the pharmaceutical composition of embodiment 14.

Embodiment 25 is a method of determining a level of CD47 in a subject, the method comprising (a) obtaining a sample from the subject; (b) contacting the sample with an antibody or antigen-binding fragment of any one of embodiments 1 to 10; and (c) determining a level of CD47 in the subject.

Embodiment 26 is the method of embodiment 25, wherein the sample is a tissue sample.

Embodiment 27 is the method of embodiment 26, wherein the tissue sample is a cancer tissue sample.

Embodiment 28 is the method of embodiment 25, wherein the sample is a blood sample.

Embodiment 29 is a method of producing the monoclonal antibody or antigen-binding fragment of any one of embodiments 1 to 10, comprising culturing a cell comprising a nucleic acid encoding the monoclonal antibody or antigen-binding fragment under conditions to produce the monoclonal antibody or antigen-binding fragment, and recovering the antibody or antigen-binding fragment from the cell or culture.

Embodiment 30 is a method of producing a pharmaceutical composition comprising the monoclonal antibody or antigen-binding fragment of any one of embodiments 1 to 10, comprising combining the monoclonal antibody or antigen-binding fragment with a pharmaceutically acceptable carrier to obtain the pharmaceutical composition.

EXAMPLES

Example 1

Identification of Anti-CD47 Monoclonal Antibodies

Anti-CD47 monoclonal antibodies (mAbs) were generated from mice immunized with recombinant human and cynomolgus CD47-HIS. Briefly, after the immunization, the titer of antibodies in the serum was estimated by ELISA using huCD47-HIS and cyCD47-HIS coated plates. B-cells were harvested and fused with a myeloma cell line to produce hybridomas. Hybridomas were plated into 20×384 well plates and the supernatants from each well were screened by ELISA for their binding towards both human and cynomolgus CD47. 400 hybridomas were expanded and were further analyzed for binding to RAJI cells by FACS, blocking CD47/SIRPα interaction, binding kinetics to recombinant huCD47 on an Octet, and tested for hemagglutination activity with human blood. Top positive hybridomas were then cloned by plating parental hybridomas at 1 cell per well in 384 well plates and screening clonal supernatants by ELISA for binding to huCD47. Heavy chain and light chain variable regions from clonal hybridomas were amplified by 5' RACE and sequenced. The supernatants of these clones from scale-up culture were used to purify antibodies with protein A for further characterization.

The sequences of heavy and light chain variable regions for anti-CD47 monoclonal antibodies are provided in Tables 1 and 2, respectively, and the CDR regions for the anti-CD47 monoclonal antibodies are provided in Tables 3 and 4. The CDR regions for the anti-CD47 monoclonal antibodies were determined utilizing the IMGT method.

TABLE 1

| Sequences of heavy chain variable regions for anti-CD47 monoclonal antibodies (mAbs) | |
|---|---|
| mAb clones | VH |
| 9023A | QIQLQQSGPELVRPGASVKISCKASGYTFTDYYINWVKQRPGQGLEWIGWIYPG SGNTKYNEKFKGKATLTVDSSSSTAYMQLSSLTSEDSAVYFCARRGPWYFDVW GAGTTVTVSS (SEQ ID NO: 1) |
| 14P6A | QIQLQQSGPELVRPGASVKISCKASGYTFTAYYINWVKQRPGQGLEWIGWIYPG SGNTKYNEKFKGKATLTVDTSSSTAYIQLSSLTSEDSAVYFCARRGPWYFDVWG AGTTVTVSS (SEQ ID NO: 3) |
| 4M8A | QVQLQQPGAELVKPGASVKLSCKTSGYTFTSYWIHWVNQRPGQGLEWIGNIDPS DSETHYNPKFKDKATLTVDKSSSTAYMQLSSLTSEDSAVYYCARWGGWLPLDY WGQGTTLTVSS (SEQ ID NO: 5) |
| 16M17A | QVQLQQPGAELVKPGASVKLSCKASGYTFTNYWMHWVKQRPGQGLEWIGNID PSDSETHYNQKFKDKATLTVDKSSSTAYMQLSSLTSEDSAVYYCARMAFITTVV DYWGQGTTLTVSS (SEQ ID NO: 7) |
| 13C4A | QVQLQQPGAELVKPGASVKLSCKASGYTFTSYWMHWVKQRPGQGLEWIGNID PSDSETHYNQKFKDKATLTVDKSSSTAYMQLSSLTSEDSAVYYCARWGYYGRS PLDHWGQGTTLTVSS (SEQ ID NO: 9) |
| 14O18A | QVQLQQPGAELVKPGASVKLSCKASGYTFTSYWMHWVKQRPGQGLEWIGNID PSDSETHYNQKFKDKATLTLDKSSSTAYMQLSSLTSEDSAVYYCARWYYGGSG AMDYWGQGTSVTVSS (SEQ ID NO: 11) |
| 5D24A | QVQLQQPGAELVKPGASVKLSCKASGYTFTSSWMHWVKQRPGQGLEWIGNIDP SDSETHYNQKFKDKATLTVDKSSSTAYMQLSSLTSEDSAVYYCARWGYYGKSA IDYWGQGTSVTVSS (SEQ ID NO: 13) |
| 11G2A | QVQLQQPGAELVKPGASVKLSCKASGYTFTSYWMHWVKQRPGQGLEWIGNID PSDSEAHYNQKFRDKATLTVDKSSSTAYMQLSSLTSEDSAVYYCARWGYYGKS AMDYWGQGTSVTVSS (SEQ ID NO: 15) |
| 13B18A | QVQLQQPGAELVKPGASVKLSCKASGYTFTSYWMHWVKQRPGQGLEWIGNID PSDSETHYNQKFKDKATLTVDKSSSTAYMQLSSLTSEDSAVYYCSRWGYYGKS AMDYWGQGTSVTVSS (SEQ ID NO: 17) |
| 1J7A | QVQLQQPGAELVKPGASVKLSCKASGYTFTSYWMHWVKQRPGQGLEWIGNID PSDSETHYNQKFRDKATLTVDKSSNTAYMQLSSLTSEDSAVYYCARWGLRGAM DYWGQGTSVTVS (SEQ ID NO: 19) |

TABLE 1-continued

Sequences of heavy chain variable regions for anti-CD47 monoclonal antibodies (mAbs)

| mAb clones | VH |
|---|---|
| 14D18A | QVQLQQPGAELVKPGASVKLSCKASGYTFTSYWMHWVKQRPGQGLEWIGNID PSDSETHYNQKFKDKATLTVDKSSSTAYMQLSSLTSEDSAVYYCARWGYYGRS PLDHWGQGTTLTVSS (SEQ ID NO: 21) |
| 30S A | EVKLVESGGGLVQSGRSLRLSCATSGFTFSDFYMEWVRQAPGKGLEWIAASRN KANDYTTEYSASVKGRFIVSRDTSQSILYLQMNALRAEDTAIYYCARDTAYWG QGTLVTVSA (SEQ ID NO: 23) |
| 17C6A | QVQLQQPGAELVKPGASVKLSCKASGYTFTSYWMHWVKQRPGQGLEWIGNID PSDSETHYNQKFKDKATLTVDKSSSTAHMQLSSLTSEDSAVYYCAGTDLAYWG QGTLVTVSA (SEQ ID NO: 25) |
| 14N13A | QVQLQQPGAELVKPGASVKLSCKASGYIFTSYWMHWVKQRPGQGLEWIGNIDP SDSETHYNQKFKDKATLTVDKSSSTAYMQLSSLTSEDSAVYYCAKGFSDYWGQ GTTLTVSS (SEQ ID NO: 27) |
| 10I23A | EVQLQQSGAELVRPGASVKLSCTASGFNIKDSLMHWVKQRPEQGLEWIGWIDPE DGETKCAPKFQDKATITADTSSNTAYLQLSSLTSEDTAIYYCAVISTVVAPDYWG QGTTLTVSS (SEQ ID NO: 29) |
| 12B18A | EVQLQQSGPELVKPGASVKISCKASGYSFTGYFMNWVKQSHGKSLEWIGRINPY NGDTFYNQKFKGKATLTVDKSSSTAHMELRSLTSEDSAIYYCARGGVVATDYW GQGTTLTVSS (SEQ ID NO: 31) |
| 17O12A | EVQLQQSGPELVKPGASVKISCKASGYSFTGYFMHWVKQSHGKSLEWIGRINPY NGDTFNNQKFKGKATLAVDKSSSTAHMELRSLTSEDSTVYYCARGGYAMDYW GQGTSVTVSS (SEQ ID NO: 33) |
| 15G23A | EVQLQQSGPELVKPGASVKMSCKASGYTFTNYVIHWVKQKPGQGLEWIGYINP YNDGTKYNEKFKGKATLTSDKSSSTAYMELSSLTSEDSAVYYCAKGGTGTGDY WGQGTTLTVSS (SEQ ID NO: 35) |
| 17N8A | EVKLEESGGGMVQPGGSMKVSCVASGFTFSNYWMNWVRQSPEKGLEWVAQIR LKSDNYATHYAESVKGRFTISRDDSKSSVYLQMNNLRAEDTGIYYCTGGGKGG FAYWGQGTLVTVSA (SEQ ID NO: 37) |
| 18M19A | EVQLQQSGPELVKPGASVKMSCKASGYTFTSYVMHWVKQKPGQGLEWIGYINP YNDGTKYNEKFKGKATLTSDKSSSTAYMELSSLTSEDSAVYYCAKGGYYAMD YWGQGTSVTVSS (SEQ ID NO: 39) |
| 11F6A | EVQLQQSGAELVRPGASVKLSCTASGFNIKDSLMHWVKQRPEQGLEWIGWIDPE DGETKCAPKFQDKATITADTSSNTAYLQLSSLTSEDTAIYYCARITTVVATDYWG QGTTLTVSS (SEQ ID NO: 41) |
| 19L14A | QVQLQQPGAELVKPGASVKLSCKASGYTFTSYWINWVKQRPGQGLEWIGNSNP GSSSTNYNEKFKSKAILTVDKSSSTAYMQLSSLTSDDSAVYYCAREGLRRFAYW GQGTLVTVSA (SEQ ID NO: 43) |

VH: heavy chain variable region

TABLE 2

Sequences of light chain variable regions for anti-CD47 mAbs

| mAb clones | VL |
|---|---|
| 9O23A | NIVMTQSPKSMSMSVGERVTLSCKASDNVGTYVSWYQQKPEQSPKLLIYGASN RYTGVPDRFTGSGSARDFTLTITSVQAEDLADYHCGQSYSYPLTFGAGTKLELK (SEQ ID NO: 2) |
| 14P6A | NIVMTQSPKSMSMSVGERVTLSCKASENVGTYVSWYQQKPEQSPNLLIYGASNR YTGVPDRFTGSGSATDFTLTISSVQAEDLADYHCGQTYSYPLTFGAGTKLELK (SEQ ID NO: 4) |
| 4M8A | DVQITQSPSYLAASPGETITINCRASKNISKYLAWFQEKPGKTNKLLIYSGSTLQS GIPSRFSGSGSGTDFTLTISRLEPEDFAMYYCQQHNEYPWTFGGGTKLEIK (SEQ ID NO: 6) |
| 16M17A | DVQITQSPSYLAASPGETITINCRASKSISKYLAWYQEKPGKTNKLLIYSGSTLQS GIPSRFSGSGSGTDFTLTISSLEPEDFAMYYCQQHNEYPWTFGGGTKLEIK (SEQ ID NO: 8) |

TABLE 2-continued

Sequences of light chain variable regions for anti-CD47 mAbs

| mAb clones | VL |
|---|---|
| 13C4A | DVQITQSPSYLAASPGETITINCRASKSISKYLAWYQEKPGKTNKLLIYSGSSLQS GIPSRFSGSGSGTDFTLTISSLEPEDFAMYYCQQHNEYPWTFGGGTKLEIK (SEQ ID NO: 10) |
| 14O18A | DVQITQSPSYLAASPGETITINCRASKSISKYLAWYQEKPGKTNKLLIYSGSTLQS GIPSRFSGSGSGTDFTLTISSLEPEDFAMYYCQQHNEYPWTFGGGTKLEIK (SEQ ID NO: 12) |
| 5D24A | DVQITQSPSYLAASPGETITINCRASKSISKYLAWYQEKPGKTNKLLIYSGSTLQS GIPSRFSGSGSGTDFTLTISSLEPEDFAMYYCQQHNEYPWTFGGGTKLEIK (SEQ ID NO: 14) |
| 11G2A | DVQITQSPSYLAASPGETITINCRASKSISKYLAWYQEKPGKTNKLLIYSGSTLQS GIPSRFSGSGSGTDFTLTISSLEPEDFAMYYCQQHNEYPWTFGGGTKLEIK (SEQ ID NO: 16) |
| 13B18A | AVQITQFPSYLAASPGQTITINCRASKSISKYLAWYQEKPGKTNKLLIYSGSTLQS GIPSRFSGSGSGTDFTLTISSLEPEDFAMYYCQQHNEYPWTFGGGTKLEIK (SEQ ID NO: 18) |
| 1J7A | DVQITQSPTYLTASPGETITINCRANKSISKYLAWYQEKPGKTNKLLIYSGSTLQS GIPSRFSGSGSGTDFTLTISSLEPEDFAMYYCQQHNEYPWTFGGGTKLEIK (SEQ ID NO: 20) |
| 14D18A | DVQITQSPSYLAASPGETITINCRASKSISKYLAWYQEKPGKTNKLLIYSGSTLQS GIPSRFSGSGSGTDFTLTISSLEPEDFAMYYCQQHNEYPWTFGGGTKLEIK (SEQ ID NO: 22) |
| 3O5A | DIVMTQAAPSVPVTPGESVSISCRSSKSLLHSNGNTYLYWFLQRPGQSPQLLIYR MSNLASGVPDRFSGSGSGTAFTLRISRVEAEDVGVYYCMQHLEYPFTFGSGTKL EIK (SEQ ID NO: 24) |
| 17C6A | DIQMNQSPSSLSASLGDTITITCHASQNINVWLSWYQQKPGNIPKLLIYKASNLHT GVPSRFSGSGSGTGFTLTISSLQPEDIATYYCQQGQSYPWTFGGGTKLEIK (SEQ ID NO: 26) |
| 14N13A | DIVMSQSPSSLAVSVGEKVTMSCKSSQSLLYSSNQKNYLAWYQQKPGQSPKVLI YWASTRESGVPDRFTGSGSGTDFTLTISSVKAEDLAVYYCQQYYSYPLTFGAGT KLELK (SEQ ID NO: 28) |
| 10I23A | DVVMTQTPLSLPVSLGVQASISCRSSQSLVHSNGNTYLHWYLQKPGQSPKLLIY KVSNRFSGVPDRFSGSGSGTDFTLKISRVEAEDLGVYFCSQSTHVPWTFGGGTKL EIK (SEQ ID NO: 30) |
| 12B18A | DVVMTQTPVSLPVSLGDQASISCRSSQSLVHSNGNTYLHWYLQRPGQSPKLLIY KVSNRFSGVPDRFSGSGSGTDFTLKISRVEAEDLGVYFCSQSTHVPFTFGSGTKLE IK (SEQ ID NO: 32) |
| 17O12A | DVVMTQTPLSLPVSLGDQASISCRSSQSLVHSNGNTYLYWYLQKPGQSPKLLIYR VSNRFSGVPDRFSGSGSGTDFTLKISRVEAEDLGVYFCFQSTHVPHTFGGGTKLEI K (SEQ ID NO: 34) |
| 15G23A | DVVMTQTPLSLPVSLGDQASISCRSSQSLVHSNGNTYLHWYLQKPGQSPKLLIY KVSNRFSGVPDRFSGSGSGTDFTLKISRVEAEDLGVYFCSQSTHVPPLTFGAGTK LELK (SEQ ID NO: 36) |
| 17N8A | DVVMTQTPLSLPVSLGDQASISCRSTQSLVHSNGNTYLHWYLQKPGQSPKLLIY KVSNRFSGVPDRFSGSGSGTDFTLKISRVEAEDLGVYFCSQSTHVPLTFGAGTKL ELK (SEQ ID NO: 38) |
| 18M19A | DVVMTQTPLSLPVSLGDQASISCRSSQSLVHSNGNTYLHWYLQKPGQSPKLLIY KVSNRFSGVPDRFSGSGSGTDFTLKISRVEAEDLGVYFCSQSTHVPWTFGGGTKL EIK (SEQ ID NO: 40) |
| 11F6A | DVVMTQTPLSLPVSLGDQASISCRSSQSLVHSNGNTYLHWYLQKPGQSPKLLIY KVSNRFSGVPDRFSGSGSGTDFTLKISRVEAEDLGVYFCSQSTHVPLTFGAGTKL ELK (SEQ ID NO: 42) |
| 19L14A | ENVLTQSPAIMSASPGEKVTMTCRASSSVSSSYLHWYQQKSGASPKLWIYSTSN LASGVPARFSGSGSGTSYSLTISSVEAEDAATYYCQQYSGYPFTFGSGTKLEIK (SEQ ID NO: 44) |

VL: light chain variable region

TABLE 3

CDR Regions 1-3 of heavy chain for anti-CD47 mAbs

| mAb clones | HC CDR1 (SEQ ID NO:) | CDR2 (SEQ ID NO:) | CDR3 (SEQ ID NO:) |
|---|---|---|---|
| 9O23A | GYTFTDYY (45) | IYPGSGNT (46) | ARRGPWYFDV (47) |
| 14P6A | GYTFTAYY (48) | IYPGSGNT (49) | ARRGPWYFDV (50) |
| 4M8A | GYTFTSYW (51) | IDPSDSET (52) | ARWGGWLPLDY (53) |
| 16M17A | GYTFTNYW (54) | IDPSDSET (55) | ARMAFITTVVDY (56) |
| 13C4A | GYTFTSYW (57) | IDPSDSET (58) | ARWGYYGRSPLDH (59) |
| 14O18A | GYTFTSYW (60) | IDPSDSET (61) | ARWYYGGSGAMDY (62) |
| 5D24A | GYTFTSSW (63) | IDPSDSET (64) | ARWGYYGKSAIDY (65) |
| 11G2A | GYTFTSYW (66) | IDPSDSEA (67) | ARWGYYGKSAMDY (68) |
| 13B18A | GYTFTSYW (69) | IDPSDSET (70) | SRWGYYGKSAMDY (71) |
| 1J7A | GYTFTSYW (72) | IDPSDSET (73) | ARWGLRGAMDY (74) |
| 14D18A | GYTFTSYW (75) | IDPSDSET (76) | ARWGYYGRSPLDH (77) |
| 3O5A | GFTFSDFY (78) | SRNKANDYTT (79) | ARDTAY (80) |
| 17C6A | GYTFTSYW (81) | IDPSDSET (82) | AGTDLAY (83) |
| 14N13A | GYIFTSYW (84) | IDPSDSET (85) | AKGFSDY (86) |
| 10I23A | GFNIKDSL (87) | IDPEDGET (88) | AVISTVVAPDY (89) |
| 12B18A | GYSFTGYF (90) | INPYNGDT (91) | ARGGVVATDY (92) |
| 17O12A | GYSFTGYF (93) | INPYNGDT (94) | ARGGYAMDY (95) |
| 15G23A | GYTFTNYV (96) | INPYNDGT (97) | AKGGTGTGDY (98) |
| 17N8A | GFTFSNYW (99) | IRLKSDNYAT (100) | TGGGKGGFAY (101) |
| 18M19A | GYTFTSYV (102) | INPYNDGT (103) | AKGGYYAMDY (104) |
| 11F6A | GFNIKDSL (105) | IDPEDGET (106) | ARITTVVATDY (107) |
| 19L14A | GYTFTSYW (108) | SNPGSSST (109) | AREGLRRFAY (110) |

HC: heavy chain; CDR: complementarity determining region
The HC CDRs for the anti-CD47 mAbs were determined utilizing the IMGT method (Lefranc, M.-P. et al., Nucleic Acids Res. 1999; 27: 209-212).

TABLE 4

CDR regions 1-3 of light chain for anti-CD47 mAbs

| mAb clones | LC CDR1 (SEQ ID NO:) | CDR2 (SEQ ID NO:) | CDR3 (SEQ ID NO:) |
|---|---|---|---|
| 9O23A | DNVGTY (111) | GAS (112) | GQSYSYPLT (113) |
| 14P6A | ENVGTY (114) | GAS (115) | GQTYSYPLT (116) |
| 4M8A | KNISKY (117) | SGS (118) | QQHNEYPWT (119) |
| 16M17A | KSISKY (120) | SGS (121) | QQHNEYPWT (122) |
| 13C4A | KSISKY (123) | SGS (124) | QQHNEYPWT (125) |
| 14O18A | KSISKY (126) | SGS (127) | QQHNEYPWT (128) |
| 5D24A | KSISKY (129) | SGS (130) | QQHNEYPWT (131) |
| 11G2A | KSISKY (132) | SGS (133) | QQHNEYPWT (134) |

TABLE 4-continued

CDR regions 1-3 of light chain for anti-CD47 mAbs

| mAb clones | LC CDR1 (SEQ ID NO:) | CDR2 (SEQ ID NO:) | CDR3 (SEQ ID NO:) |
|---|---|---|---|
| 13B18A | KSISKY (135) | SGS (136) | QQHNEYPWT (137) |
| 1J7A | KSISKY (138) | SGS (139) | QQHNEYPWT (140) |
| 14D18A | KSISKY (141) | SGS (142) | QQHNEYPWT (143) |
| 3O5A | KSLLHSNGNTY (144) | RMS (145) | MQHLEYPFT (146) |
| 17C6A | QNINVW (147) | KAS (148) | QQGQSYPWT (149) |
| 14N13A | QSLLYSSNQKNY (150) | WAS (151) | QQYYSYPLT (152) |
| 10I23A | QSLVHSNGNTY (153) | KVS (154) | SQSTHVPWT (155) |
| 12B18A | QSLVHSNGNTY (156) | KVS (157) | SQSTHVPFT (158) |
| 17O12A | QSLVHSNGNTY (159) | RVS (160) | FQSTHVPHT (161) |
| 15G23A | QSLVHSNGNTY (162) | KVS (163) | SQSTHVPPLT (164) |
| 17N8A | QSLVHSNGNTY (165) | KVS (166) | SQSTHVPLT (167) |
| 18M19A | QSLVHSNGNTY (168) | KVS (169) | SQSTHVPWT (170) |
| 11F6A | QSLVHSNGNTY (171) | KVS (172) | SQSTHVPLT (173) |
| 19L14A | SSVSSSY (174) | STS (175) | QQYSGYPFT (176) |

LC: light chain; CDR: complementarity determining region
The LC CDRs for the anti-CD47 mAbs were determined utilizing the IMGT method (Lefranc, M.-P. et al., Nucleic Acids Res. 1999; 27: 209-212).

Example 2

Detection of the Binding of CD47 mAbs to RAM Cells Using FACS

Anti-CD47 mAbs were analyzed by flow cytometry for their ability to bind cell surface CD47. RAJI (ATCC #CCL-86) cells (20,000 cells) cultured in Hanks' Balanced Salt Solution (HBSS) were incubated with either a solution of purified mAb (1 µg/ml) in HBSS or in HBSS alone. Using AlexaFluor488-conjugated anti-mouse IgG secondary Ab, the presence of mouse anti-CD47 mAbs on RAJI cells were measured by FACS (IntelliCyt iQue® Screener; Albuquerque, N. Mex.). Results of the FACS binding analysis of the anti-CD47 mAbs are provided in FIG. 1.

Example 3

Assessment of CD47 mAbs for Their Ability to Block the CD47/SIRPα Interaction

Figure 2A:
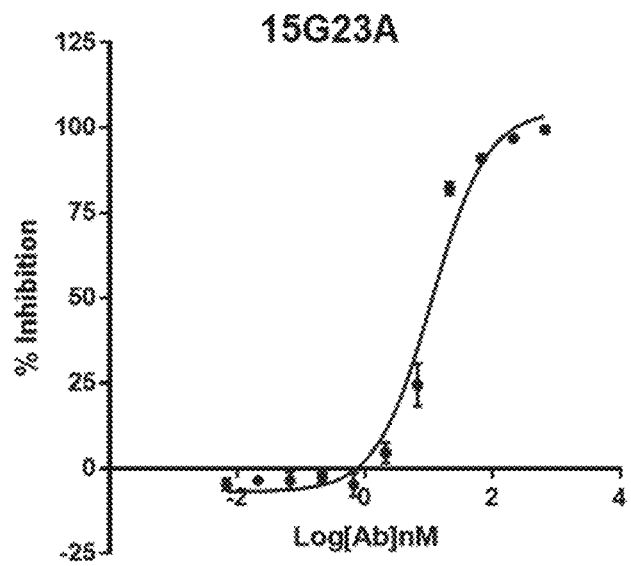
FIGS. 2A-2P show graphs of the activity of the anti-CD47 mAbs blocking the interaction between CD47(ECD)-HIS and SIRPα-huFc as analyzed by ELISA. The curves were produced and $IC_{50}$ values were calculated with Prism GraphPad, v7.
Figure 2B:
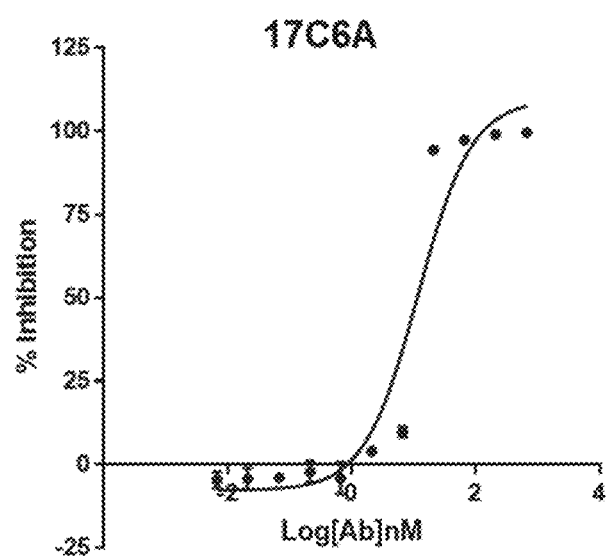
FIG. 2B shows a graph of the activity of the anti-CD47 mAb 17C6A.
Figure 2C:
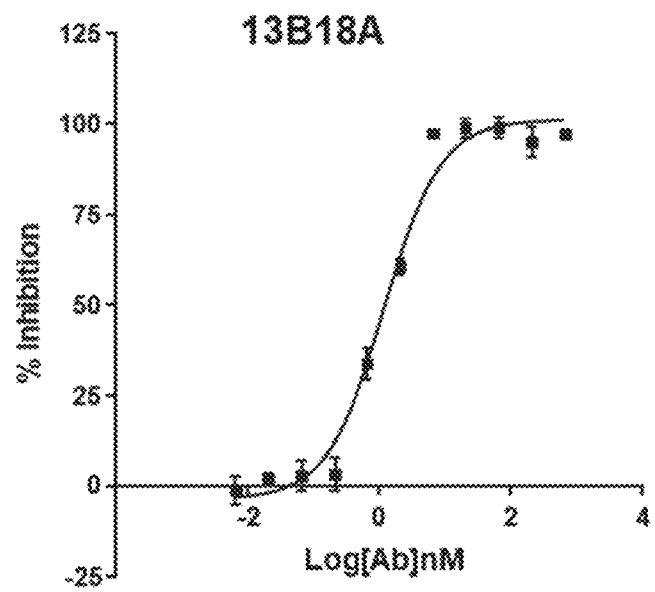
FIG. 2C shows a graph of the activity of the anti-CD47 mAb 13B18A.
Figure 2D:
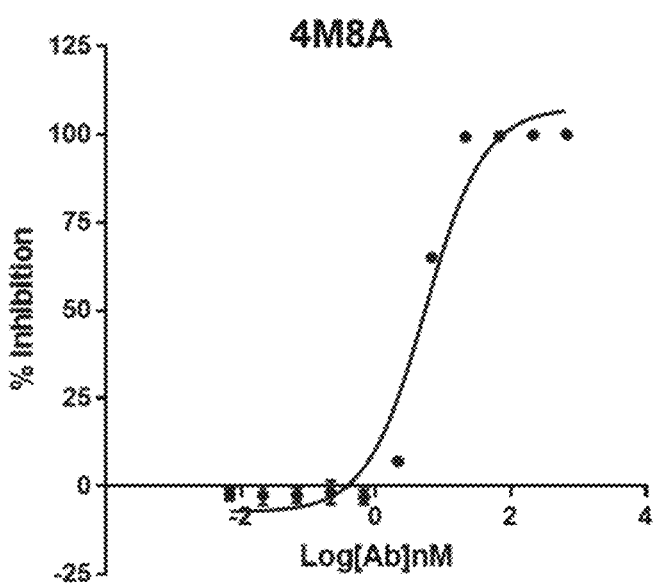
FIG. 2D shows a graph of the activity of the anti-CD47 mAb 4M8A.
Figure 2E:
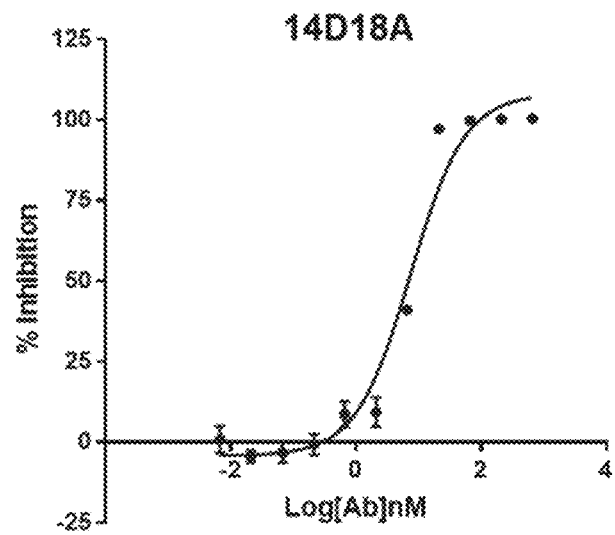
FIG. 2E shows a graph of the activity of the anti-CD47 mAb 14D18A.
Figure 2F:
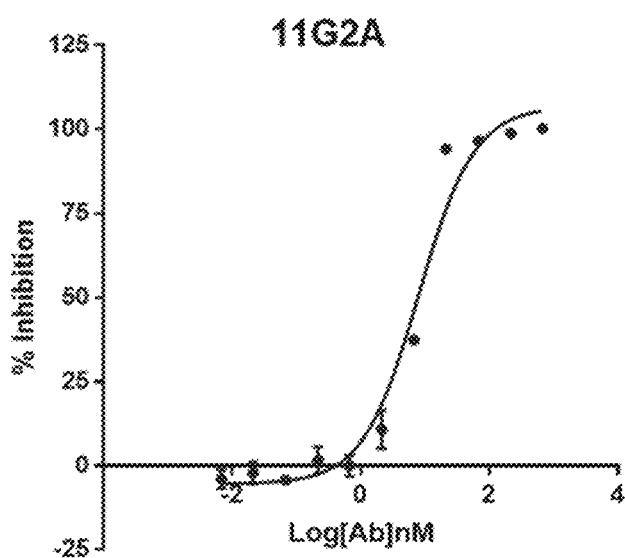
FIG. 2F shows a graph of the activity of the anti-CD47 mAb 11G2A.
Figure 2G:
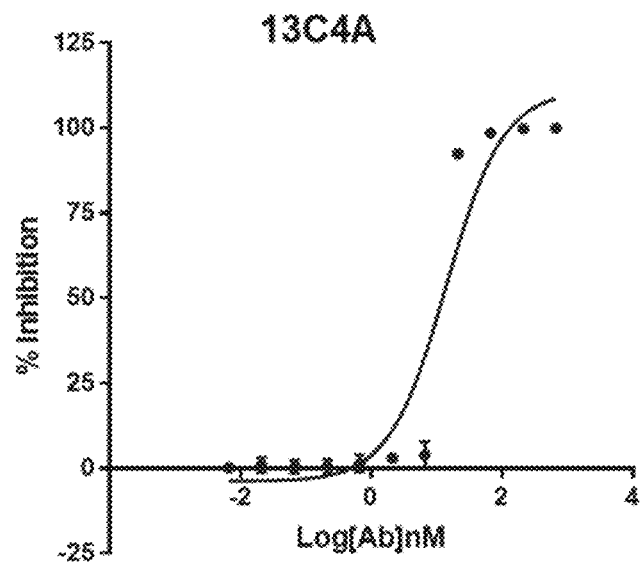
FIG. 2G shows a graph of the activity of the anti-CD47 mAb 13C4A.
Figure 2H:
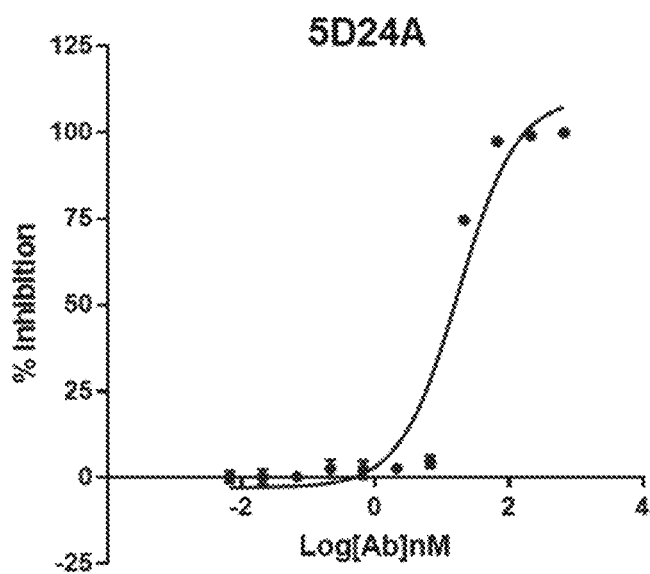
FIG. 2H shows a graph of the activity of the anti-CD47 mAb 5D24A.
Figure 2I:
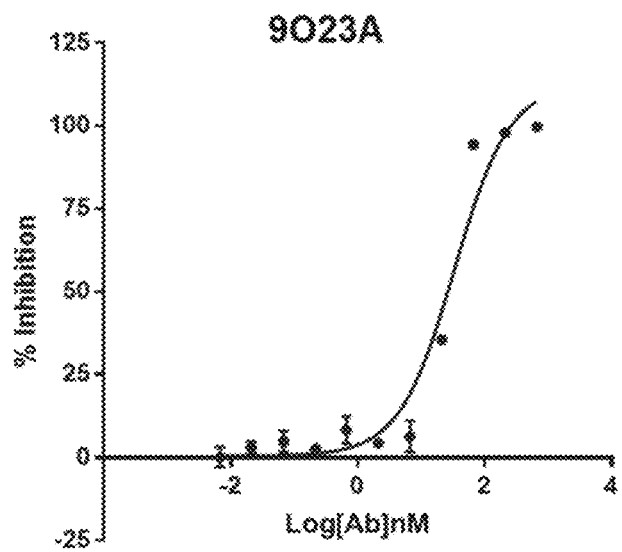
FIG. 2I shows a graph of the activity of the anti-CD47 mAb 9O23A.
Figure 2J:
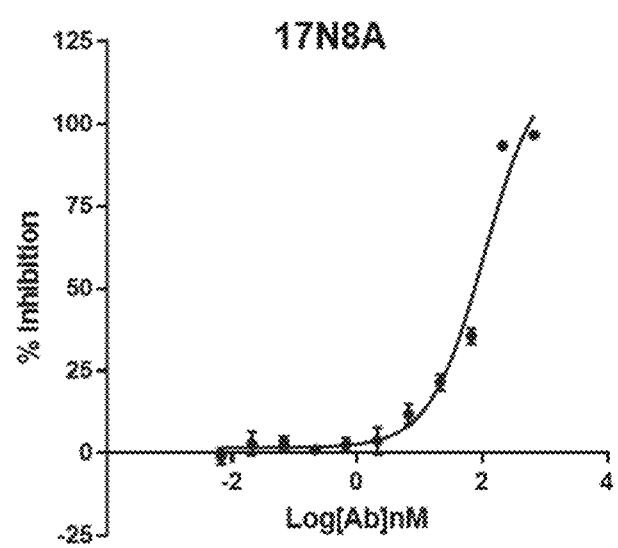
FIG. 2J shows a graph of the activity of the anti-CD47 mAb 17N8A.
Figure 2K:
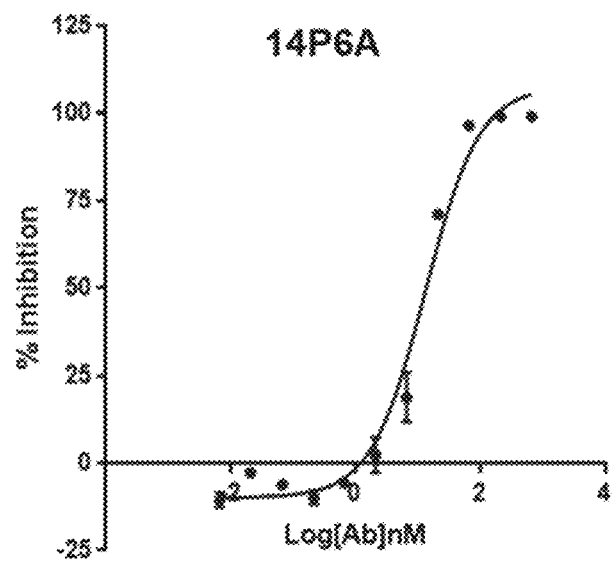
FIG. 2K shows a graph of the activity of the anti-CD47 mAb 14P6A.
Figure 2L:
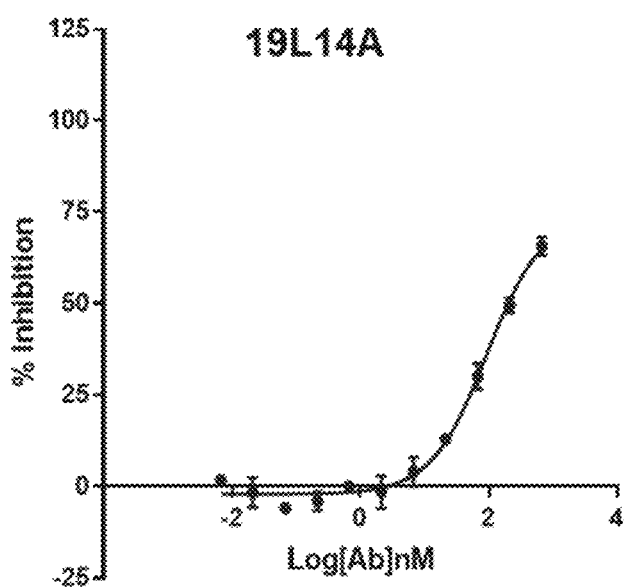
FIG. 2L shows a graph of the activity of the anti-CD47 mAb 19L14A.
Figure 2M:
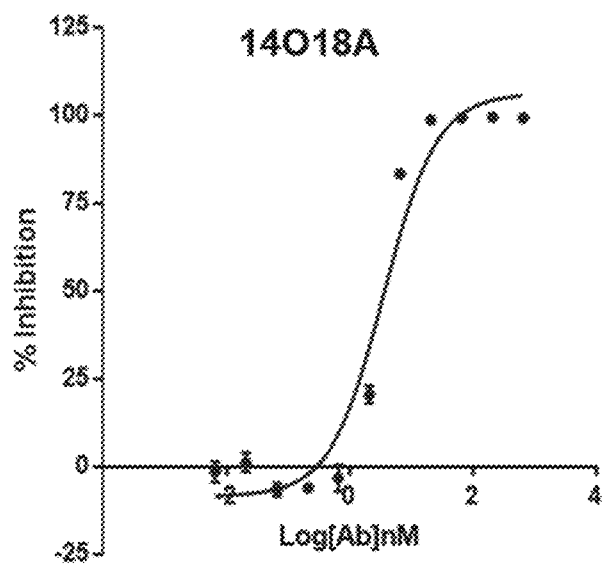
FIG. 2M shows a graph of the activity of the anti-CD47 mAb 14O18A.
Figure 2N:
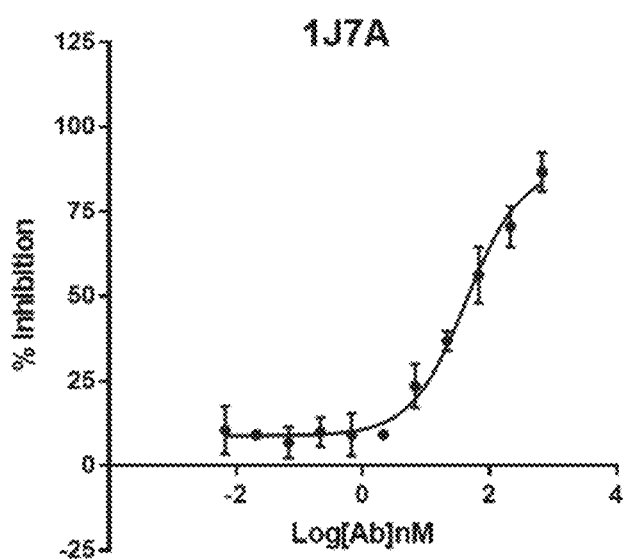
FIG. 2N shows a graph of the activity of the anti-CD47 mAb 1J7A.
Figure 2O:
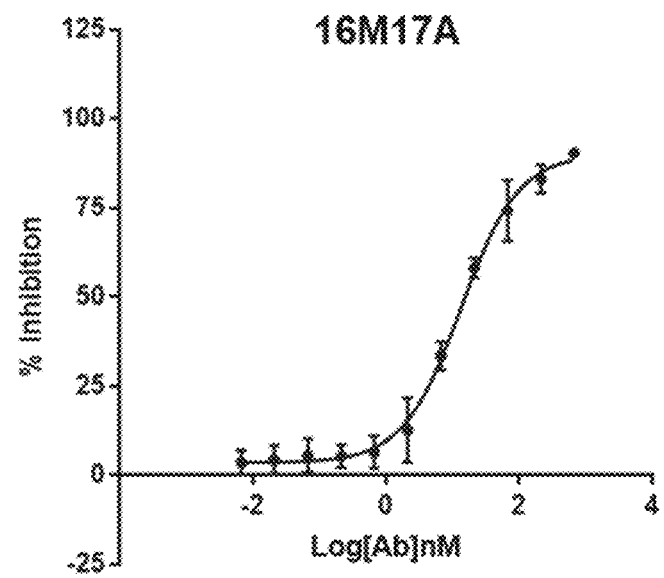
FIG. 2O shows a graph of the activity of the anti-CD47 mAb 16M17A.
Figure 2P:
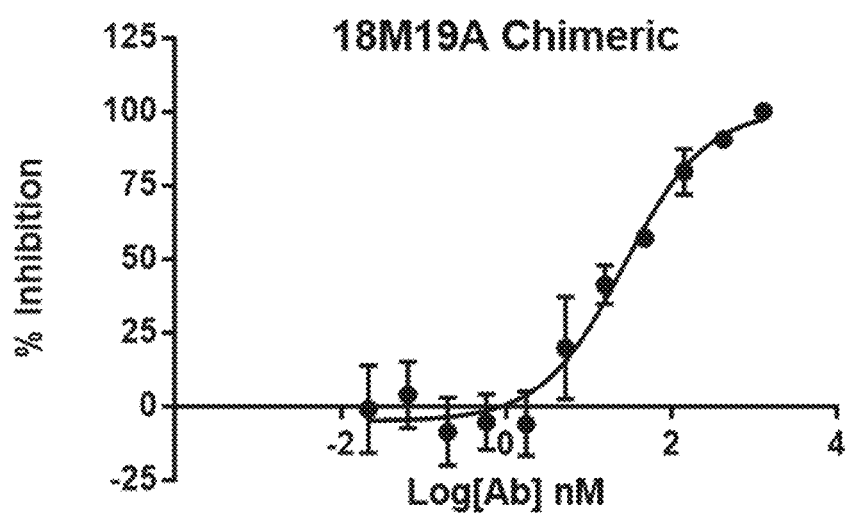

The activity of hybridoma supernatants or purified anti-CD47 mAbs in blocking SIRPα/CD47 interaction was measured by an ELISA assay. Recombinant human CD47 (ECD)-HIS (1 µg/ml) was immobilized on a 384-well ELISA plate. Binding of recombinant huSIRPα-huFc-Biotin (0.5 µg/ml final concentration) was evaluated in the presence of increasing amounts of mouse anti-CD47 mAbs in triplicate. Bound SIRPα was determined using an HRP-conjugated streptavidin secondary antibody (Thermo Fisher Scientific; Waltham, Mass.). Wash steps using PBS supplemented with 0.1% Tween-20 were performed after the addition of CD47, blocking solution, SIRPα protein, secondary antibody, and detection reagents. Results of the ELISA assays are provided in FIGS. 2A-2O. For the 18M19A chimeric (on IgG4 and kapa backbone) antibody (FIG. 2P), blocking activity was measured on a 96-well ELISA plate. Recombinant human CD47(ECD)-HIS (1 µg/mL) was immobilized on a plate. Binding of recombinant huSIRPα-muFc (0.5 µg/mL final concentration) was measured in the presence of increasing amounts of human anti-CD47 mAb in duplicate. Bound SIRPα was measured using an HRP-conjugated anti-muFc secondary antibody (Jackson ImmunoResearch; West Grove, Pa.). Plates were washed as described above. Detection was performed with TMB detection substrate (Thermo Fisher Scientific; Waltham, Mass.). Result of the ELISA assay is provided in FIG. 2P.

Example 4

Assessing the Potential of anti-CD47 mAbs for Inducing Hemagglutination

Figure 3A:
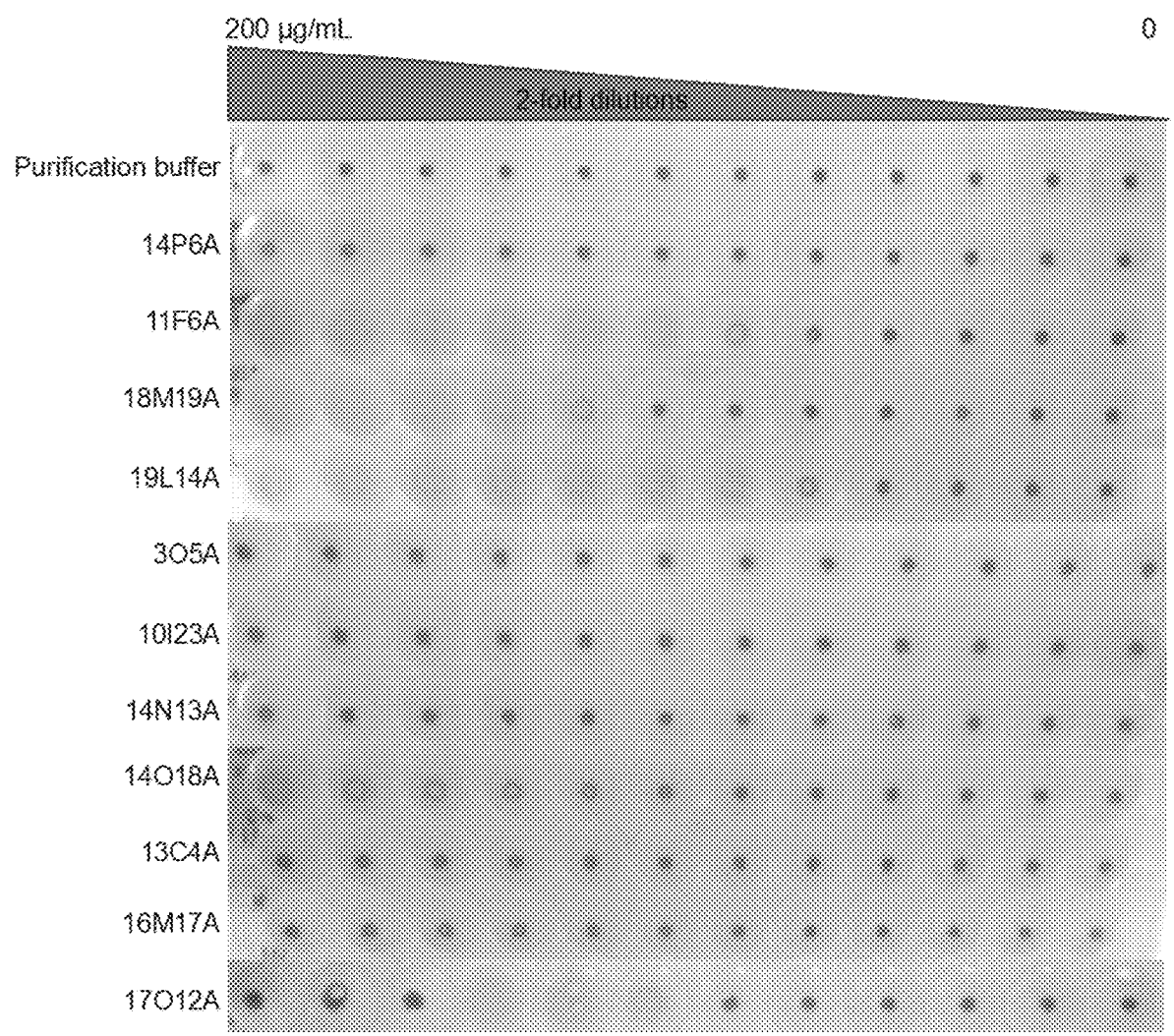
FIGS. 3A-3B show the evaluation of anti-CD47 mAbs in a hemagglutination assay using fresh blood from a donor. Purification buffer, B6H12, and PBS were used as controls. The antibody concentrations are indicated above the panel.
Figure 3B:
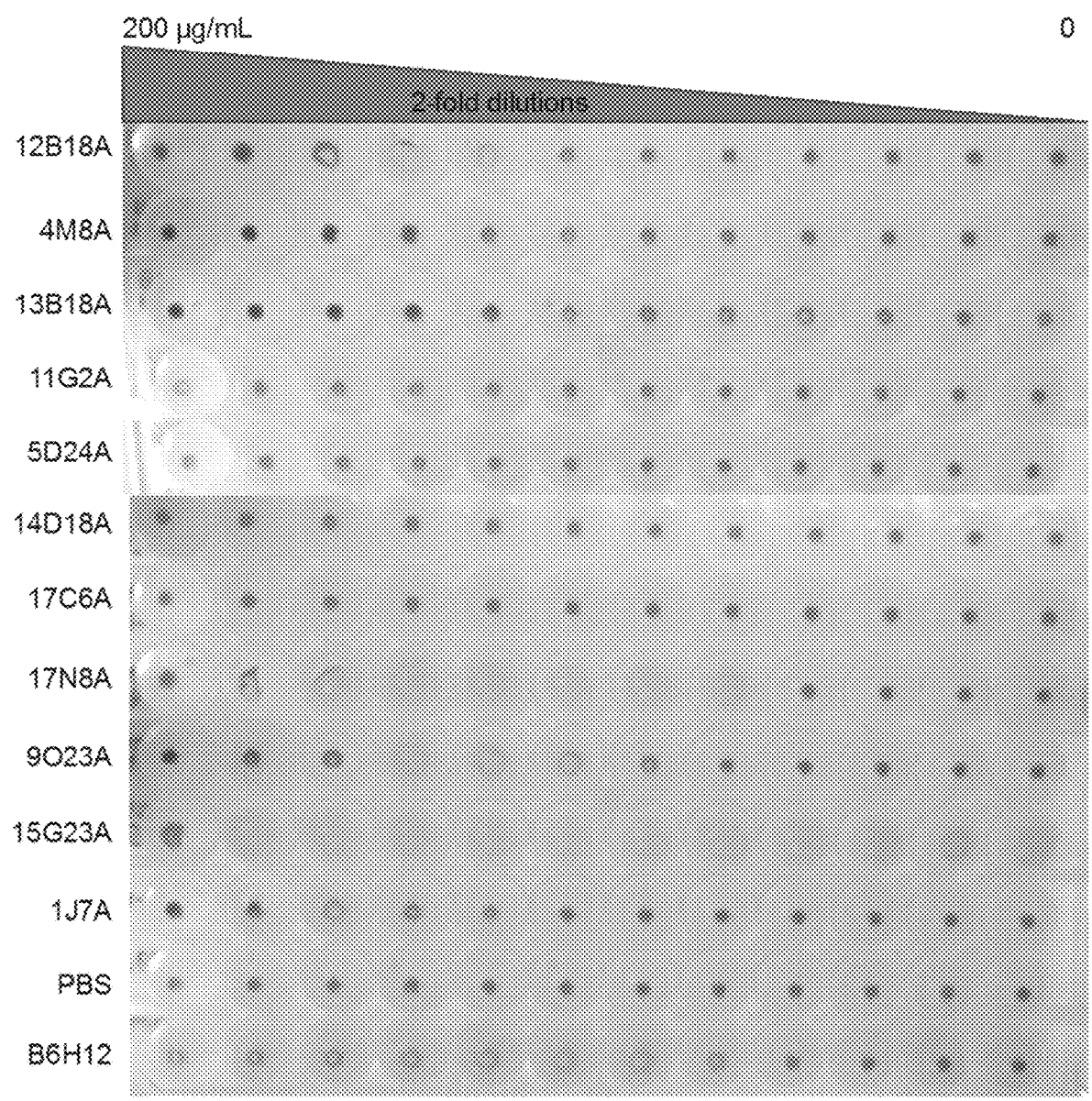

To evaluate the hemagglutinating capacity of anti-CD47 mAbs, purified mAbs, at two-fold serial dilutions, were added in a 96-well clear and round-bottomed plate and incubated with a 2.5% human red blood cell (huRBC) suspension in PBS (0.25% RBC final concentration) at room temperature for 1 hour. Lack of hemagglutination was evidenced by the presence of punctate dots in the center of round-bottomed plates. Evidence of hemagglutination was demonstrated by the presence of a uniform color across the well. Results for the hemagglutination assay are provided in FIGS. 3A-3B.

Example 5

Figure 4A:
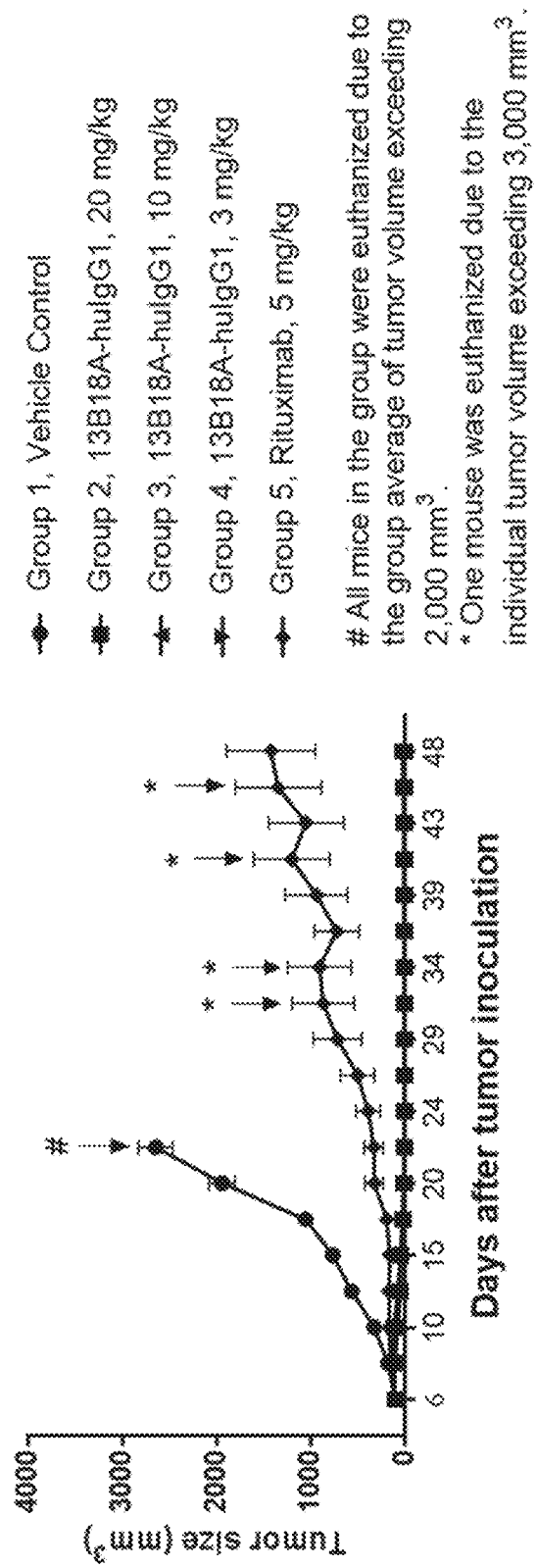
FIGS. 4A-4C show graphs of in vivo anti-tumor activity, body weight, and serum exposure in mice treated with anti-CD47 mAb 13B18A-huIgG1.
Figure 4B:
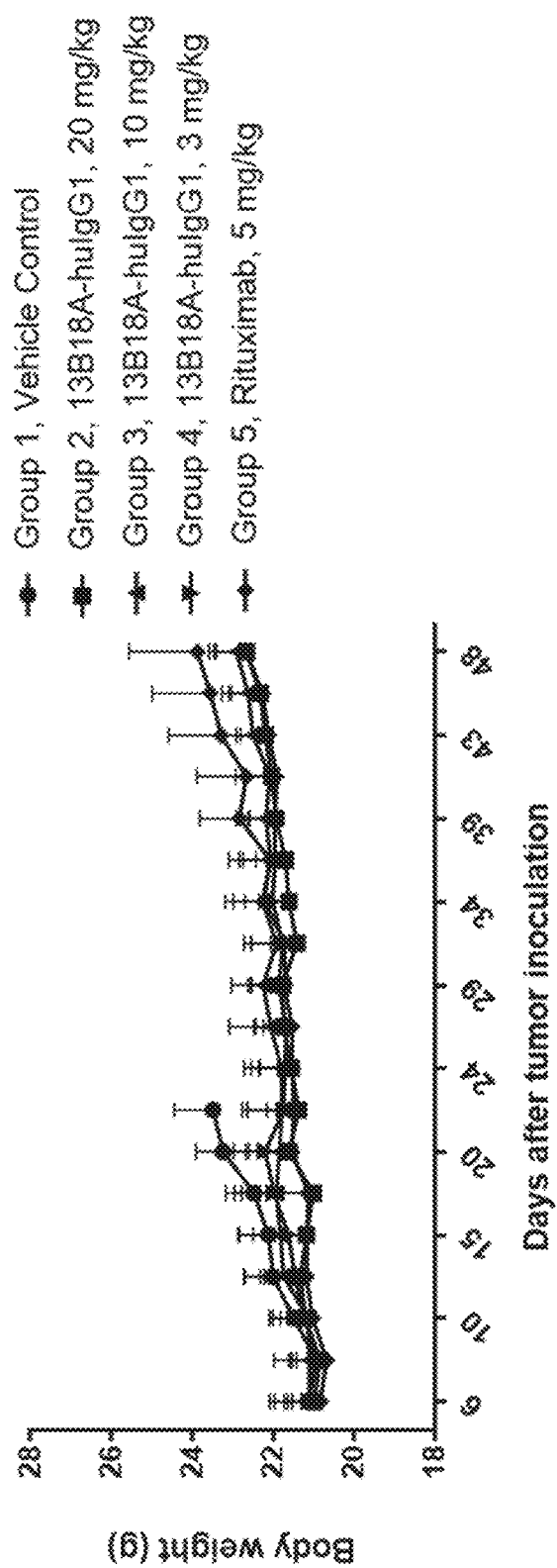
Figure 4C:
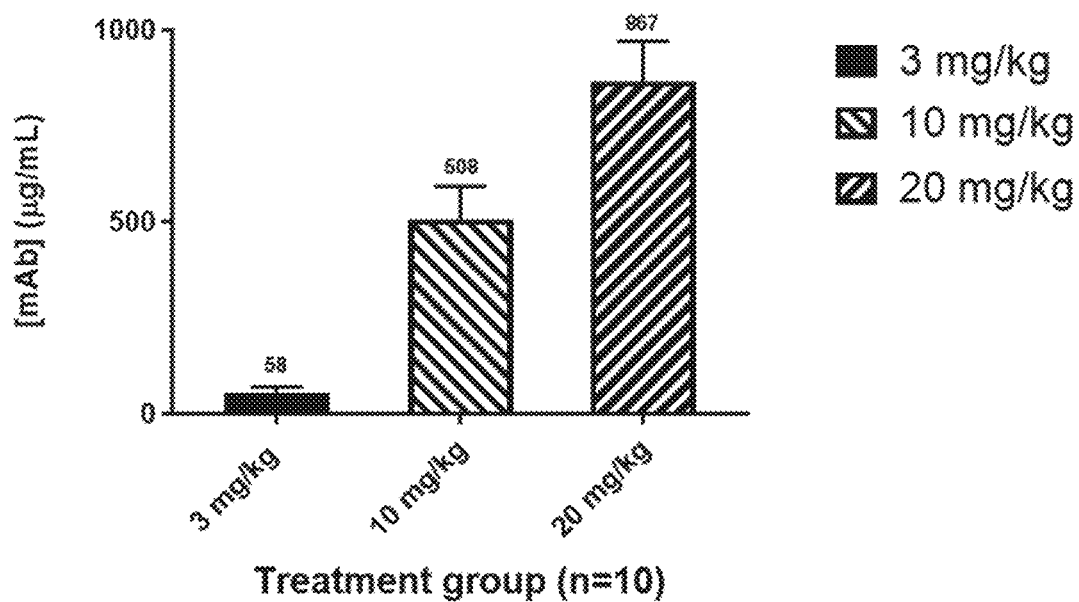

Assessment of In Vivo Efficacy of Chimeric 13B18A in RAJI Cell Xenograft Model A chimeric version of 13B18A antibody (13B18A-huIgG1) was constructed by fusing the variable regions (VH and VL) of 13B18A to the constant regions of human IgG1 heavy chain and kappa light chain, respectively. The resulting antibody was stably expressed in CHO stable pools and purified by Protein A affinity column. To test the efficacy of 13B18A-huIgG1, RAJI cells were inoculated subcutaneously at the right flank of each NOD/SCID mouse (female, n=10/group). Mice were treated with indicated doses of test articles when mean tumor size reached 100 mm$^3$. Doses were given intravenously 3 times per week from day 6 to day 27, and tumor volumes were measured on the same day in two dimensions using a caliper. For pharmacokinetic (PK) analysis, serum was collected 48 hours after final dose and serum levels of 13B18A-huIgG1 were measured by detecting human Fc bound on ELISA plates coated with recombinant human CD47(ECD)-HIS. A standard curve was constructed using serum spiked with a standard of 13B18A-huIgG1 of known concentration. Following washing with PBS supplemented with 0.1% Tween-20, bound antibody was detected by HRP-conjugated anti-huFc secondary antibody (Jackson ImmunoResearch, West Grove, Pa.) followed by TMB detection substrate (Thermo Fisher Scientific; Waltham, Mass.). Tumor growth curves are shown in FIG. 4A. Data of body weight are shown in FIG. 4B. The pharmacokinetics (PK) data is shown in FIG. 4C.

Example 6

Humanization of Anti-CD47 mAbs

Figure 5A:
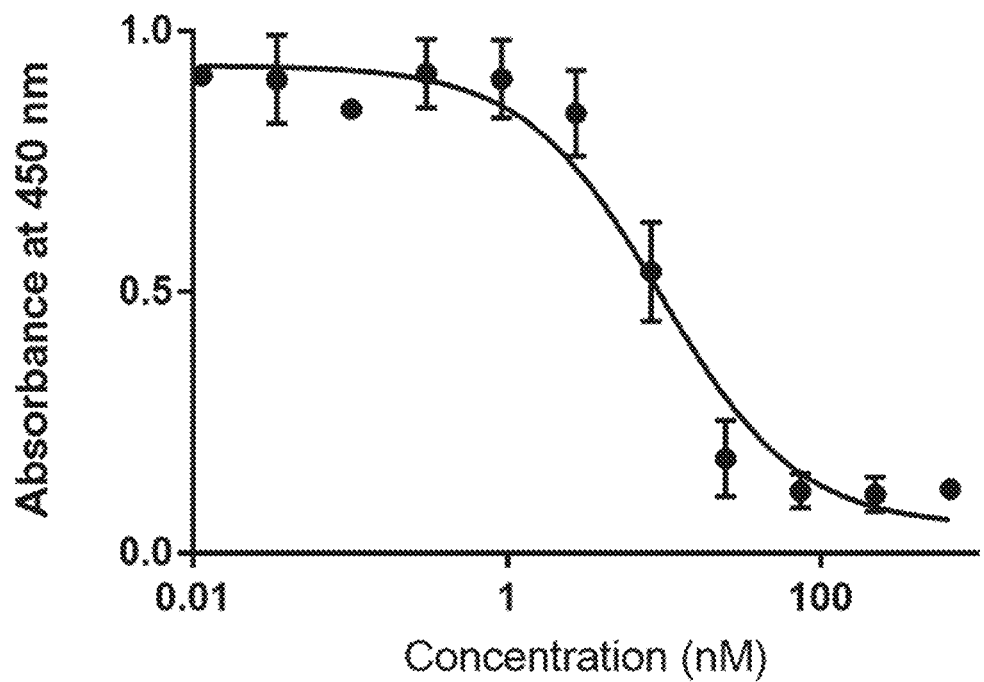
FIGS. 5A and 5B show the activity of humanized anti-CD47 mAbs H3L9 (FIG. 5A) and H5L5 (FIG. 5B) in blocking the interaction between human CD47(ECD)-HIS and huSIRPα-muFc as analyzed by ELISA.
Figure 5B:
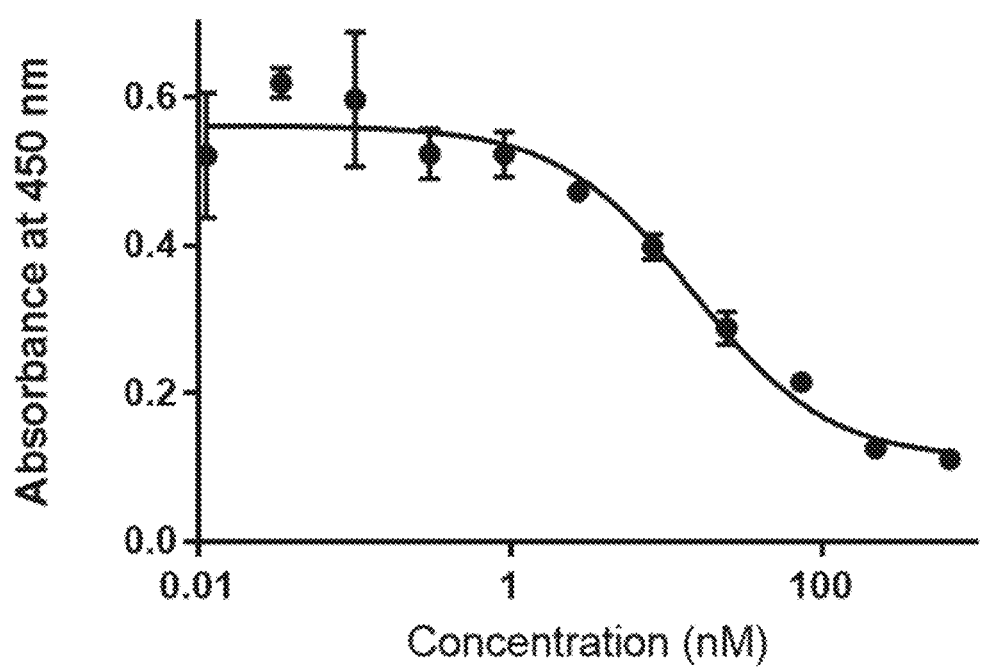
Figure 6:
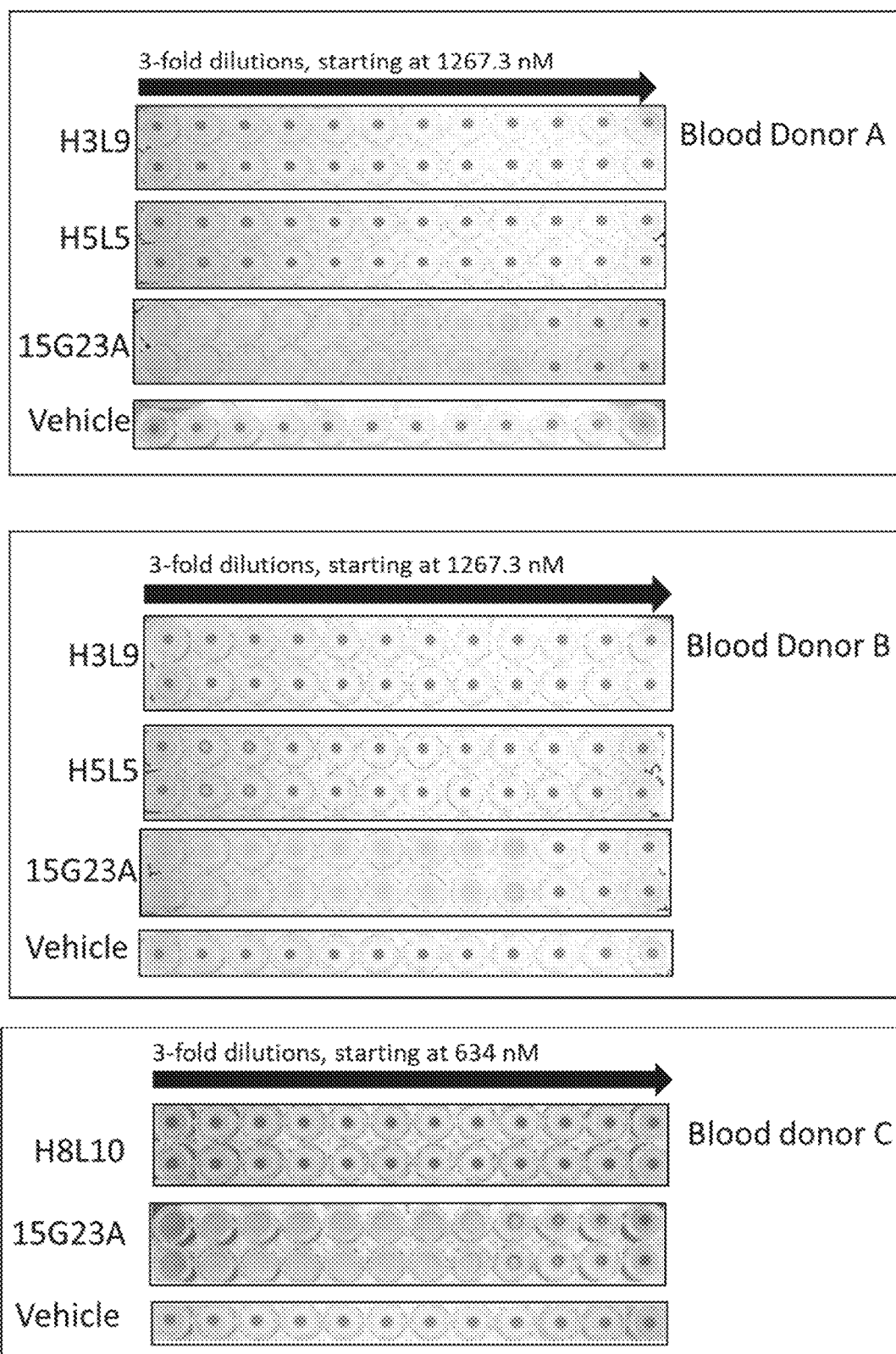
FIG. 6 shows the results for the hemagglutination assay with humanized mAbs H3L9, H5L5 and H8L10. Mouse mAb 15G23A was used as positive control.

The mouse anti-CD47 mAbs 13B18A, 14P6A and 17C6A were humanized to reduce the potential of immunogenicity when used in human patients. The sequences of the variable regions of the heavy and light chains (VH and VL) were compared with the human antibody sequences in the Protein Data Bank (PDB) database and homology models were built. The CDRs in both the heavy and light chains of the mouse mAbs were grafted into human frameworks that have the highest possibility of maintaining the proper structure likely required for antigen binding. Backmutations from human residues to mouse residue or other mutations were designed when necessary. The sequences of the humanized VH and VL regions are shown in Table 5 and Table 6, respectively. The humanized VH and VL regions were fused to the constant regions of human IgG4 heavy chain and kappa light chain, respectively. Constructs corresponding to the mAb sequences were used for transient transfection in 293E cells and purified mAbs were analyzed for their ability to block the SIRPα/CD47 interaction using ELISA. Results are shown as absorbance wherein higher absorbance indicates higher level of SIRPα/CD47 interaction. The IC$_{50}$ values for humanized mAbs are provided in Table 7. The IC$_{50}$ curves for humanized mAbs H3L9 and H5L5 are shown in FIGS. 5A-5B. Results for the hemagglutination assay are provided in FIG. 6. The CDR regions for the humanized mAb H8L10 are provided in Table 8.

TABLE 5

Sequences of heavy chain variable regions of humanized anti-CD47 mAbs

| Design | VH | SEQ ID NO: |
|---|---|---|
| H1 | QVQLVQSGAEVKKPGASVKVSCKASGYTFTSYWMHWVRQAPGQGLEW MGNIDPSDSETHYNQKFKDRVTLTVDTSTSTVYMELSSLRSEDTAVYYCSR WGYYGKSAMDYWGQGTLVTVSS | 183 |
| H2 | QVQLVQSGAEVKKPGASVKLSCKASGYTFTSYWMHWVRQAPGQGLEWM GNIDPSDSETHYNQKFKDRVTLTVDTSTSTAYMELSSLRSEDTAVYYCSR WGYYGKSAMDYWGQGTLVTVSS | 184 |
| H3 | QVQLVQSGAEVKKPGASVKLSCKASGYTFTSYWMHWVRQAPGQGLEWI GNIDPSDSETHYNQKFKDRATLTVDTSTSTAYMELSSLRSEDTAVYYCSR WGYYGKSAMDYWGQGTLVTVSS | 185 |
| H4 | QVQLVQSGAEVKKPGASVKLSCKASGYTFTSYWMHWVRQRPGQGLEWI GNIDPSDSETHYNQKFKDRATLTVDTSTSTAYMELSSLRSEDTAVYYCSR WGYYGKSAMDYWGQGTLVTVSS | 186 |
| H5 | QIQLVQSGAEVKKPGASVKVSCKASGYTFTAYYINWVRQAPGQRLEWIG WIYPGSGNTKYNEKFKGRVTLTVDTSASTAYIELSSLRSEDTAVYYCARRG PWYFDVWGQGTTVTVSS | 187 |
| H6 | QIQLVQSGAEVKKPGASVKVSCKASGYTFTAYYINWVRQAPGQRLEWIG WIYPGSGNTKYNEKFKGRVTLTVDTSASTAYIELSSLRSEDTAVYFCARRG PWYFDVWGQGTTVTVSS | 188 |
| H7 | QIQLVQSGAEVKKPGASVKISCKASGYTFTAYYINWVRQAPGQGLEWIGW IYPGSGNTKYNEKFKGRATLTVDTSASTAYIELSSLRSEDTAVYFCARRGP WYFDVWGQGTTVTVSS | 189 |
| H8 | QVQLVQSGAEVKKPGASVKVSCKASGYTFTSYWMHWVRQAPGQGLEWI GNIDPSDSETHYAQKFQGRVTLTVDKSTSTVYMELSSLRSEDTAVYYCAG TDLAYWGQGTLVTVSS | 199 |

TABLE 6

Sequences of light chain variable regions of humanized anti-CD47 mAbs

| Design | VL | SEQ ID NO: |
|---|---|---|
| L1 | AVQLTQSPSFLSASVGDRVTITCRASKSISKYLAWYQQKPGKANKLLIYSG STLQSGVPSRFSGSGSGTEFTLTISSLQPEDFAMYYCQQHNEYPWTFGGGT KVEIK | 190 |
| L2 | AVQLTQSPSFLSASVGQRITINCRASKSISKYLAWYQQKPGKANKLLIYSGS TLQSGVPSRFSGSGSGTEFTLTISSLQPEDFAMYYCQQHNEYPWTFGGGTK VEIK | 191 |
| L3 | AVQLTQSPSFLSASVGQRITINCRASKSISKYLAWYQEKPGKANKLLIYSGS TLQSGIPSRFSGSGSGTDFTLTISSLQPEDFAMYYCQQHNEYPWTFGGGTK VEIK | 192 |
| L4 | AVQITQSPSFLSASVGQTITINCRASKSISKYLAWYQEKPGKANKLLIYSGST LQSGIPSRFSGSGSGTDFTLTISSLEPEDFAMYYCQQHNEYPWTFGGGTKVE IK | 193 |
| L5 | EIVMTQSPATLSLSPGERATLSCRASENVGTYVSWYQQKPGQAPNLLIYGA SNRYTGIPARFSGSGSGTDFTLTISSLQPEDFAVYHCGQTYSYPLTFGQGTK LEIK | 194 |
| L6 | EIVMTQSPATLSLSPGERATLSCRASENVGTYVSWYQQKPGQSPNLLIYGA SNRYTGIPDRFSGSGSGTDFTLTISSLQPEDFAVYHCGQTYSYPLTFGQGTK LEIK | 195 |
| L7 | EIVMTQSPATLSLSPGERATLSCKASENVGTYVSWYQQKPGQSPNLLIYGA SNRYTGIPDRFSGSGSGTDFTLTISSLQPEDFAVYHCGQTYSYPLTFGQGTK LEIK | 196 |
| L8 | NIVMTQSPATLSLSPGERATLSCKASENVGTYVSWYQQKPGQSPNLLIYGA SNRYTGVPDRFSGSGSATDFTLTISSLQPEDFADYHCGQTYSYPLTFGQGTK LEIK | 197 |
| L9 | DVQLTQSPSFLSASVGDRVTITCRASKSISKYLAWYQQKPGKANKLLIYSG STLQSGVPSRFSGSGSGTEFTLTISSLQPEDFAMYYCQQHNEYPWTFGGGT KVEIK | 198 |
| L10 | EIVMTQSPGTLSLSPGERATLSCHASQNINVWLSWYQQKPGQAPRLLIYKA SNLHTGIPDRFSGSGSGTDFTLTISRLEPEDFAVYYCQQGQSYPFTFGQGTK VEIK | 200 |

TABLE 7

IC$_{50}$ values for anti-CD47 mAbs in SIRPα/CD47 interaction assay

| mAb ID | IC50 (nM) |
|---|---|
| H1L2 | 6.80 |
| H1L3 | 7.43 |
| H1L4 | 8.09 |
| H2L1 | 4.73 |
| H2L3 | 9.56 |
| H2L4 | 6.52 |
| H2L1 | 5.62 |
| H3L2 | 7.88 |
| H3L4 | 5.35 |
| H3L9 | 9.60 |
| H5L5 | 15.06 |
| H6L5 | 9.67 |
| H6L7 | 39.16 |
| H6L8 | 13.20 |
| H8L10 | 1.05 |

H1L2 refers to the mAb with the H1 heavy chain variable region and the L2 light chain variable region; all the other humanized mAbs in the table adopt the same naming rule.

TABLE 8

CDR regions 1-3 of heavy and light chains for humanized mAb H8L10

| | CDR1 (SEQ ID NO:) | CDR2 (SEQ ID NO:) | CDR3 (SEQ ID NO:) |
|---|---|---|---|
| HC | GYTFTSYW (201) | IDPSDSET (202) | AGTDLAY (203) |
| LC | QNINVW (204) | KAS (205) | QQGQSYPFT (206) |

Example 7

Red Blood Cell (RBC) and RAJI Cell Binding Assays

Figure 7A:
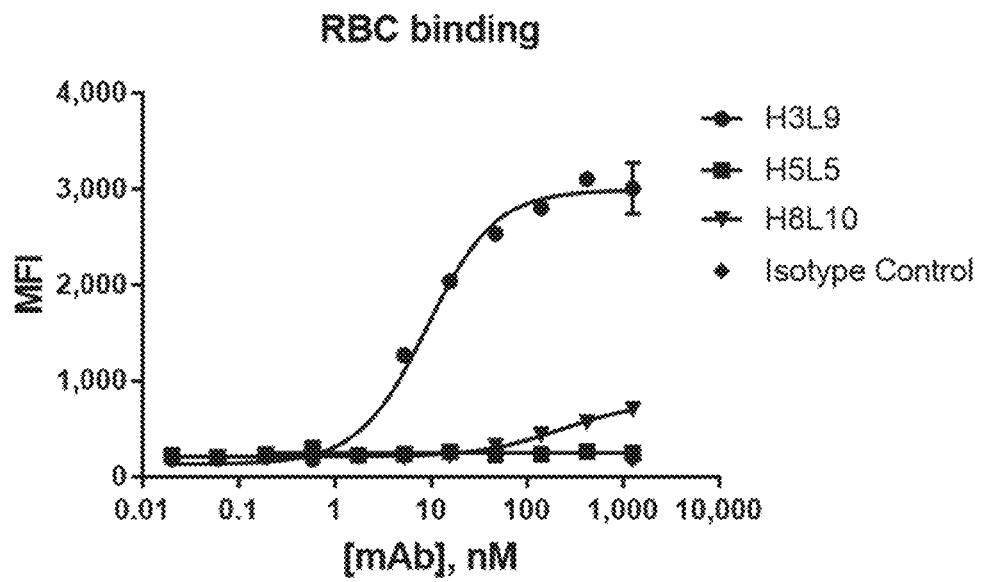
FIGS. 7A-7B show the results for the red blood cell (RBC) (FIG. 7A) and RAJI cell (FIG. 7B) binding assays with humanized mAbs H3L9, H5L5 and H8L10.
Figure 7B:
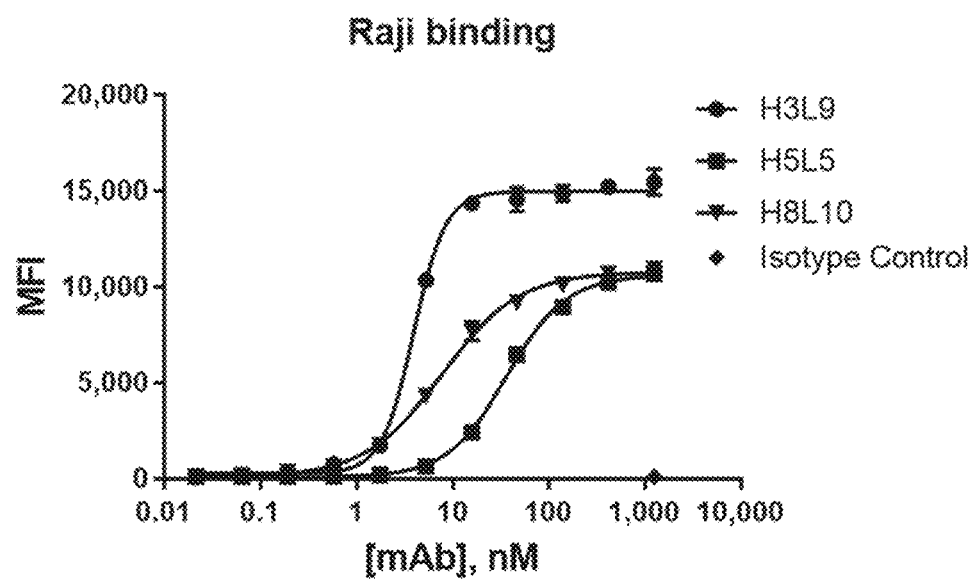

Anti-CD47 mAbs H3L9, H5L5 and H8L10 were analyzed by flow cytometry for their ability to bind cell surface CD47. Purified mAbs were serially diluted (1:3) into FACS buffer (Hanks' Balanced Salt Solution (HBSS) containing 0.1% BSA and 0.05% sodium azide). The top concentration of purified mAb was 190 μg/ml. Red blood cells or RAJI cells (ATCC #CCL-86) (14,000 cells) were pelleted in U-bottom plates by centrifugation at 600 RPM (62×g) for 5 minutes. Cells were resuspended into 20 μL of purified antibodies in FACS buffer and incubated for 30 minutes at room temperature. After incubation, cells were washed three times by FACS buffer. Using PE/Cy7-conjugated anti-human IgG (Biolegend, Cat #409316) secondary Ab, the presence of anti-CD47 mAbs on red blood cells and RAJI cells was measured by FACS (Attune NxT Flow Cytometer; Carlsbad, Calif.). Results of the FACS binding analysis of the anti-CD47 mAbs are provided in FIGS. 7A-7B.

Example 8

Cell-Based SIRPα Binding Assay

Figure 8:
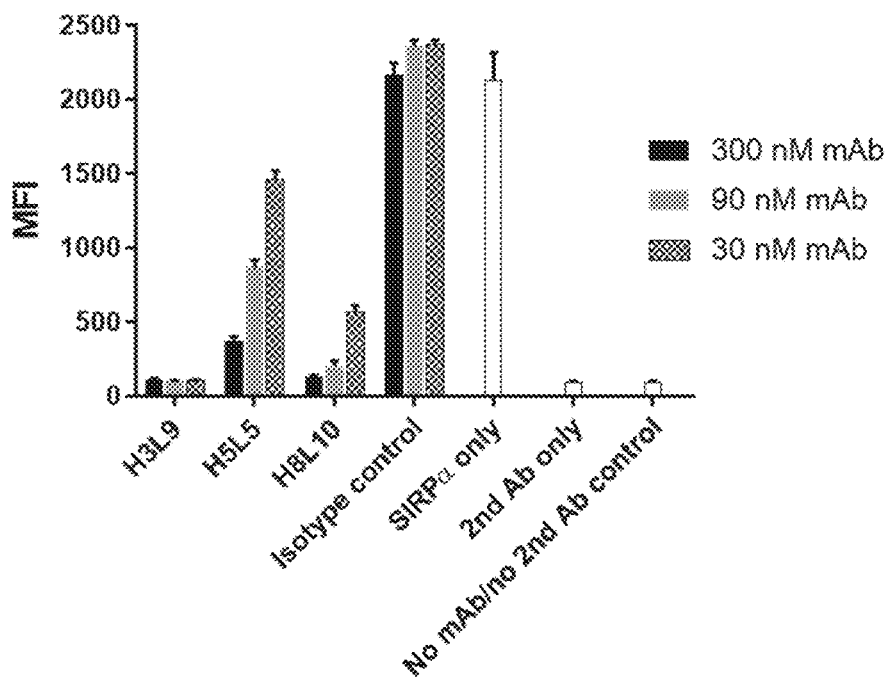
FIG. 8 shows the activity of humanized anti-CD47 mAbs H3L9, H5L5 and H8L10 in blocking the binding of huSIRPα-muFc to RAJI cells. "2nd Ab only" and "No mAb/no 2nd Ab control" are negative controls.

RAJI cells were cultured in RPMI+10% FBS. Human SIRPα (ECD)-mFc (huSIRPα-muFc) protein (human SIRPα ECD fused to mouse Fc) at 30 nM final concentration was incubated with purified humanized anti-CD47 mAbs at 30, 90 and 300 nM. The mixture was then added to 14,000 RAJI cells in a 96-well round bottom plate, mixed and incubated on the nutator for 30 minutes at room temperature. Cells were then centrifuged at 600 rpm for 5 minutes and washed with FACS buffer (HBSS supplemented with 0.1% BSA and 0.05% Sodium Azide) three times. The cells were then incubated with FITC-conjugated donkey anti-mouse Fc polyclonal antibodies (Jackson ImmunoResearch, Cat: 715-095-150) on the nutator for 15 minutes at room temperature, washed with FACS buffer three times and then resuspended in FACS buffer. Cells were then run through the Attune NxT instrument and the data were analyzed by the Attune NxT software. Results of humanized anti-CD47 mAbs H3L9, H5L5 and H8L10 in blocking the binding of huSIRPα-muFc to RAJI cells are shown in FIG. 8.

Example 9

Macrophage-Mediated Phagocytosis Assay

Figure 9:
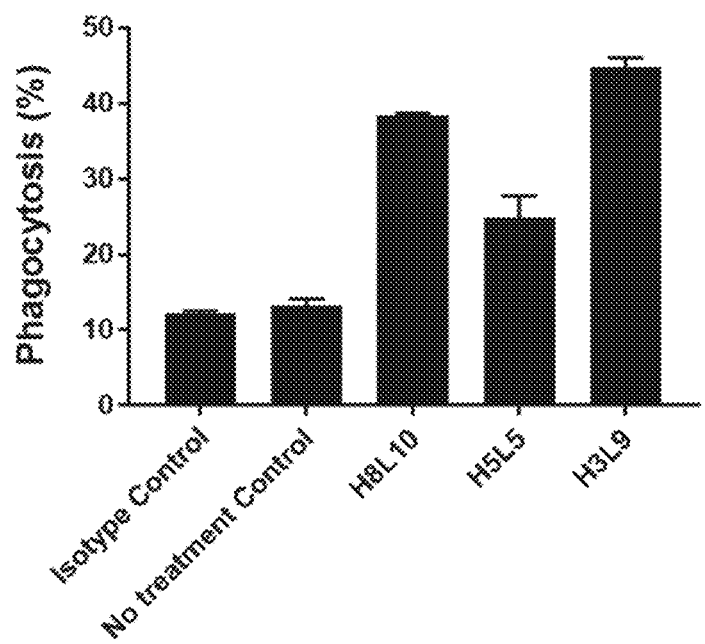
FIG. 9 shows the activity of humanized anti-CD47 mAbs H3L9, H5L5 and H8L10 in inducing macrophage-mediated phagocytosis of RAJI cells.

Human monocytes were induced for 6 days in AIM-V media (Thermo Fisher, Cat: 12055091) containing 50 ng/ml GM-CSF (Shenandoah, Cat: 100-08-20 ug). Macrophages were then polarized with 100 ng/ml INF-gamma (Shenandoah, Cat: 100-77-100 ug) for an additional 2 days. M1 macrophages were defined as CD14+, CD80+, CD163− and CD206+ population. After detached from the tissue culture plates, macrophages were washed once with RPMI-1640 containing 10% FBS and then twice with ice-cold HBSS. The cell number was adjusted to $2\times10^6$ cells/mL in AIM-V media. 25 μL of test mAbs and 25 μL of the macrophage cell suspension (50,000 cells) were added to 50 μL of RAJI cells (100,000 cells) labeled with CFSE (Thermo Fisher, Cat: 34570) in each well of a 96-well plate and incubated for 2 hours at 37° C. The final concentration of mAb was 10 ug/ml. After co-culture, the cell mixtures were stained with PE-Cy7 conjugated anti-human CD14 mAb (Biolegend, Cat: 367111). Following staining, cells were analyzed by flow cytometry. The percentage of both CFSE and PE-Cy7 positive macrophages in the population of PE-Cy7 positive macrophages is presented as phagocytosis. Results of humanized anti-CD47 mAbs H3L9, H5L5 and H8L10 in inducing macrophage-mediated phagocytosis of RAJI cells are shown in FIG. 9.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the present description.

It is claimed:

1. An isolated monoclonal antibody or antigen-binding fragment thereof comprising a heavy chain complementarity determining region 1 (HCDR1), HCDR2, HCDR3, a light chain complementarity determining region 1 (LCDR1), LCDR2, and LCDR3, having the polypeptide sequences of:
   (1) SEQ ID NOs:177, 46, 47, 178, 112, and 179, respectively;
   (2) SEQ ID NOs:51, 52, 53, 117, 118, and 119, respectively;
   (3) SEQ ID NOs:54, 55, 56, 120, 121, and 122, respectively;
   (4) SEQ ID NOs:57, 58, 59, 123, 124, and 125, respectively;
   (5) SEQ ID NOs:60, 61, 62, 126, 127, and 128, respectively;
   (6) SEQ ID NOs:180, 181, 182, 129, 130, and 131, respectively;
   (7) SEQ ID NOs:72, 73, 74, 138, 139, and 140, respectively;
   (8) SEQ ID NOs:78, 79, 80, 144, 145, and 146, respectively;
   (9) SEQ ID NOs:81, 82, 83, 147, 148, and 149, respectively;
   (10) SEQ ID NOs:84, 85, 86, 150, 151, and 152, respectively;
   (11) SEQ ID NOs:87, 88, 89, 153, 154, and 155, respectively;
   (12) SEQ ID NOs:90, 91, 92, 156, 157, and 158, respectively;
   (13) SEQ ID NOs:93, 94, 95, 159, 160, and 161, respectively;
   (14) SEQ ID NOs:96, 97, 98, 162, 163, and 164, respectively;
   (15) SEQ ID NOs:99, 100, 101, 165, 166, and 167, respectively;
   (16) SEQ ID NOs:102, 103, 104, 168, 169, and 170, respectively;
   (17) SEQ ID NOs:105, 106, 107, 171, 172, and 173, respectively;
   (18) SEQ ID NOs:108, 109, 110, 174, 175, and 176, respectively; or
   (19) SEQ ID NOs:201, 202, 203, 204, 205, and 206, respectively;
   wherein the antibody or antigen-binding fragment thereof specifically binds CD47.

2. The isolated monoclonal antibody or antigen-binding fragment of claim 1, comprising:
   a. a heavy chain variable region having a polypeptide sequence at least 95% identical to SEQ ID NO:1, and a light chain variable region having a polypeptide sequence at least 95% identical to SEQ ID NO:2;
   b. a heavy chain variable region having a polypeptide sequence at least 95% identical to SEQ ID NO:3, and a light chain variable region having a polypeptide sequence at least 95% identical to SEQ ID NO:4;
   c. a heavy chain variable region having a polypeptide sequence at least 95% identical to SEQ ID NO:5, and a light chain variable region having a polypeptide sequence at least 95% identical to SEQ ID NO:6;
   d. a heavy chain variable region having a polypeptide sequence at least 95% identical to SEQ ID NO:7, and a light chain variable region having a polypeptide sequence at least 95% identical to SEQ ID NO:8;
   e. a heavy chain variable region having a polypeptide sequence at least 95% identical to SEQ ID NO:9, and a light chain variable region having a polypeptide sequence at least 95% identical to SEQ ID NO:10;

f. a heavy chain variable region having a polypeptide sequence at least 95% identical to SEQ ID NO:11, and a light chain variable region having a polypeptide sequence at least 95% identical to SEQ ID NO:12;

g. a heavy chain variable region having a polypeptide sequence at least 95% identical to SEQ ID NO:13, and a light chain variable region having a polypeptide sequence at least 95% identical to SEQ ID NO:14;

h. a heavy chain variable region having a polypeptide sequence at least 95% identical to SEQ ID NO:15, and a light chain variable region having a polypeptide sequence at least 95% identical to SEQ ID NO:16;

i. a heavy chain variable region having a polypeptide sequence at least 95% identical to SEQ ID NO:17, and a light chain variable region having a polypeptide sequence at least 95% identical to SEQ ID NO:18;

j. a heavy chain variable region having a polypeptide sequence at least 95% identical to SEQ ID NO:19, and a light chain variable region having a polypeptide sequence at least 95% identical to SEQ ID NO:20;

k. a heavy chain variable region having a polypeptide sequence at least 95% identical to SEQ ID NO:21, and a light chain variable region having a polypeptide sequence at least 95% identical to SEQ ID NO:22;

l. a heavy chain variable region having a polypeptide sequence at least 95% identical to SEQ ID NO:23, and a light chain variable region having a polypeptide sequence at least 95% identical to SEQ ID NO:24;

m. a heavy chain variable region having a polypeptide sequence at least 95% identical to SEQ ID NO:25, and a light chain variable region having a polypeptide sequence at least 95% identical to SEQ ID NO:26;

n. a heavy chain variable region having a polypeptide sequence at least 95% identical to SEQ ID NO:27, and a light chain variable region having a polypeptide sequence at least 95% identical to SEQ ID NO:28;

o. a heavy chain variable region having a polypeptide sequence at least 95% identical to SEQ ID NO:29, and a light chain variable region having a polypeptide sequence at least 95% identical to SEQ ID NO:30;

p. a heavy chain variable region having a polypeptide sequence at least 95% identical to SEQ ID NO:31, and a light chain variable region having a polypeptide sequence at least 95% identical to SEQ ID NO:32;

q. a heavy chain variable region having a polypeptide sequence at least 95% identical to SEQ ID NO:33, and a light chain variable region having a polypeptide sequence at least 95% identical to SEQ ID NO:34;

r. a heavy chain variable region having a polypeptide sequence at least 95% identical to SEQ ID NO:35, and a light chain variable region having a polypeptide sequence at least 95% identical to SEQ ID NO:36;

s. a heavy chain variable region having a polypeptide sequence at least 95% identical to SEQ ID NO:37, and a light chain variable region having a polypeptide sequence at least 95% identical to SEQ ID NO:38;

t. a heavy chain variable region having a polypeptide sequence at least 95% identical to SEQ ID NO:39, and a light chain variable region having a polypeptide sequence at least 95% identical to SEQ ID NO:40;

u. a heavy chain variable region having a polypeptide sequence at least 95% identical to SEQ ID NO:41, and a light chain variable region having a polypeptide sequence at least 95% identical to SEQ ID NO:42; or v. a heavy chain variable region having a polypeptide sequence at least 95% identical to SEQ ID NO:43, and a light chain variable region having a polypeptide sequence at least 95% identical to SEQ ID NO:44;

w. a heavy chain variable region having a polypeptide sequence at least 95% identical to SEQ ID NO:183, and a light chain variable region having a polypeptide sequence at least 95% identical to SEQ ID NO:191;

x. a heavy chain variable region having a polypeptide sequence at least 95% identical to SEQ ID NO:183, and a light chain variable region having a polypeptide sequence at least 95% identical to SEQ ID NO:192;

y. a heavy chain variable region having a polypeptide sequence at least 95% identical to SEQ ID NO:183, and a light chain variable region having a polypeptide sequence at least 95% identical to SEQ ID NO:193;

z. a heavy chain variable region having a polypeptide sequence at least 95% identical to SEQ ID NO:184, and a light chain variable region having a polypeptide sequence at least 95% identical to SEQ ID NO:190;

aa. a heavy chain variable region having a polypeptide sequence at least 95% identical to SEQ ID NO:184, and a light chain variable region having a polypeptide sequence at least 95% identical to SEQ ID NO:192;

bb. a heavy chain variable region having a polypeptide sequence at least 95% identical to SEQ ID NO:184, and a light chain variable region having a polypeptide sequence at least 95% identical to SEQ ID NO:193;

cc. a heavy chain variable region having a polypeptide sequence at least 95% identical to SEQ ID NO:185, and a light chain variable region having a polypeptide sequence at least 95% identical to SEQ ID NO:190;

dd. a heavy chain variable region having a polypeptide sequence at least 95% identical to SEQ ID NO:185, and a light chain variable region having a polypeptide sequence at least 95% identical to SEQ ID NO:191;

ee. a heavy chain variable region having a polypeptide sequence at least 95% identical to SEQ ID NO:185, and a light chain variable region having a polypeptide sequence at least 95% identical to SEQ ID NO:193;

ff. a heavy chain variable region having a polypeptide sequence at least 95% identical to SEQ ID NO:185, and a light chain variable region having a polypeptide sequence at least 95% identical to SEQ ID NO:198;

gg. a heavy chain variable region having a polypeptide sequence at least 95% identical to SEQ ID NO:187, and a light chain variable region having a polypeptide sequence at least 95% identical to SEQ ID NO:194;

hh. a heavy chain variable region having a polypeptide sequence at least 95% identical to SEQ ID NO:188, and a light chain variable region having a polypeptide sequence at least 95% identical to SEQ ID NO:194;

ii. a heavy chain variable region having a polypeptide sequence at least 95% identical to SEQ ID NO:188, and a light chain variable region having a polypeptide sequence at least 95% identical to SEQ ID NO:196;

jj. a heavy chain variable region having a polypeptide sequence at least 95% identical to SEQ ID NO:188, and a light chain variable region having a polypeptide sequence at least 95% identical to SEQ ID NO:197; or kk. a heavy chain variable region having a polypeptide sequence at least 95% identical to SEQ ID NO:199, and a light chain variable region having a polypeptide sequence at least 95% identical to SEQ ID NO:200.

3. The isolated monoclonal antibody or antigen-binding fragment thereof of claim 1, comprising:
  a. a heavy chain variable region having the polypeptide sequence of SEQ ID NO:1, and a light chain variable region having the polypeptide sequence of SEQ ID NO:2;
  b. a heavy chain variable region having the polypeptide sequence of SEQ ID NO:3, and a light chain variable region having the polypeptide sequence of SEQ ID NO:4;
  c. a heavy chain variable region having the polypeptide sequence of SEQ ID NO:5, and a light chain variable region having the polypeptide sequence of SEQ ID NO:6;
  d. a heavy chain variable region having the polypeptide sequence of SEQ ID NO:7, and a light chain variable region having the polypeptide sequence of SEQ ID NO:8;
  e. a heavy chain variable region having the polypeptide sequence of SEQ ID NO:9, and a light chain variable region having the polypeptide sequence of SEQ ID NO:10;
  f. a heavy chain variable region having the polypeptide sequence of SEQ ID NO:11, and a light chain variable region having the polypeptide sequence of SEQ ID NO:12;
  g. a heavy chain variable region having the polypeptide sequence of SEQ ID NO:13, and a light chain variable region having the polypeptide sequence of SEQ ID NO:14;
  h. a heavy chain variable region having the polypeptide sequence of SEQ ID NO:15, and a light chain variable region having the polypeptide sequence of SEQ ID NO:16;
  i. a heavy chain variable region having the polypeptide sequence of SEQ ID NO:17, and a light chain variable region having the polypeptide sequence of SEQ ID NO:18;
  j. a heavy chain variable region having the polypeptide sequence of SEQ ID NO:19, and a light chain variable region having the polypeptide sequence of SEQ ID NO:20;
  k. a heavy chain variable region having the polypeptide sequence of SEQ ID NO:21, and a light chain variable region having the polypeptide sequence of SEQ ID NO:22;
  l. a heavy chain variable region having the polypeptide sequence of SEQ ID NO:23, and a light chain variable region having the polypeptide sequence of SEQ ID NO:24;
  m. a heavy chain variable region having the polypeptide sequence of SEQ ID NO:25, and a light chain variable region having the polypeptide sequence of SEQ ID NO:26;
  n. a heavy chain variable region having the polypeptide sequence of SEQ ID NO:27, and a light chain variable region having the polypeptide sequence of SEQ ID NO:28;
  o. a heavy chain variable region having the polypeptide sequence of SEQ ID NO:29, and a light chain variable region having the polypeptide sequence of SEQ ID NO:30;
  p. a heavy chain variable region having the polypeptide sequence of SEQ ID NO:31, and a light chain variable region having the polypeptide sequence of SEQ ID NO:32;
  q. a heavy chain variable region having the polypeptide sequence of SEQ ID NO:33, and a light chain variable region having the polypeptide sequence of SEQ ID NO:34;
  r. a heavy chain variable region having the polypeptide sequence of SEQ ID NO:35, and a light chain variable region having the polypeptide sequence of SEQ ID NO:36;
  s. a heavy chain variable region having the polypeptide sequence of SEQ ID NO:37, and a light chain variable region having the polypeptide sequence of SEQ ID NO:38;
  t. a heavy chain variable region having the polypeptide sequence of SEQ ID NO:39, and a light chain variable region having the polypeptide sequence of SEQ ID NO:40;
  u. a heavy chain variable region having the polypeptide sequence of SEQ ID NO:41, and a light chain variable region having the polypeptide sequence of SEQ ID NO:42; or
  v. a heavy chain variable region having the polypeptide sequence of SEQ ID NO:43, and a light chain variable region having the polypeptide sequence of SEQ ID NO:44;
  w. a heavy chain variable region having the polypeptide sequence of SEQ ID NO:183, and a light chain variable region having the polypeptide sequence of SEQ ID NO:191;
  x. a heavy chain variable region having the polypeptide sequence of SEQ ID NO:183, and a light chain variable region having the polypeptide sequence of SEQ ID NO:192;
  y. a heavy chain variable region having the polypeptide sequence of SEQ ID NO:183, and a light chain variable region having the polypeptide sequence of SEQ ID NO:193;
  z. a heavy chain variable region having the polypeptide sequence of SEQ ID NO:184, and a light chain variable region having the polypeptide sequence of SEQ ID NO:190;
  aa. a heavy chain variable region having the polypeptide sequence of SEQ ID NO:184, and a light chain variable region having the polypeptide sequence of SEQ ID NO:192;
  bb. a heavy chain variable region having the polypeptide sequence of SEQ ID NO:184, and a light chain variable region having the polypeptide sequence of SEQ ID NO:193;
  cc. a heavy chain variable region having the polypeptide sequence of SEQ ID NO:185, and a light chain variable region having the polypeptide sequence of SEQ ID NO:190;
  dd. a heavy chain variable region having the polypeptide sequence of SEQ ID NO:185, and a light chain variable region having the polypeptide sequence of SEQ ID NO:191;
  ee. a heavy chain variable region having the polypeptide sequence of SEQ ID NO:185, and a light chain variable region having the polypeptide sequence of SEQ ID NO:193;
  ff. a heavy chain variable region having the polypeptide sequence of SEQ ID NO:185, and a light chain variable region having the polypeptide sequence of SEQ ID NO:198;

gg. a heavy chain variable region having the polypeptide sequence of SEQ ID NO:187, and a light chain variable region having the polypeptide sequence of SEQ ID NO:194;

hh. a heavy chain variable region having the polypeptide sequence of SEQ ID NO:188, and a light chain variable region having the polypeptide sequence of SEQ ID NO:194;

ii. a heavy chain variable region having the polypeptide sequence of SEQ ID NO:188, and a light chain variable region having the polypeptide sequence of SEQ ID NO:196;

jj. a heavy chain variable region having the polypeptide sequence of SEQ ID NO:188, and a light chain variable region having the polypeptide sequence of SEQ ID NO:197; or kk. a heavy chain variable region having the polypeptide sequence of SEQ ID NO:199, and a light chain variable region having the polypeptide sequence of SEQ ID NO:200.

4. The isolated monoclonal antibody or antigen-binding fragment thereof of claim 1, wherein the antibody or antigen-binding fragment thereof is chimeric and/or human or humanized.

5. The isolated monoclonal antibody or antigen-binding fragment of claim 1, wherein the antibody or antigen-binding fragment thereof is capable of blocking binding of CD47 to signal regulatory protein alpha (SIRPα), inducing macrophage-mediated phagocytosis of cancer cells, or binding cancer cells with minimal to undetectable binding to red blood cells.

6. An isolated nucleic acid encoding the monoclonal antibody or antigen-binding fragment thereof of claim 1.

7. A vector comprising the isolated nucleic acid of claim 6.

8. A host cell comprising the vector of claim 7.

9. A pharmaceutical composition, comprising the isolated monoclonal antibody or antigen-binding fragment thereof of claim 1 and a pharmaceutically acceptable carrier.

10. A method of treating cancer in a subject in need thereof, comprising administering to the subject the pharmaceutical composition of claim 9.

11. A method of determining a level of CD47 in a subject, the method comprising:

a. obtaining a sample from the subject;

b. contacting the sample with a monoclonal antibody or antigen-binding fragment thereof of claim 1;

c. determining a level of CD47 in the subject.

12. The method of claim 11, wherein the sample is a tissue sample or a blood sample.

13. The method of claim 12, wherein the tissue sample is a cancer tissue sample.

14. A method of producing the monoclonal antibody or antigen-binding fragment thereof of claim 1, comprising culturing a cell comprising a nucleic acid encoding the monoclonal antibody or antigen-binding fragment thereof under conditions to produce the monoclonal antibody or antigen-binding fragment thereof, and recovering the antibody or antigen-binding fragment thereof from the cell or culture.

15. A method of producing a pharmaceutical composition comprising the monoclonal antibody or antigen-binding fragment thereof of claim 1, comprising combining the monoclonal antibody or antigen-binding fragment thereof with a pharmaceutically acceptable carrier to obtain the pharmaceutical composition.

16. A bispecific antibody comprising the monoclonal antibody or antigen-binding fragment thereof of claim 1.

17. The monoclonal antibody or antigen-binding fragment thereof of claim 1, wherein the monoclonal antibody or antigen-binding fragment thereof specifically binds human CD47.

* * * * *

SEQUENCE LISTING

<160> NUMBER OF SEQ ID NOS: 207

<210> SEQ ID NO 1
<211> LENGTH: 117
<212> TYPE: PRT
<213> ORGANISM: Artificial Sequence
<220> FEATURE:
<223> OTHER INFORMATION: 9O23A Heavy Chain Variable Region

<400> SEQUENCE: 1

Gln Ile Gln Leu Gln Gln Ser Gly Pro Glu Leu Val Arg Pro Gly Ala
1               5                   10                  15

Ser Val Lys Ile Ser Cys Lys Ala Ser Gly Tyr Thr Phe Thr Asp Tyr
            20                  25                  30

Tyr Ile Asn Trp Val Lys Gln Arg Pro Gly Gln Gly Leu Glu Trp Ile
        35                  40                  45

Gly Trp Ile Tyr Pro Gly Ser Gly Asn Thr Lys Tyr Asn Glu Lys Phe
    50                  55                  60

Lys Gly Lys Ala Thr Leu Thr Val Asp Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Arg Gly Pro Trp Tyr Phe Asp Val Trp Gly Ala Gly Thr Thr
            100                 105                 110

Val Thr Val Ser Ser
        115

<210> SEQ ID NO 2
<211> LENGTH: 107
<212> TYPE: PRT
<213> ORGANISM: Artificial Sequence
<220> FEATURE:
<223> OTHER INFORMATION: 9O23A Light Chain Variable Region

<400> SEQUENCE: 2

```
Asn Ile Val Met Thr Gln Ser Pro Lys Ser Met Ser Met Ser Val Gly
1               5                   10                  15

Glu Arg Val Thr Leu Ser Cys Lys Ala Ser Asp Asn Val Gly Thr Tyr
            20                  25                  30

Val Ser Trp Tyr Gln Gln Lys Pro Glu Gln Ser Pro Lys Leu Leu Ile
        35                  40                  45

Tyr Gly Ala Ser Asn Arg Tyr Thr Gly Val Pro Asp Arg Phe Thr Gly
    50                  55                  60

Ser Gly Ser Ala Arg Asp Phe Thr Leu Thr Ile Thr Ser Val Gln Ala
65                  70                  75                  80

Glu Asp Leu Ala Asp Tyr His Cys Gly Gln Ser Tyr Ser Tyr Pro Leu
                85                  90                  95

Thr Phe Gly Ala Gly Thr Lys Leu Glu Leu Lys
            100                 105
```

<210> SEQ ID NO 3
<211> LENGTH: 117
<212> TYPE: PRT
<213> ORGANISM: Artificial Sequence
<220> FEATURE:
<223> OTHER INFORMATION: 14P6A Heavy Chain Variable Region

<400> SEQUENCE: 3

```
Gln Ile Gln Leu Gln Gln Ser Gly Pro Glu Leu Val Arg Pro Gly Ala
1               5                   10                  15

Ser Val Lys Ile Ser Cys Lys Ala Ser Gly Tyr Thr Phe Thr Ala Tyr
            20                  25                  30

Tyr Ile Asn Trp Val Lys Gln Arg Pro Gly Gln Gly Leu Glu Trp Ile
        35                  40                  45

Gly Trp Ile Tyr Pro Gly Ser Gly Asn Thr Lys Tyr Asn Glu Lys Phe
    50                  55                  60

Lys Gly Lys Ala Thr Leu Thr Val Asp Thr Ser Ser Ser Thr Ala Tyr
65                  70                  75                  80

Ile Gln Leu Ser Ser Leu Thr Ser Glu Asp Ser Ala Val Tyr Phe Cys
                85                  90                  95

Ala Arg Arg Gly Pro Trp Tyr Phe Asp Val Trp Gly Ala Gly Thr Thr
            100                 105                 110

Val Thr Val Ser Ser
        115
```

<210> SEQ ID NO 4
<211> LENGTH: 107
<212> TYPE: PRT
<213> ORGANISM: Artificial Sequence
<220> FEATURE:
<223> OTHER INFORMATION: 14P6A Light Chain Variable Region

<400> SEQUENCE: 4

```
Asn Ile Val Met Thr Gln Ser Pro Lys Ser Met Ser Met Ser Val Gly
1               5                   10                  15

Glu Arg Val Thr Leu Ser Cys Lys Ala Ser Glu Asn Val Gly Thr Tyr
            20                  25                  30
```

```
Val Ser Trp Tyr Gln Gln Lys Pro Glu Gln Ser Pro Asn Leu Leu Ile
         35                  40                  45

Tyr Gly Ala Ser Asn Arg Tyr Thr Gly Val Pro Asp Arg Phe Thr Gly
 50                  55                  60

Ser Gly Ser Ala Thr Asp Phe Thr Leu Thr Ile Ser Ser Val Gln Ala
 65                  70                  75                  80

Glu Asp Leu Ala Asp Tyr His Cys Gly Gln Thr Tyr Ser Tyr Pro Leu
                 85                  90                  95

Thr Phe Gly Ala Gly Thr Lys Leu Glu Leu Lys
            100                 105
```

<210> SEQ ID NO 5
<211> LENGTH: 118
<212> TYPE: PRT
<213> ORGANISM: Artificial Sequence
<220> FEATURE:
<223> OTHER INFORMATION: 4M8A Heavy Chain Variable Region

<400> SEQUENCE: 5

```
Gln Val Gln Leu Gln Gln Pro Gly Ala Glu Leu Val Lys Pro Gly Ala
 1               5                  10                  15

Ser Val Lys Leu Ser Cys Lys Ser Gly Tyr Thr Phe Thr Ser Tyr
         20                  25                  30

Trp Ile His Trp Val Asn Gln Arg Pro Gly Gln Gly Leu Glu Trp Ile
         35                  40                  45

Gly Asn Ile Asp Pro Ser Asp Ser Glu Thr His Tyr Asn Pro Lys Phe
 50                  55                  60

Lys Asp Lys Ala Thr Leu Thr Val Asp Lys Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Arg Trp Gly Gly Trp Leu Pro Leu Asp Tyr Trp Gly Gln Gly Thr
            100                 105                 110

Thr Leu Thr Val Ser Ser
        115
```

<210> SEQ ID NO 6
<211> LENGTH: 107
<212> TYPE: PRT
<213> ORGANISM: Artificial Sequence
<220> FEATURE:
<223> OTHER INFORMATION: 4M8A Light Chain Variable Region

<400> SEQUENCE: 6

```
Asp Val Gln Ile Thr Gln Ser Pro Ser Tyr Leu Ala Ala Ser Pro Gly
 1               5                  10                  15

Glu Thr Ile Thr Ile Asn Cys Arg Ala Ser Lys Asn Ile Ser Lys Tyr
         20                  25                  30

Leu Ala Trp Phe Gln Glu Lys Pro Gly Lys Thr Asn Lys Leu Leu Ile
         35                  40                  45

Tyr Ser Gly Ser Thr Leu Gln Ser Gly Ile Pro Ser Arg Phe Ser Gly
 50                  55                  60

Ser Gly Ser Gly Thr Asp Phe Thr Leu Thr Ile Ser Arg Leu Glu Pro
 65                  70                  75                  80

Glu Asp Phe Ala Met Tyr Tyr Cys Gln Gln His Asn Glu Tyr Pro Trp
                 85                  90                  95

Thr Phe Gly Gly Gly Thr Lys Leu Glu Ile Lys
            100                 105
```

```
<210> SEQ ID NO 7
<211> LENGTH: 119
<212> TYPE: PRT
<213> ORGANISM: Artificial Sequence
<220> FEATURE:
<223> OTHER INFORMATION: 16M17A Heavy Chain Variable Region

<400> SEQUENCE: 7

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Asn Tyr
            20                  25                  30

Trp Met His Trp Val Lys Gln Arg Pro Gly Gln Gly Leu Glu Trp Ile
        35                  40                  45

Gly Asn Ile Asp Pro Ser Asp Ser Glu Thr His Tyr Asn Gln Lys Phe
    50                  55                  60

Lys Asp Lys Ala Thr Leu Thr Val Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Met Ala Phe Ile Thr Thr Val Val Asp Tyr Trp Gly Gln Gly
            100                 105                 110

Thr Thr Leu Thr Val Ser Ser
        115

<210> SEQ ID NO 8
<211> LENGTH: 107
<212> TYPE: PRT
<213> ORGANISM: Artificial Sequence
<220> FEATURE:
<223> OTHER INFORMATION: 16M17A Light Chain Variable Region

<400> SEQUENCE: 8

Asp Val Gln Ile Thr Gln Ser Pro Ser Tyr Leu Ala Ala Ser Pro Gly
1               5                   10                  15

Glu Thr Ile Thr Ile Asn Cys Arg Ala Ser Lys Ser Ile Ser Lys Tyr
            20                  25                  30

Leu Ala Trp Tyr Gln Glu Lys Pro Gly Lys Thr Asn Lys Leu Leu Ile
        35                  40                  45

Tyr Ser Gly Ser Thr Leu Gln Ser Gly Ile Pro Ser Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Met Tyr Tyr Cys Gln Gln His Asn Glu Tyr Pro Trp
                85                  90                  95

Thr Phe Gly Gly Gly Thr Lys Leu Glu Ile Lys
            100                 105

<210> SEQ ID NO 9
<211> LENGTH: 120
<212> TYPE: PRT
<213> ORGANISM: Artificial Sequence
<220> FEATURE:
<223> OTHER INFORMATION: 13C4A Heavy Chain Variable Region

<400> SEQUENCE: 9

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30
```

Trp Met His Trp Val Lys Gln Arg Pro Gly Gln Gly Leu Glu Trp Ile
             35                  40                  45

Gly Asn Ile Asp Pro Ser Asp Ser Glu Thr His Tyr Asn Gln Lys Phe
 50                  55                  60

Lys Asp Lys Ala Thr Leu Thr Val Asp Lys Ser Ser Ser Thr Ala Tyr
65                   70                  75                  80

Met Gln Leu Ser Ser Leu Thr Ser Glu Asp Ser Ala Val Tyr Tyr Cys
                 85                  90                  95

Ala Arg Trp Gly Tyr Tyr Gly Arg Ser Pro Leu Asp His Trp Gly Gln
            100                 105                 110

Gly Thr Thr Leu Thr Val Ser Ser
        115                 120

<210> SEQ ID NO 10
<211> LENGTH: 107
<212> TYPE: PRT
<213> ORGANISM: Artificial Sequence
<220> FEATURE:
<223> OTHER INFORMATION: 13C4A Light Chain Variable Region

<400> SEQUENCE: 10

Asp Val Gln Ile Thr Gln Ser Pro Ser Tyr Leu Ala Ala Ser Pro Gly
1               5                   10                  15

Glu Thr Ile Thr Ile Asn Cys Arg Ala Ser Lys Ser Ile Ser Lys Tyr
             20                  25                  30

Leu Ala Trp Tyr Gln Glu Lys Pro Gly Lys Thr Asn Lys Leu Leu Ile
            35                  40                  45

Tyr Ser Gly Ser Ser Leu Gln Ser Gly Ile Pro Ser Arg Phe Ser Gly
 50                  55                  60

Ser Gly Ser Gly Thr Asp Phe Thr Leu Thr Ile Ser Ser Leu Glu Pro
65                   70                  75                  80

Glu Asp Phe Ala Met Tyr Tyr Cys Gln Gln His Asn Glu Tyr Pro Trp
                 85                  90                  95

Thr Phe Gly Gly Gly Thr Lys Leu Glu Ile Lys
            100                 105

<210> SEQ ID NO 11
<211> LENGTH: 120
<212> TYPE: PRT
<213> ORGANISM: Artificial Sequence
<220> FEATURE:
<223> OTHER INFORMATION: 14O18A Heavy Chain Variable Region

<400> SEQUENCE: 11

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
             20                  25                  30

Trp Met His Trp Val Lys Gln Arg Pro Gly Gln Gly Leu Glu Trp Ile
            35                  40                  45

Gly Asn Ile Asp Pro Ser Asp Ser Glu Thr His Tyr Asn Gln Lys Phe
 50                  55                  60

Lys Asp Lys Ala Thr Leu Thr Leu Asp Lys Ser Ser Ser Thr Ala Tyr
65                   70                  75                  80

Met Gln Leu Ser Ser Leu Thr Ser Glu Asp Ser Ala Val Tyr Tyr Cys
                 85                  90                  95

```
Ala Arg Trp Tyr Tyr Gly Gly Ser Gly Ala Met Asp Tyr Trp Gly Gln
            100                 105                 110

Gly Thr Ser Val Thr Val Ser Ser
        115                 120

<210> SEQ ID NO 12
<211> LENGTH: 107
<212> TYPE: PRT
<213> ORGANISM: Artificial Sequence
<220> FEATURE:
<223> OTHER INFORMATION: 14O18A Light Chain Variable Region

<400> SEQUENCE: 12

Asp Val Gln Ile Thr Gln Ser Pro Ser Tyr Leu Ala Ala Ser Pro Gly
1               5                   10                  15

Glu Thr Ile Thr Ile Asn Cys Arg Ala Ser Lys Ser Ile Ser Lys Tyr
            20                  25                  30

Leu Ala Trp Tyr Gln Glu Lys Pro Gly Lys Thr Asn Lys Leu Leu Ile
            35                  40                  45

Tyr Ser Gly Ser Thr Leu Gln Ser Gly Ile Pro Ser Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Met Tyr Tyr Cys Gln Gln His Asn Glu Tyr Pro Trp
                85                  90                  95

Thr Phe Gly Gly Gly Thr Lys Leu Glu Ile Lys
            100                 105

<210> SEQ ID NO 13
<211> LENGTH: 120
<212> TYPE: PRT
<213> ORGANISM: Artificial Sequence
<220> FEATURE:
<223> OTHER INFORMATION: 5D24A Heavy Chain Variable Region

<400> SEQUENCE: 13

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Ser
            20                  25                  30

Trp Met His Trp Val Lys Gln Arg Pro Gly Gln Gly Leu Glu Trp Ile
            35                  40                  45

Gly Asn Ile Asp Pro Ser Asp Ser Glu Thr His Tyr Asn Gln Lys Phe
        50                  55                  60

Lys Asp Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Trp Gly Tyr Tyr Gly Lys Ser Ala Ile Asp Tyr Trp Gly Gln
            100                 105                 110

Gly Thr Ser Val Thr Val Ser Ser
        115                 120

<210> SEQ ID NO 14
<211> LENGTH: 107
<212> TYPE: PRT
<213> ORGANISM: Artificial Sequence
<220> FEATURE:
<223> OTHER INFORMATION: 5D24A Light Chain Variable Region
```

<400> SEQUENCE: 14

Asp Val Gln Ile Thr Gln Ser Pro Ser Tyr Leu Ala Ala Ser Pro Gly
1               5                   10                  15

Glu Thr Ile Thr Ile Asn Cys Arg Ala Ser Lys Ser Ile Ser Lys Tyr
            20                  25                  30

Leu Ala Trp Tyr Gln Glu Lys Pro Gly Lys Thr Asn Lys Leu Leu Ile
        35                  40                  45

Tyr Ser Gly Ser Thr Leu Gln Ser Gly Ile Pro Ser Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Met Tyr Tyr Cys Gln Gln His Asn Glu Tyr Pro Trp
                85                  90                  95

Thr Phe Gly Gly Gly Thr Lys Leu Glu Ile Lys
            100                 105

<210> SEQ ID NO 15
<211> LENGTH: 120
<212> TYPE: PRT
<213> ORGANISM: Artificial Sequence
<220> FEATURE:
<223> OTHER INFORMATION: 11G2A Heavy Chain Variable Region

<400> SEQUENCE: 15

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Asn Ile Asp Pro Ser Asp Ser Glu Ala His Tyr Asn Gln Lys Phe
50                  55                  60

Arg Asp Lys Ala Thr Leu Thr Val Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Trp Gly Tyr Gly Lys Ser Ala Met Asp Tyr Trp Gly Gln
            100                 105                 110

Gly Thr Ser Val Thr Val Ser Ser
        115                 120

<210> SEQ ID NO 16
<211> LENGTH: 107
<212> TYPE: PRT
<213> ORGANISM: Artificial Sequence
<220> FEATURE:
<223> OTHER INFORMATION: 11G2A Light Chain Variable Region

<400> SEQUENCE: 16

Asp Val Gln Ile Thr Gln Ser Pro Ser Tyr Leu Ala Ala Ser Pro Gly
1               5                   10                  15

Glu Thr Ile Thr Ile Asn Cys Arg Ala Ser Lys Ser Ile Ser Lys Tyr
            20                  25                  30

Leu Ala Trp Tyr Gln Glu Lys Pro Gly Lys Thr Asn Lys Leu Leu Ile
        35                  40                  45

Tyr Ser Gly Ser Thr Leu Gln Ser Gly Ile Pro Ser Arg Phe Ser Gly
50                  55                  60

```
Ser Gly Ser Gly Thr Asp Phe Thr Leu Thr Ile Ser Ser Leu Glu Pro
 65                  70                  75                  80

Glu Asp Phe Ala Met Tyr Tyr Cys Gln Gln His Asn Glu Tyr Pro Trp
                 85                  90                  95

Thr Phe Gly Gly Gly Thr Lys Leu Glu Ile Lys
                100                 105

<210> SEQ ID NO 17
<211> LENGTH: 120
<212> TYPE: PRT
<213> ORGANISM: Artificial Sequence
<220> FEATURE:
<223> OTHER INFORMATION: 13B18A Heavy Chain Variable Region

<400> SEQUENCE: 17

Gln Val Gln Leu Gln Gln Pro Gly Ala Glu Leu Val Lys Pro Gly Ala
 1               5                  10                  15

Ser Val Lys Leu Ser Cys Lys Ala Ser Gly Tyr Thr Phe Thr Ser Tyr
                20                  25                  30

Trp Met His Trp Val Lys Gln Arg Pro Gly Gln Gly Leu Glu Trp Ile
             35                  40                  45

Gly Asn Ile Asp Pro Ser Asp Ser Glu Thr His Tyr Asn Gln Lys Phe
 50                  55                  60

Lys Asp Lys Ala Thr Leu Thr Val Asp Lys Ser Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ser Arg Trp Gly Tyr Tyr Gly Lys Ser Ala Met Asp Tyr Trp Gly Gln
                100                 105                 110

Gly Thr Ser Val Thr Val Ser Ser
            115                 120

<210> SEQ ID NO 18
<211> LENGTH: 107
<212> TYPE: PRT
<213> ORGANISM: Artificial Sequence
<220> FEATURE:
<223> OTHER INFORMATION: 13B18A Light Chain Variable Region

<400> SEQUENCE: 18

Ala Val Gln Ile Thr Gln Phe Pro Ser Tyr Leu Ala Ala Ser Pro Gly
 1               5                  10                  15

Gln Thr Ile Thr Ile Asn Cys Arg Ala Ser Lys Ser Ile Ser Lys Tyr
                20                  25                  30

Leu Ala Trp Tyr Gln Glu Lys Pro Gly Lys Thr Asn Lys Leu Leu Ile
             35                  40                  45

Tyr Ser Gly Ser Thr Leu Gln Ser Gly Ile Pro Ser Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Met Tyr Tyr Cys Gln Gln His Asn Glu Tyr Pro Trp
                 85                  90                  95

Thr Phe Gly Gly Gly Thr Lys Leu Glu Ile Lys
                100                 105

<210> SEQ ID NO 19
<211> LENGTH: 117
<212> TYPE: PRT
<213> ORGANISM: Artificial Sequence
```

```
<220> FEATURE:
<223> OTHER INFORMATION: 1J7A Heavy Chain Variable Region

<400> SEQUENCE: 19

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Asn Ile Asp Pro Ser Asp Ser Glu Thr His Tyr Asn Gln Lys Phe
    50                  55                  60

Arg Asp Lys Ala Thr Leu Thr Val Asp Lys Ser Ser Asn Thr Ala Tyr
65                  70                  75                  80

Met Gln Leu Ser Ser Leu Thr Ser Glu Asp Ser Ala Val Tyr Tyr Cys
                85                  90                  95

Ala Arg Trp Gly Leu Arg Gly Ala Met Asp Tyr Trp Gly Gln Gly Thr
            100                 105                 110

Ser Val Thr Val Ser
        115

<210> SEQ ID NO 20
<211> LENGTH: 107
<212> TYPE: PRT
<213> ORGANISM: Artificial Sequence
<220> FEATURE:
<223> OTHER INFORMATION: 1J7A Light Chain Variable Region

<400> SEQUENCE: 20

Asp Val Gln Ile Thr Gln Ser Pro Thr Tyr Leu Thr Ala Ser Pro Gly
1               5                   10                  15

Glu Thr Ile Thr Ile Asn Cys Arg Ala Asn Lys Ser Ile Ser Lys Tyr
            20                  25                  30

Leu Ala Trp Tyr Gln Glu Lys Pro Gly Lys Thr Asn Lys Leu Leu Ile
        35                  40                  45

Tyr Ser Gly Ser Thr Leu Gln Ser Gly Ile Pro Ser Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Met Tyr Tyr Cys Gln Gln His Asn Glu Tyr Pro Trp
                85                  90                  95

Thr Phe Gly Gly Gly Thr Lys Leu Glu Ile Lys
            100                 105

<210> SEQ ID NO 21
<211> LENGTH: 120
<212> TYPE: PRT
<213> ORGANISM: Artificial Sequence
<220> FEATURE:
<223> OTHER INFORMATION: 14D18A Heavy Chain Variable Region

<400> SEQUENCE: 21

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45
```

```
Gly Asn Ile Asp Pro Ser Asp Ser Glu Thr His Tyr Asn Gln Lys Phe
     50                  55                  60
Lys Asp Lys Ala Thr Leu Thr Val Asp Lys Ser Ser Thr Ala Tyr
 65                  70                  75                  80
Met Gln Leu Ser Ser Leu Thr Ser Glu Asp Ser Ala Val Tyr Tyr Cys
                 85                  90                  95
Ala Arg Trp Gly Tyr Tyr Gly Arg Ser Pro Leu Asp His Trp Gly Gln
            100                 105                 110
Gly Thr Thr Leu Thr Val Ser Ser
            115                 120
```

```
<210> SEQ ID NO 22
<211> LENGTH: 107
<212> TYPE: PRT
<213> ORGANISM: Artificial Sequence
<220> FEATURE:
<223> OTHER INFORMATION: 14D18A Light Chain Variable Region

<400> SEQUENCE: 22

Asp Val Gln Ile Thr Gln Ser Pro Ser Tyr Leu Ala Ala Ser Pro Gly
 1               5                  10                  15
Glu Thr Ile Thr Ile Asn Cys Arg Ala Ser Lys Ser Ile Ser Lys Tyr
             20                  25                  30
Leu Ala Trp Tyr Gln Glu Lys Pro Gly Lys Thr Asn Lys Leu Leu Ile
         35                  40                  45
Tyr Ser Gly Ser Thr Leu Gln Ser Gly Ile Pro Ser Arg Phe Ser Gly
 50                  55                  60
Ser Gly Ser Gly Thr Asp Phe Thr Leu Thr Ile Ser Ser Leu Glu Pro
 65                  70                  75                  80
Glu Asp Phe Ala Met Tyr Tyr Cys Gln Gln His Asn Glu Tyr Pro Trp
                 85                  90                  95
Thr Phe Gly Gly Gly Thr Lys Leu Glu Ile Lys
            100                 105
```

```
<210> SEQ ID NO 23
<211> LENGTH: 115
<212> TYPE: PRT
<213> ORGANISM: Artificial Sequence
<220> FEATURE:
<223> OTHER INFORMATION: 305A Heavy Chain Variable Region

<400> SEQUENCE: 23

Glu Val Lys Leu Val Glu Ser Gly Gly Gly Leu Val Gln Ser Gly Arg
 1               5                  10                  15
Ser Leu Arg Leu Ser Cys Ala Thr Ser Gly Phe Thr Phe Ser Asp Phe
             20                  25                  30
Tyr Met Glu Trp Val Arg Gln Ala Pro Gly Lys Gly Leu Glu Trp Ile
         35                  40                  45
Ala Ala Ser Arg Asn Lys Ala Asn Asp Tyr Thr Thr Glu Tyr Ser Ala
     50                  55                  60
Ser Val Lys Gly Arg Phe Ile Val Ser Arg Asp Thr Ser Gln Ser Ile
 65                  70                  75                  80
Leu Tyr Leu Gln Met Asn Ala Leu Arg Ala Glu Asp Thr Ala Ile Tyr
                 85                  90                  95
Tyr Cys Ala Arg Asp Thr Ala Tyr Trp Gly Gln Gly Thr Leu Val Thr
            100                 105                 110
Val Ser Ala
        115
```

<210> SEQ ID NO 24
<211> LENGTH: 112
<212> TYPE: PRT
<213> ORGANISM: Artificial Sequence
<220> FEATURE:
<223> OTHER INFORMATION: 305A Light Chain Variable Region

<400> SEQUENCE: 24

```
Asp Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Ser Gly Thr Lys Leu Glu Ile Lys
            100                 105                 110
```

<210> SEQ ID NO 25
<211> LENGTH: 114
<212> TYPE: PRT
<213> ORGANISM: Artificial Sequence
<220> FEATURE:
<223> OTHER INFORMATION: 17C6A Heavy Chain Variable Region

<400> SEQUENCE: 25

```
Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Asn Ile Asp Pro Ser Asp Ser Glu Thr His Tyr Asn Gln Lys Phe
    50                  55                  60

Lys Asp Lys Ala Thr Leu Thr Val Asp Lys Ser Ser Ser Thr Ala His
65                  70                  75                  80

Met Gln Leu Ser Ser Leu Thr Ser Glu Asp Ser Ala Val Tyr Tyr Cys
                85                  90                  95

Ala Gly Thr Asp Leu Ala Tyr Trp Gly Gln Gly Thr Leu Val Thr Val
            100                 105                 110

Ser Ala
```

<210> SEQ ID NO 26
<211> LENGTH: 107
<212> TYPE: PRT
<213> ORGANISM: Artificial Sequence
<220> FEATURE:
<223> OTHER INFORMATION: 17C6A Light Chain Variable Region

<400> SEQUENCE: 26

```
Asp Ile Gln Met Asn Gln Ser Pro Ser Ser Leu Ser Ala Ser Leu Gly
1               5                   10                  15

Asp Thr Ile Thr Ile Thr Cys His Ala Ser Gln Asn Ile Asn Val Trp
            20                  25                  30
```

```
Leu Ser Trp Tyr Gln Gln Lys Pro Gly Asn Ile Pro Lys Leu Leu Ile
            35                  40                  45

Tyr Lys Ala Ser Asn Leu His Thr Gly Val Pro Ser Arg Phe Ser Gly
        50                  55                  60

Ser Gly Ser Gly Thr Gly Phe Thr Leu Thr Ile Ser Ser Leu Gln Pro
65                  70                  75                  80

Glu Asp Ile Ala Thr Tyr Tyr Cys Gln Gln Gly Gln Ser Tyr Pro Trp
                85                  90                  95

Thr Phe Gly Gly Gly Thr Lys Leu Glu Ile Lys
                100                 105

<210> SEQ ID NO 27
<211> LENGTH: 114
<212> TYPE: PRT
<213> ORGANISM: Artificial Sequence
<220> FEATURE:
<223> OTHER INFORMATION: 14N13A Heavy Chain Variable Region

<400> SEQUENCE: 27

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Ile Phe Thr Ser Tyr
            20                  25                  30

Trp Met His Trp Val Lys Gln Arg Pro Gly Gln Gly Leu Glu Trp Ile
        35                  40                  45

Gly Asn Ile Asp Pro Ser Asp Ser Glu Thr His Tyr Asn Gln Lys Phe
    50                  55                  60

Lys Asp Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Lys Gly Phe Ser Asp Tyr Trp Gly Gln Gly Thr Thr Leu Thr Val
            100                 105                 110

Ser Ser

<210> SEQ ID NO 28
<211> LENGTH: 113
<212> TYPE: PRT
<213> ORGANISM: Artificial Sequence
<220> FEATURE:
<223> OTHER INFORMATION: 14N13A Light Chain Variable Region

<400> SEQUENCE: 28

Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Val Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95
```

Tyr Tyr Ser Tyr Pro Leu Thr Phe Gly Ala Gly Thr Lys Leu Glu Leu
            100                 105                 110

Lys

<210> SEQ ID NO 29
<211> LENGTH: 118
<212> TYPE: PRT
<213> ORGANISM: Artificial Sequence
<220> FEATURE:
<223> OTHER INFORMATION: 10I23A Heavy Chain Variable Region

<400> SEQUENCE: 29

Glu Val Gln Leu Gln Gln Ser Gly Ala Glu Leu Val Arg Pro Gly Ala
1               5                   10                  15

Ser Val Lys Leu Ser Cys Thr Ala Ser Gly Phe Asn Ile Lys Asp Ser
            20                  25                  30

Leu Met His Trp Val Lys Gln Arg Pro Glu Gln Gly Leu Glu Trp Ile
        35                  40                  45

Gly Trp Ile Asp Pro Glu Asp Gly Glu Thr Lys Cys Ala Pro Lys Phe
    50                  55                  60

Gln Asp Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Ile Tyr Tyr Cys
                85                  90                  95

Ala Val Ile Ser Thr Val Val Ala Pro Asp Tyr Trp Gly Gln Gly Thr
            100                 105                 110

Thr Leu Thr Val Ser Ser
        115

<210> SEQ ID NO 30
<211> LENGTH: 112
<212> TYPE: PRT
<213> ORGANISM: Artificial Sequence
<220> FEATURE:
<223> OTHER INFORMATION: 10I23A Light Chain Variable Region

<400> SEQUENCE: 30

Asp Val Val Met Thr Gln Thr Pro Leu Ser Leu Pro Val Ser Leu Gly
1               5                   10                  15

Val Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Trp Thr Phe Gly Gly Gly Thr Lys Leu Glu Ile Lys
            100                 105                 110

<210> SEQ ID NO 31
<211> LENGTH: 117
<212> TYPE: PRT
<213> ORGANISM: Artificial Sequence
<220> FEATURE:
<223> OTHER INFORMATION: 12B18A Heavy Chain Variable Region

<400> SEQUENCE: 31

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Gly Tyr
            20                  25                  30

Phe Met Asn Trp Val Lys Gln Ser His Gly Lys Ser Leu Glu Trp Ile
        35                  40                  45

Gly Arg Ile Asn Pro Tyr Asn Gly Asp Thr Phe Tyr Asn Gln Lys Phe
    50                  55                  60

Lys Gly Lys Ala Thr Leu Thr Val Asp Lys Ser Ser Thr Ala His
65                  70                  75                  80

Met Glu Leu Arg Ser Leu Thr Ser Glu Asp Ser Ala Ile Tyr Tyr Cys
                85                  90                  95

Ala Arg Gly Gly Val Val Ala Thr Asp Tyr Trp Gly Gln Gly Thr Thr
            100                 105                 110

Leu Thr Val Ser Ser
            115

<210> SEQ ID NO 32
<211> LENGTH: 112
<212> TYPE: PRT
<213> ORGANISM: Artificial Sequence
<220> FEATURE:
<223> OTHER INFORMATION: 12B18A Light Chain Variable Region

<400> SEQUENCE: 32

Asp Val Val Met Thr Gln Thr Pro Val Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Arg Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Phe Thr Phe Gly Ser Gly Thr Lys Leu Glu Ile Lys
            100                 105                 110

<210> SEQ ID NO 33
<211> LENGTH: 116
<212> TYPE: PRT
<213> ORGANISM: Artificial Sequence
<220> FEATURE:
<223> OTHER INFORMATION: 17O12A Heavy Chain Variable Region

<400> SEQUENCE: 33

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Gly Tyr
            20                  25                  30

Phe Met His Trp Val Lys Gln Ser His Gly Lys Ser Leu Glu Trp Ile
        35                  40                  45

Gly Arg Ile Asn Pro Tyr Asn Gly Asp Thr Phe Asn Asn Gln Lys Phe
    50                  55                  60

```
Lys Gly Lys Ala Thr Leu Ala Val Asp Lys Ser Ser Ser Thr Ala His
 65                  70                  75                  80

Met Glu Leu Arg Ser Leu Thr Ser Glu Asp Ser Thr Val Tyr Tyr Cys
                 85                  90                  95

Ala Arg Gly Gly Tyr Ala Met Asp Tyr Trp Gly Gln Gly Thr Ser Val
            100                 105                 110

Thr Val Ser Ser
        115

<210> SEQ ID NO 34
<211> LENGTH: 112
<212> TYPE: PRT
<213> ORGANISM: Artificial Sequence
<220> FEATURE:
<223> OTHER INFORMATION: 17O12A Light Chain Variable Region

<400> SEQUENCE: 34

Asp Val Val Met Thr Gln Thr Pro Leu Ser Leu Pro Val Ser Leu Gly
 1               5                  10                  15

Asp Gln Ala Ser Ile Ser Cys Arg Ser Ser Gln Ser Leu Val His Ser
                20                  25                  30

Asn Gly Asn Thr Tyr Leu Tyr Trp Tyr Leu Gln Lys Pro Gly Gln Ser
            35                  40                  45

Pro Lys Leu Leu Ile Tyr Arg Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Phe Cys Phe Gln Ser
                 85                  90                  95

Thr His Val Pro His Thr Phe Gly Gly Gly Thr Lys Leu Glu Ile Lys
            100                 105                 110

<210> SEQ ID NO 35
<211> LENGTH: 117
<212> TYPE: PRT
<213> ORGANISM: Artificial Sequence
<220> FEATURE:
<223> OTHER INFORMATION: 15G23A Heavy Chain Variable Region

<400> SEQUENCE: 35

Glu Val Gln Leu Gln Gln Ser Gly Pro Glu Leu Val Lys Pro Gly Ala
 1               5                  10                  15

Ser Val Lys Met Ser Cys Lys Ala Ser Gly Tyr Thr Phe Thr Asn Tyr
                20                  25                  30

Val Ile His Trp Val Lys Gln Lys Pro Gly Gln Gly Leu Glu Trp Ile
            35                  40                  45

Gly Tyr Ile Asn Pro Tyr Asn Asp Gly Thr Lys Tyr Asn Glu Lys Phe
 50                  55                  60

Lys Gly Lys Ala Thr Leu Thr Ser Asp Lys Ser Ser Ser Thr Ala Tyr
 65                  70                  75                  80

Met Glu Leu Ser Ser Leu Thr Ser Glu Asp Ser Ala Val Tyr Tyr Cys
                 85                  90                  95

Ala Lys Gly Gly Thr Gly Thr Gly Asp Tyr Trp Gly Gln Gly Thr Thr
            100                 105                 110

Leu Thr Val Ser Ser
        115
```

<210> SEQ ID NO 36
<211> LENGTH: 113
<212> TYPE: PRT
<213> ORGANISM: Artificial Sequence
<220> FEATURE:
<223> OTHER INFORMATION: 15G23A Light Chain Variable Region

<400> SEQUENCE: 36

```
Asp Val Val Met Thr Gln Thr Pro Leu Ser Leu Pro Val Ser Leu Gly
1               5                   10                  15

Asp Gln Ala Ser Ile Ser Cys Arg Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Pro Leu Thr Phe Gly Ala Gly Thr Lys Leu Glu Leu
            100                 105                 110

Lys
```

<210> SEQ ID NO 37
<211> LENGTH: 119
<212> TYPE: PRT
<213> ORGANISM: Artificial Sequence
<220> FEATURE:
<223> OTHER INFORMATION: 17N8A Heavy Chain Variable Region

<400> SEQUENCE: 37

```
Glu Val Lys Leu Glu Glu Ser Gly Gly Gly Met Val Gln Pro Gly Gly
1               5                   10                  15

Ser Met Lys Val Ser Cys Val Ala Ser Gly Phe Thr Phe Ser Asn Tyr
            20                  25                  30

Trp Met Asn Trp Val Arg Gln Ser Pro Glu Lys Gly Leu Glu Trp Val
        35                  40                  45

Ala Gln Ile Arg Leu Lys Ser Asp Asn Tyr Ala Thr His Tyr Ala Glu
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Ala Glu Asp Thr Gly Ile Tyr
                85                  90                  95

Tyr Cys Thr Gly Gly Gly Lys Gly Gly Phe Ala Tyr Trp Gly Gln Gly
            100                 105                 110

Thr Leu Val Thr Val Ser Ala
        115
```

<210> SEQ ID NO 38
<211> LENGTH: 112
<212> TYPE: PRT
<213> ORGANISM: Artificial Sequence
<220> FEATURE:
<223> OTHER INFORMATION: 17N8A Light Chain Variable Region

```
<400> SEQUENCE: 38

Asp Val Val Met Thr Gln Thr Pro Leu Ser Leu Pro Val Ser Leu Gly
1               5                   10                  15

Asp Gln Ala Ser Ile Ser Cys Arg Ser Thr Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Leu Thr Phe Gly Ala Gly Thr Lys Leu Glu Leu Lys
            100                 105                 110

<210> SEQ ID NO 39
<211> LENGTH: 117
<212> TYPE: PRT
<213> ORGANISM: Artificial Sequence
<220> FEATURE:
<223> OTHER INFORMATION: 18M19A Heavy Chain Variable Region

<400> SEQUENCE: 39

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Val Met His Trp Val Lys Gln Lys Pro Gly Gln Gly Leu Glu Trp Ile
        35                  40                  45

Gly Tyr Ile Asn Pro Tyr Asn Asp Gly Thr Lys Tyr Asn Glu Lys Phe
    50                  55                  60

Lys Gly Lys Ala Thr Leu Thr Ser Asp Lys Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Lys Gly Gly Tyr Tyr Ala Met Asp Tyr Trp Gly Gln Gly Thr Ser
            100                 105                 110

Val Thr Val Ser Ser
        115

<210> SEQ ID NO 40
<211> LENGTH: 112
<212> TYPE: PRT
<213> ORGANISM: Artificial Sequence
<220> FEATURE:
<223> OTHER INFORMATION: 18M19 Light Chain Variable Region

<400> SEQUENCE: 40

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60
```

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Trp Thr Phe Gly Gly Gly Thr Lys Leu Glu Ile Lys
            100                 105                 110

<210> SEQ ID NO 41
<211> LENGTH: 118
<212> TYPE: PRT
<213> ORGANISM: Artificial Sequence
<220> FEATURE:
<223> OTHER INFORMATION: 11F6 Heavy Chain Variable Region

<400> SEQUENCE: 41

Glu Val Gln Leu Gln Gln Ser Gly Ala Glu Leu Val Arg Pro Gly Ala
1               5                   10                  15

Ser Val Lys Leu Ser Cys Thr Ala Ser Gly Phe Asn Ile Lys Asp Ser
                20                  25                  30

Leu Met His Trp Val Lys Gln Arg Pro Glu Gln Gly Leu Glu Trp Ile
            35                  40                  45

Gly Trp Ile Asp Pro Glu Asp Gly Glu Thr Lys Cys Ala Pro Lys Phe
    50                  55                  60

Gln Asp Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Ile Tyr Tyr Cys
                85                  90                  95

Ala Arg Ile Thr Thr Val Val Ala Thr Asp Tyr Trp Gly Gln Gly Thr
            100                 105                 110

Thr Leu Thr Val Ser Ser
        115

<210> SEQ ID NO 42
<211> LENGTH: 112
<212> TYPE: PRT
<213> ORGANISM: Artificial Sequence
<220> FEATURE:
<223> OTHER INFORMATION: 11F6A Light Chain Variable Region

<400> SEQUENCE: 42

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
                20                  25                  30

Asn Gly Asn Thr Tyr Leu His Trp Tyr Leu Gln Lys Pro Gly Gln Ser
            35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Leu Thr Phe Gly Ala Gly Thr Lys Leu Glu Leu Lys
            100                 105                 110

<210> SEQ ID NO 43
<211> LENGTH: 117
<212> TYPE: PRT
<213> ORGANISM: Artificial Sequence

```
<220> FEATURE:
<223> OTHER INFORMATION: 19L14A Heavy Chain Variable Region

<400> SEQUENCE: 43
```

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Ile Asn Trp Val Lys Gln Arg Pro Gly Gln Gly Leu Glu Trp Ile
            35                  40                  45

Gly Asn Ser Asn Pro Gly Ser Ser Thr Asn Tyr Asn Glu Lys Phe
    50                  55                  60

Lys Ser Lys Ala Ile Leu Thr Val Asp Lys Ser Ser Thr Ala Tyr
65              70                  75                  80

Met Gln Leu Ser Ser Leu Thr Ser Asp Asp Ser Ala Val Tyr Tyr Cys
                85                  90                  95

Ala Arg Glu Gly Leu Arg Arg Phe Ala Tyr Trp Gly Gln Gly Thr Leu
            100                 105                 110

Val Thr Val Ser Ala
        115

```
<210> SEQ ID NO 44
<211> LENGTH: 108
<212> TYPE: PRT
<213> ORGANISM: Artificial Sequence
<220> FEATURE:
<223> OTHER INFORMATION: 19L14A Light Chain Variable Region

<400> SEQUENCE: 44
```

Glu Asn Val Leu Thr Gln Ser Pro Ala Ile Met Ser Ala Ser Pro Gly
1               5                   10                  15

Glu Lys Val Thr Met Thr Cys Arg Ala Ser Ser Ser Val Ser Ser Ser
            20                  25                  30

Tyr Leu His Trp Tyr Gln Gln Lys Ser Gly Ala Ser Pro Lys Leu Trp
            35                  40                  45

Ile Tyr Ser Thr Ser Asn Leu Ala Ser Gly Val Pro Ala Arg Phe Ser
        50                  55                  60

Gly Ser Gly Ser Gly Thr Ser Tyr Ser Leu Thr Ile Ser Ser Val Glu
65              70                  75                  80

Ala Glu Asp Ala Ala Thr Tyr Tyr Cys Gln Gln Tyr Ser Gly Tyr Pro
                85                  90                  95

Phe Thr Phe Gly Ser Gly Thr Lys Leu Glu Ile Lys
            100                 105

```
<210> SEQ ID NO 45
<211> LENGTH: 8
<212> TYPE: PRT
<213> ORGANISM: Artificial Sequence
<220> FEATURE:
<223> OTHER INFORMATION: 9O23A HC CDR1

<400> SEQUENCE: 45
```

Gly Tyr Thr Phe Thr Asp Tyr Tyr
1               5

```
<210> SEQ ID NO 46
<211> LENGTH: 8
<212> TYPE: PRT
<213> ORGANISM: Artificial Sequence
```

```
<220> FEATURE:
<223> OTHER INFORMATION: 9O23A HC CDR2

<400> SEQUENCE: 46

Ile Tyr Pro Gly Ser Gly Asn Thr
1               5

<210> SEQ ID NO 47
<211> LENGTH: 10
<212> TYPE: PRT
<213> ORGANISM: Artificial Sequence
<220> FEATURE:
<223> OTHER INFORMATION: 9O23A HC CDR3

<400> SEQUENCE: 47

Ala Arg Arg Gly Pro Trp Tyr Phe Asp Val
1               5                   10

<210> SEQ ID NO 48
<211> LENGTH: 8
<212> TYPE: PRT
<213> ORGANISM: Artificial Sequence
<220> FEATURE:
<223> OTHER INFORMATION: 14P6A HC CDR1

<400> SEQUENCE: 48

Gly Tyr Thr Phe Thr Ala Tyr Tyr
1               5

<210> SEQ ID NO 49
<211> LENGTH: 8
<212> TYPE: PRT
<213> ORGANISM: Artificial Sequence
<220> FEATURE:
<223> OTHER INFORMATION: 14P6A HC CDR2

<400> SEQUENCE: 49

Ile Tyr Pro Gly Ser Gly Asn Thr
1               5

<210> SEQ ID NO 50
<211> LENGTH: 10
<212> TYPE: PRT
<213> ORGANISM: Artificial Sequence
<220> FEATURE:
<223> OTHER INFORMATION: 14P6A HC CDR3

<400> SEQUENCE: 50

Ala Arg Arg Gly Pro Trp Tyr Phe Asp Val
1               5                   10

<210> SEQ ID NO 51
<211> LENGTH: 8
<212> TYPE: PRT
<213> ORGANISM: Artificial Sequence
<220> FEATURE:
<223> OTHER INFORMATION: 4M8A HC CDR1

<400> SEQUENCE: 51

Gly Tyr Thr Phe Thr Ser Tyr Trp
1               5

<210> SEQ ID NO 52
<211> LENGTH: 8
<212> TYPE: PRT
<213> ORGANISM: Artificial Sequence
```

```
<220> FEATURE:
<223> OTHER INFORMATION: 4M8A HC CDR2

<400> SEQUENCE: 52

Ile Asp Pro Ser Asp Ser Glu Thr
1               5

<210> SEQ ID NO 53
<211> LENGTH: 11
<212> TYPE: PRT
<213> ORGANISM: Artificial Sequence
<220> FEATURE:
<223> OTHER INFORMATION: 4M8A HC CDR3

<400> SEQUENCE: 53

Ala Arg Trp Gly Gly Trp Leu Pro Leu Asp Tyr
1               5                   10

<210> SEQ ID NO 54
<211> LENGTH: 8
<212> TYPE: PRT
<213> ORGANISM: Artificial Sequence
<220> FEATURE:
<223> OTHER INFORMATION: 16M17A HC CDR1

<400> SEQUENCE: 54

Gly Tyr Thr Phe Thr Asn Tyr Trp
1               5

<210> SEQ ID NO 55
<211> LENGTH: 8
<212> TYPE: PRT
<213> ORGANISM: Artificial Sequence
<220> FEATURE:
<223> OTHER INFORMATION: 16M17A HC CDR2

<400> SEQUENCE: 55

Ile Asp Pro Ser Asp Ser Glu Thr
1               5

<210> SEQ ID NO 56
<211> LENGTH: 12
<212> TYPE: PRT
<213> ORGANISM: Artificial Sequence
<220> FEATURE:
<223> OTHER INFORMATION: 16M17A HC CDR3

<400> SEQUENCE: 56

Ala Arg Met Ala Phe Ile Thr Thr Val Val Asp Tyr
1               5                   10

<210> SEQ ID NO 57
<211> LENGTH: 8
<212> TYPE: PRT
<213> ORGANISM: Artificial Sequence
<220> FEATURE:
<223> OTHER INFORMATION: 13C4A HC CDR1

<400> SEQUENCE: 57

Gly Tyr Thr Phe Thr Ser Tyr Trp
1               5

<210> SEQ ID NO 58
<211> LENGTH: 8
<212> TYPE: PRT
<213> ORGANISM: Artificial Sequence
```

-continued

```
<220> FEATURE:
<223> OTHER INFORMATION: 13C4A HC CDR2

<400> SEQUENCE: 58

Ile Asp Pro Ser Asp Ser Glu Thr
1               5

<210> SEQ ID NO 59
<211> LENGTH: 13
<212> TYPE: PRT
<213> ORGANISM: Artificial Sequence
<220> FEATURE:
<223> OTHER INFORMATION: 13C4A HC CDR3

<400> SEQUENCE: 59

Ala Arg Trp Gly Tyr Tyr Gly Arg Ser Pro Leu Asp His
1               5                   10

<210> SEQ ID NO 60
<211> LENGTH: 8
<212> TYPE: PRT
<213> ORGANISM: Artificial Sequence
<220> FEATURE:
<223> OTHER INFORMATION: 14O18A HC CDR1

<400> SEQUENCE: 60

Gly Tyr Thr Phe Thr Ser Tyr Trp
1               5

<210> SEQ ID NO 61
<211> LENGTH: 8
<212> TYPE: PRT
<213> ORGANISM: Artificial Sequence
<220> FEATURE:
<223> OTHER INFORMATION: 14O18A HC CDR2

<400> SEQUENCE: 61

Ile Asp Pro Ser Asp Ser Glu Thr
1               5

<210> SEQ ID NO 62
<211> LENGTH: 13
<212> TYPE: PRT
<213> ORGANISM: Artificial Sequence
<220> FEATURE:
<223> OTHER INFORMATION: 14O18A HC CDR3

<400> SEQUENCE: 62

Ala Arg Trp Tyr Tyr Gly Gly Ser Gly Ala Met Asp Tyr
1               5                   10

<210> SEQ ID NO 63
<211> LENGTH: 8
<212> TYPE: PRT
<213> ORGANISM: Artificial Sequence
<220> FEATURE:
<223> OTHER INFORMATION: 5D24A HC CDR1

<400> SEQUENCE: 63

Gly Tyr Thr Phe Thr Ser Ser Trp
1               5

<210> SEQ ID NO 64
<211> LENGTH: 8
<212> TYPE: PRT
<213> ORGANISM: Artificial Sequence
```

```
<220> FEATURE:
<223> OTHER INFORMATION: 5D24A HC CDR2

<400> SEQUENCE: 64

Ile Asp Pro Ser Asp Ser Glu Thr
1               5

<210> SEQ ID NO 65
<211> LENGTH: 13
<212> TYPE: PRT
<213> ORGANISM: Artificial Sequence
<220> FEATURE:
<223> OTHER INFORMATION: 5D24A HC CDR3

<400> SEQUENCE: 65

Ala Arg Trp Gly Tyr Tyr Gly Lys Ser Ala Ile Asp Tyr
1               5                   10

<210> SEQ ID NO 66
<211> LENGTH: 8
<212> TYPE: PRT
<213> ORGANISM: Artificial Sequence
<220> FEATURE:
<223> OTHER INFORMATION: 11G2A HC CDR1

<400> SEQUENCE: 66

Gly Tyr Thr Phe Thr Ser Tyr Trp
1               5

<210> SEQ ID NO 67
<211> LENGTH: 8
<212> TYPE: PRT
<213> ORGANISM: Artificial Sequence
<220> FEATURE:
<223> OTHER INFORMATION: 11G2A HC CDR2

<400> SEQUENCE: 67

Ile Asp Pro Ser Asp Ser Glu Ala
1               5

<210> SEQ ID NO 68
<211> LENGTH: 13
<212> TYPE: PRT
<213> ORGANISM: Artificial Sequence
<220> FEATURE:
<223> OTHER INFORMATION: 11G2A HC CDR3

<400> SEQUENCE: 68

Ala Arg Trp Gly Tyr Tyr Gly Lys Ser Ala Met Asp Tyr
1               5                   10

<210> SEQ ID NO 69
<211> LENGTH: 8
<212> TYPE: PRT
<213> ORGANISM: Artificial Sequence
<220> FEATURE:
<223> OTHER INFORMATION: 13B18A HC CDR1

<400> SEQUENCE: 69

Gly Tyr Thr Phe Thr Ser Tyr Trp
1               5

<210> SEQ ID NO 70
<211> LENGTH: 8
<212> TYPE: PRT
<213> ORGANISM: Artificial Sequence
```

```
<220> FEATURE:
<223> OTHER INFORMATION: 13B18A HC CDR2

<400> SEQUENCE: 70

Ile Asp Pro Ser Asp Ser Glu Thr
1               5

<210> SEQ ID NO 71
<211> LENGTH: 13
<212> TYPE: PRT
<213> ORGANISM: Artificial Sequence
<220> FEATURE:
<223> OTHER INFORMATION: 13B18A HC CDR3

<400> SEQUENCE: 71

Ser Arg Trp Gly Tyr Tyr Gly Lys Ser Ala Met Asp Tyr
1               5                   10

<210> SEQ ID NO 72
<211> LENGTH: 8
<212> TYPE: PRT
<213> ORGANISM: Artificial Sequence
<220> FEATURE:
<223> OTHER INFORMATION: 1J7A HC CDR1

<400> SEQUENCE: 72

Gly Tyr Thr Phe Thr Ser Tyr Trp
1               5

<210> SEQ ID NO 73
<211> LENGTH: 8
<212> TYPE: PRT
<213> ORGANISM: Artificial Sequence
<220> FEATURE:
<223> OTHER INFORMATION: 1J7A HC CDR2

<400> SEQUENCE: 73

Ile Asp Pro Ser Asp Ser Glu Thr
1               5

<210> SEQ ID NO 74
<211> LENGTH: 11
<212> TYPE: PRT
<213> ORGANISM: Artificial Sequence
<220> FEATURE:
<223> OTHER INFORMATION: 1J7A HC CDR3

<400> SEQUENCE: 74

Ala Arg Trp Gly Leu Arg Gly Ala Met Asp Tyr
1               5                   10

<210> SEQ ID NO 75
<211> LENGTH: 8
<212> TYPE: PRT
<213> ORGANISM: Artificial Sequence
<220> FEATURE:
<223> OTHER INFORMATION: 14D18A HC CDR1

<400> SEQUENCE: 75

Gly Tyr Thr Phe Thr Ser Tyr Trp
1               5

<210> SEQ ID NO 76
<211> LENGTH: 8
<212> TYPE: PRT
<213> ORGANISM: Artificial Sequence
```

```
<220> FEATURE:
<223> OTHER INFORMATION: 14D18A HC CDR2

<400> SEQUENCE: 76

Ile Asp Pro Ser Asp Ser Glu Thr
1               5

<210> SEQ ID NO 77
<211> LENGTH: 13
<212> TYPE: PRT
<213> ORGANISM: Artificial Sequence
<220> FEATURE:
<223> OTHER INFORMATION: 14D18A HC CDR3

<400> SEQUENCE: 77

Ala Arg Trp Gly Tyr Tyr Gly Arg Ser Pro Leu Asp His
1               5                   10

<210> SEQ ID NO 78
<211> LENGTH: 8
<212> TYPE: PRT
<213> ORGANISM: Artificial Sequence
<220> FEATURE:
<223> OTHER INFORMATION: 3O5A HC CDR1

<400> SEQUENCE: 78

Gly Phe Thr Phe Ser Asp Phe Tyr
1               5

<210> SEQ ID NO 79
<211> LENGTH: 10
<212> TYPE: PRT
<213> ORGANISM: Artificial Sequence
<220> FEATURE:
<223> OTHER INFORMATION: 3O5A HC CDR2

<400> SEQUENCE: 79

Ser Arg Asn Lys Ala Asn Asp Tyr Thr Thr
1               5                   10

<210> SEQ ID NO 80
<211> LENGTH: 6
<212> TYPE: PRT
<213> ORGANISM: Artificial Sequence
<220> FEATURE:
<223> OTHER INFORMATION: 3O5A HC CDR3

<400> SEQUENCE: 80

Ala Arg Asp Thr Ala Tyr
1               5

<210> SEQ ID NO 81
<211> LENGTH: 8
<212> TYPE: PRT
<213> ORGANISM: Artificial Sequence
<220> FEATURE:
<223> OTHER INFORMATION: 17C6A HC CDR1

<400> SEQUENCE: 81

Gly Tyr Thr Phe Thr Ser Tyr Trp
1               5

<210> SEQ ID NO 82
<211> LENGTH: 8
<212> TYPE: PRT
<213> ORGANISM: Artificial Sequence
```

```
<220> FEATURE:
<223> OTHER INFORMATION: 17C6A HC CDR2

<400> SEQUENCE: 82

Ile Asp Pro Ser Asp Ser Glu Thr
1               5

<210> SEQ ID NO 83
<211> LENGTH: 7
<212> TYPE: PRT
<213> ORGANISM: Artificial Sequence
<220> FEATURE:
<223> OTHER INFORMATION: 17C6A HC CDR3

<400> SEQUENCE: 83

Ala Gly Thr Asp Leu Ala Tyr
1               5

<210> SEQ ID NO 84
<211> LENGTH: 8
<212> TYPE: PRT
<213> ORGANISM: Artificial Sequence
<220> FEATURE:
<223> OTHER INFORMATION: 14N13A HC CDR1

<400> SEQUENCE: 84

Gly Tyr Ile Phe Thr Ser Tyr Trp
1               5

<210> SEQ ID NO 85
<211> LENGTH: 8
<212> TYPE: PRT
<213> ORGANISM: Artificial Sequence
<220> FEATURE:
<223> OTHER INFORMATION: 14N13A HC CDR2

<400> SEQUENCE: 85

Ile Asp Pro Ser Asp Ser Glu Thr
1               5

<210> SEQ ID NO 86
<211> LENGTH: 7
<212> TYPE: PRT
<213> ORGANISM: Artificial Sequence
<220> FEATURE:
<223> OTHER INFORMATION: 14N13A HC CDR3

<400> SEQUENCE: 86

Ala Lys Gly Phe Ser Asp Tyr
1               5

<210> SEQ ID NO 87
<211> LENGTH: 8
<212> TYPE: PRT
<213> ORGANISM: Artificial Sequence
<220> FEATURE:
<223> OTHER INFORMATION: 10I23A HC CDR1

<400> SEQUENCE: 87

Gly Phe Asn Ile Lys Asp Ser Leu
1               5

<210> SEQ ID NO 88
<211> LENGTH: 8
<212> TYPE: PRT
<213> ORGANISM: Artificial Sequence
```

```
<220> FEATURE:
<223> OTHER INFORMATION: 10I23A HC CDR2

<400> SEQUENCE: 88

Ile Asp Pro Glu Asp Gly Glu Thr
1               5

<210> SEQ ID NO 89
<211> LENGTH: 11
<212> TYPE: PRT
<213> ORGANISM: Artificial Sequence
<220> FEATURE:
<223> OTHER INFORMATION: 10I23A HC CDR3

<400> SEQUENCE: 89

Ala Val Ile Ser Thr Val Val Ala Pro Asp Tyr
1               5                   10

<210> SEQ ID NO 90
<211> LENGTH: 8
<212> TYPE: PRT
<213> ORGANISM: Artificial Sequence
<220> FEATURE:
<223> OTHER INFORMATION: 12B18A HC CDR1

<400> SEQUENCE: 90

Gly Tyr Ser Phe Thr Gly Tyr Phe
1               5

<210> SEQ ID NO 91
<211> LENGTH: 8
<212> TYPE: PRT
<213> ORGANISM: Artificial Sequence
<220> FEATURE:
<223> OTHER INFORMATION: 12B18A HC CDR2

<400> SEQUENCE: 91

Ile Asn Pro Tyr Asn Gly Asp Thr
1               5

<210> SEQ ID NO 92
<211> LENGTH: 10
<212> TYPE: PRT
<213> ORGANISM: Artificial Sequence
<220> FEATURE:
<223> OTHER INFORMATION: 12B18A HC CDR3

<400> SEQUENCE: 92

Ala Arg Gly Gly Val Val Ala Thr Asp Tyr
1               5                   10

<210> SEQ ID NO 93
<211> LENGTH: 8
<212> TYPE: PRT
<213> ORGANISM: Artificial Sequence
<220> FEATURE:
<223> OTHER INFORMATION: 17O12A HC CDR1

<400> SEQUENCE: 93

Gly Tyr Ser Phe Thr Gly Tyr Phe
1               5

<210> SEQ ID NO 94
<211> LENGTH: 8
<212> TYPE: PRT
<213> ORGANISM: Artificial Sequence
```

-continued

```
<220> FEATURE:
<223> OTHER INFORMATION: 17O12A HC CDR2

<400> SEQUENCE: 94

Ile Asn Pro Tyr Asn Gly Asp Thr
1               5

<210> SEQ ID NO 95
<211> LENGTH: 9
<212> TYPE: PRT
<213> ORGANISM: Artificial Sequence
<220> FEATURE:
<223> OTHER INFORMATION: 17O12A HC CDR3

<400> SEQUENCE: 95

Ala Arg Gly Gly Tyr Ala Met Asp Tyr
1               5

<210> SEQ ID NO 96
<211> LENGTH: 8
<212> TYPE: PRT
<213> ORGANISM: Artificial Sequence
<220> FEATURE:
<223> OTHER INFORMATION: 15G23A HC CDR1

<400> SEQUENCE: 96

Gly Tyr Thr Phe Thr Asn Tyr Val
1               5

<210> SEQ ID NO 97
<211> LENGTH: 8
<212> TYPE: PRT
<213> ORGANISM: Artificial Sequence
<220> FEATURE:
<223> OTHER INFORMATION: 15G23A HC CDR2

<400> SEQUENCE: 97

Ile Asn Pro Tyr Asn Asp Gly Thr
1               5

<210> SEQ ID NO 98
<211> LENGTH: 10
<212> TYPE: PRT
<213> ORGANISM: Artificial Sequence
<220> FEATURE:
<223> OTHER INFORMATION: 15G23A HC CDR3

<400> SEQUENCE: 98

Ala Lys Gly Gly Thr Gly Thr Gly Asp Tyr
1               5                   10

<210> SEQ ID NO 99
<211> LENGTH: 8
<212> TYPE: PRT
<213> ORGANISM: Artificial Sequence
<220> FEATURE:
<223> OTHER INFORMATION: 17N8A HC CDR1

<400> SEQUENCE: 99

Gly Phe Thr Phe Ser Asn Tyr Trp
1               5

<210> SEQ ID NO 100
<211> LENGTH: 10
<212> TYPE: PRT
<213> ORGANISM: Artificial Sequence
```

```
<220> FEATURE:
<223> OTHER INFORMATION: 17N8A HC CDR2

<400> SEQUENCE: 100

Ile Arg Leu Lys Ser Asp Asn Tyr Ala Thr
1               5                   10

<210> SEQ ID NO 101
<211> LENGTH: 10
<212> TYPE: PRT
<213> ORGANISM: Artificial Sequence
<220> FEATURE:
<223> OTHER INFORMATION: 17N8A HC CDR3

<400> SEQUENCE: 101

Thr Gly Gly Gly Lys Gly Gly Phe Ala Tyr
1               5                   10

<210> SEQ ID NO 102
<211> LENGTH: 8
<212> TYPE: PRT
<213> ORGANISM: Artificial Sequence
<220> FEATURE:
<223> OTHER INFORMATION: 18M19A HC CDR1

<400> SEQUENCE: 102

Gly Tyr Thr Phe Thr Ser Tyr Val
1               5

<210> SEQ ID NO 103
<211> LENGTH: 8
<212> TYPE: PRT
<213> ORGANISM: Artificial Sequence
<220> FEATURE:
<223> OTHER INFORMATION: 18M19A HC CDR2

<400> SEQUENCE: 103

Ile Asn Pro Tyr Asn Asp Gly Thr
1               5

<210> SEQ ID NO 104
<211> LENGTH: 10
<212> TYPE: PRT
<213> ORGANISM: Artificial Sequence
<220> FEATURE:
<223> OTHER INFORMATION: 18M19A HC CDR3

<400> SEQUENCE: 104

Ala Lys Gly Gly Tyr Tyr Ala Met Asp Tyr
1               5                   10

<210> SEQ ID NO 105
<211> LENGTH: 8
<212> TYPE: PRT
<213> ORGANISM: Artificial Sequence
<220> FEATURE:
<223> OTHER INFORMATION: 11F6A HC CDR1

<400> SEQUENCE: 105

Gly Phe Asn Ile Lys Asp Ser Leu
1               5

<210> SEQ ID NO 106
<211> LENGTH: 8
<212> TYPE: PRT
<213> ORGANISM: Artificial Sequence
```

```
<220> FEATURE:
<223> OTHER INFORMATION: 11F6A HC CDR2

<400> SEQUENCE: 106

Ile Asp Pro Glu Asp Gly Glu Thr
1               5

<210> SEQ ID NO 107
<211> LENGTH: 11
<212> TYPE: PRT
<213> ORGANISM: Artificial Sequence
<220> FEATURE:
<223> OTHER INFORMATION: 11F6A HC CDR3

<400> SEQUENCE: 107

Ala Arg Ile Thr Thr Val Val Ala Thr Asp Tyr
1               5                   10

<210> SEQ ID NO 108
<211> LENGTH: 8
<212> TYPE: PRT
<213> ORGANISM: Artificial Sequence
<220> FEATURE:
<223> OTHER INFORMATION: 19L14A HC CDR1

<400> SEQUENCE: 108

Gly Tyr Thr Phe Thr Ser Tyr Trp
1               5

<210> SEQ ID NO 109
<211> LENGTH: 8
<212> TYPE: PRT
<213> ORGANISM: Artificial Sequence
<220> FEATURE:
<223> OTHER INFORMATION: 19L14A HC CDR2

<400> SEQUENCE: 109

Ser Asn Pro Gly Ser Ser Ser Thr
1               5

<210> SEQ ID NO 110
<211> LENGTH: 10
<212> TYPE: PRT
<213> ORGANISM: Artificial Sequence
<220> FEATURE:
<223> OTHER INFORMATION: 19L14A HC CDR3

<400> SEQUENCE: 110

Ala Arg Glu Gly Leu Arg Arg Phe Ala Tyr
1               5                   10

<210> SEQ ID NO 111
<211> LENGTH: 6
<212> TYPE: PRT
<213> ORGANISM: Artificial Sequence
<220> FEATURE:
<223> OTHER INFORMATION: 9O23A LC CDR1

<400> SEQUENCE: 111

Asp Asn Val Gly Thr Tyr
1               5

<210> SEQ ID NO 112
<211> LENGTH: 3
<212> TYPE: PRT
<213> ORGANISM: Artificial Sequence
```

```
<220> FEATURE:
<223> OTHER INFORMATION: 9O23A LC CDR2

<400> SEQUENCE: 112

Gly Ala Ser
1

<210> SEQ ID NO 113
<211> LENGTH: 9
<212> TYPE: PRT
<213> ORGANISM: Artificial Sequence
<220> FEATURE:
<223> OTHER INFORMATION: 9O23A LC CDR3

<400> SEQUENCE: 113

Gly Gln Ser Tyr Ser Tyr Pro Leu Thr
1               5

<210> SEQ ID NO 114
<211> LENGTH: 6
<212> TYPE: PRT
<213> ORGANISM: Artificial Sequence
<220> FEATURE:
<223> OTHER INFORMATION: 14P6A LC CDR1

<400> SEQUENCE: 114

Glu Asn Val Gly Thr Tyr
1               5

<210> SEQ ID NO 115
<211> LENGTH: 3
<212> TYPE: PRT
<213> ORGANISM: Artificial Sequence
<220> FEATURE:
<223> OTHER INFORMATION: 14P6A LC CDR2

<400> SEQUENCE: 115

Gly Ala Ser
1

<210> SEQ ID NO 116
<211> LENGTH: 9
<212> TYPE: PRT
<213> ORGANISM: Artificial Sequence
<220> FEATURE:
<223> OTHER INFORMATION: 14P6A LC CDR3

<400> SEQUENCE: 116

Gly Gln Thr Tyr Ser Tyr Pro Leu Thr
1               5

<210> SEQ ID NO 117
<211> LENGTH: 6
<212> TYPE: PRT
<213> ORGANISM: Artificial Sequence
<220> FEATURE:
<223> OTHER INFORMATION: 4M8A LC CDR1

<400> SEQUENCE: 117

Lys Asn Ile Ser Lys Tyr
1               5

<210> SEQ ID NO 118
<211> LENGTH: 3
<212> TYPE: PRT
<213> ORGANISM: Artificial Sequence
```

```
<220> FEATURE:
<223> OTHER INFORMATION: 4M8A LC CDR2

<400> SEQUENCE: 118

Ser Gly Ser
1

<210> SEQ ID NO 119
<211> LENGTH: 9
<212> TYPE: PRT
<213> ORGANISM: Artificial Sequence
<220> FEATURE:
<223> OTHER INFORMATION: 4M8A LC CDR3

<400> SEQUENCE: 119

Gln Gln His Asn Glu Tyr Pro Trp Thr
1               5

<210> SEQ ID NO 120
<211> LENGTH: 6
<212> TYPE: PRT
<213> ORGANISM: Artificial Sequence
<220> FEATURE:
<223> OTHER INFORMATION: 16M17A LC CDR1

<400> SEQUENCE: 120

Lys Ser Ile Ser Lys Tyr
1               5

<210> SEQ ID NO 121
<211> LENGTH: 3
<212> TYPE: PRT
<213> ORGANISM: Artificial Sequence
<220> FEATURE:
<223> OTHER INFORMATION: 16M17A LC CDR2

<400> SEQUENCE: 121

Ser Gly Ser
1

<210> SEQ ID NO 122
<211> LENGTH: 9
<212> TYPE: PRT
<213> ORGANISM: Artificial Sequence
<220> FEATURE:
<223> OTHER INFORMATION: 16M17A LC CDR3

<400> SEQUENCE: 122

Gln Gln His Asn Glu Tyr Pro Trp Thr
1               5

<210> SEQ ID NO 123
<211> LENGTH: 6
<212> TYPE: PRT
<213> ORGANISM: Artificial Sequence
<220> FEATURE:
<223> OTHER INFORMATION: 13C4A LC CDR1

<400> SEQUENCE: 123

Lys Ser Ile Ser Lys Tyr
1               5

<210> SEQ ID NO 124
<211> LENGTH: 3
<212> TYPE: PRT
<213> ORGANISM: Artificial Sequence
```

```
<220> FEATURE:
<223> OTHER INFORMATION: 13C4A LC CDR2

<400> SEQUENCE: 124

Ser Gly Ser
1

<210> SEQ ID NO 125
<211> LENGTH: 9
<212> TYPE: PRT
<213> ORGANISM: Artificial Sequence
<220> FEATURE:
<223> OTHER INFORMATION: 13C4A LC CDR3

<400> SEQUENCE: 125

Gln Gln His Asn Glu Tyr Pro Trp Thr
1               5

<210> SEQ ID NO 126
<211> LENGTH: 6
<212> TYPE: PRT
<213> ORGANISM: Artificial Sequence
<220> FEATURE:
<223> OTHER INFORMATION: 14O18A LC CDR1

<400> SEQUENCE: 126

Lys Ser Ile Ser Lys Tyr
1               5

<210> SEQ ID NO 127
<211> LENGTH: 3
<212> TYPE: PRT
<213> ORGANISM: Artificial Sequence
<220> FEATURE:
<223> OTHER INFORMATION: 14O18A LC CDR2

<400> SEQUENCE: 127

Ser Gly Ser
1

<210> SEQ ID NO 128
<211> LENGTH: 9
<212> TYPE: PRT
<213> ORGANISM: Artificial Sequence
<220> FEATURE:
<223> OTHER INFORMATION: 14O18A LC CDR3

<400> SEQUENCE: 128

Gln Gln His Asn Glu Tyr Pro Trp Thr
1               5

<210> SEQ ID NO 129
<211> LENGTH: 6
<212> TYPE: PRT
<213> ORGANISM: Artificial Sequence
<220> FEATURE:
<223> OTHER INFORMATION: 5D24A LC CDR1

<400> SEQUENCE: 129

Lys Ser Ile Ser Lys Tyr
1               5

<210> SEQ ID NO 130
<211> LENGTH: 3
<212> TYPE: PRT
<213> ORGANISM: Artificial Sequence
```

```
<220> FEATURE:
<223> OTHER INFORMATION: 5D24A LC CDR2

<400> SEQUENCE: 130

Ser Gly Ser
1

<210> SEQ ID NO 131
<211> LENGTH: 9
<212> TYPE: PRT
<213> ORGANISM: Artificial Sequence
<220> FEATURE:
<223> OTHER INFORMATION: 5D24A LC CDR3

<400> SEQUENCE: 131

Gln Gln His Asn Glu Tyr Pro Trp Thr
1               5

<210> SEQ ID NO 132
<211> LENGTH: 6
<212> TYPE: PRT
<213> ORGANISM: Artificial Sequence
<220> FEATURE:
<223> OTHER INFORMATION: 11G2A LC CDR1

<400> SEQUENCE: 132

Lys Ser Ile Ser Lys Tyr
1               5

<210> SEQ ID NO 133
<211> LENGTH: 3
<212> TYPE: PRT
<213> ORGANISM: Artificial Sequence
<220> FEATURE:
<223> OTHER INFORMATION: 11G2A LC CDR2

<400> SEQUENCE: 133

Ser Gly Ser
1

<210> SEQ ID NO 134
<211> LENGTH: 9
<212> TYPE: PRT
<213> ORGANISM: Artificial Sequence
<220> FEATURE:
<223> OTHER INFORMATION: 11G2A LC CDR3

<400> SEQUENCE: 134

Gln Gln His Asn Glu Tyr Pro Trp Thr
1               5

<210> SEQ ID NO 135
<211> LENGTH: 6
<212> TYPE: PRT
<213> ORGANISM: Artificial Sequence
<220> FEATURE:
<223> OTHER INFORMATION: 13B18A LC CDR1

<400> SEQUENCE: 135

Lys Ser Ile Ser Lys Tyr
1               5

<210> SEQ ID NO 136
<211> LENGTH: 3
<212> TYPE: PRT
<213> ORGANISM: Artificial Sequence
```

```
<220> FEATURE:
<223> OTHER INFORMATION: 13B18A LC CDR2

<400> SEQUENCE: 136

Ser Gly Ser
1

<210> SEQ ID NO 137
<211> LENGTH: 9
<212> TYPE: PRT
<213> ORGANISM: Artificial Sequence
<220> FEATURE:
<223> OTHER INFORMATION: 13B18A LC CDR3

<400> SEQUENCE: 137

Gln Gln His Asn Glu Tyr Pro Trp Thr
1               5

<210> SEQ ID NO 138
<211> LENGTH: 6
<212> TYPE: PRT
<213> ORGANISM: Artificial Sequence
<220> FEATURE:
<223> OTHER INFORMATION: 1J7A LC CDR1

<400> SEQUENCE: 138

Lys Ser Ile Ser Lys Tyr
1               5

<210> SEQ ID NO 139
<211> LENGTH: 3
<212> TYPE: PRT
<213> ORGANISM: Artificial Sequence
<220> FEATURE:
<223> OTHER INFORMATION: 1J7A LC CDR2

<400> SEQUENCE: 139

Ser Gly Ser
1

<210> SEQ ID NO 140
<211> LENGTH: 9
<212> TYPE: PRT
<213> ORGANISM: Artificial Sequence
<220> FEATURE:
<223> OTHER INFORMATION: 1J7A LC CDR3

<400> SEQUENCE: 140

Gln Gln His Asn Glu Tyr Pro Trp Thr
1               5

<210> SEQ ID NO 141
<211> LENGTH: 6
<212> TYPE: PRT
<213> ORGANISM: Artificial Sequence
<220> FEATURE:
<223> OTHER INFORMATION: 14D18A LC CDR1

<400> SEQUENCE: 141

Lys Ser Ile Ser Lys Tyr
1               5

<210> SEQ ID NO 142
<211> LENGTH: 3
<212> TYPE: PRT
<213> ORGANISM: Artificial Sequence
```

```
<220> FEATURE:
<223> OTHER INFORMATION: 14D18A LC CDR2

<400> SEQUENCE: 142

Ser Gly Ser
1

<210> SEQ ID NO 143
<211> LENGTH: 9
<212> TYPE: PRT
<213> ORGANISM: Artificial Sequence
<220> FEATURE:
<223> OTHER INFORMATION: 14D18A LC CDR3

<400> SEQUENCE: 143

Gln Gln His Asn Glu Tyr Pro Trp Thr
1               5

<210> SEQ ID NO 144
<211> LENGTH: 11
<212> TYPE: PRT
<213> ORGANISM: Artificial Sequence
<220> FEATURE:
<223> OTHER INFORMATION: 3O5A LC CDR1

<400> SEQUENCE: 144

Lys Ser Leu Leu His Ser Asn Gly Asn Thr Tyr
1               5                   10

<210> SEQ ID NO 145
<211> LENGTH: 3
<212> TYPE: PRT
<213> ORGANISM: Artificial Sequence
<220> FEATURE:
<223> OTHER INFORMATION: 3O5A LC CDR2

<400> SEQUENCE: 145

Arg Met Ser
1

<210> SEQ ID NO 146
<211> LENGTH: 9
<212> TYPE: PRT
<213> ORGANISM: Artificial Sequence
<220> FEATURE:
<223> OTHER INFORMATION: 3O5A LC CDR3

<400> SEQUENCE: 146

Met Gln His Leu Glu Tyr Pro Phe Thr
1               5

<210> SEQ ID NO 147
<211> LENGTH: 6
<212> TYPE: PRT
<213> ORGANISM: Artificial Sequence
<220> FEATURE:
<223> OTHER INFORMATION: 17C6A LC CDR1

<400> SEQUENCE: 147

Gln Asn Ile Asn Val Trp
1               5

<210> SEQ ID NO 148
<211> LENGTH: 3
<212> TYPE: PRT
<213> ORGANISM: Artificial Sequence
```

<220> FEATURE:
<223> OTHER INFORMATION: 17C6A LC CDR2

<400> SEQUENCE: 148

Lys Ala Ser
1

<210> SEQ ID NO 149
<211> LENGTH: 9
<212> TYPE: PRT
<213> ORGANISM: Artificial Sequence
<220> FEATURE:
<223> OTHER INFORMATION: 17C6A LC CDR3

<400> SEQUENCE: 149

Gln Gln Gly Gln Ser Tyr Pro Trp Thr
1               5

<210> SEQ ID NO 150
<211> LENGTH: 12
<212> TYPE: PRT
<213> ORGANISM: Artificial Sequence
<220> FEATURE:
<223> OTHER INFORMATION: 14N13A LC CDR1

<400> SEQUENCE: 150

Gln Ser Leu Leu Tyr Ser Ser Asn Gln Lys Asn Tyr
1               5                   10

<210> SEQ ID NO 151
<211> LENGTH: 3
<212> TYPE: PRT
<213> ORGANISM: Artificial Sequence
<220> FEATURE:
<223> OTHER INFORMATION: 14N13A LC CDR2

<400> SEQUENCE: 151

Trp Ala Ser
1

<210> SEQ ID NO 152
<211> LENGTH: 9
<212> TYPE: PRT
<213> ORGANISM: Artificial Sequence
<220> FEATURE:
<223> OTHER INFORMATION: 14N13A LC CDR3

<400> SEQUENCE: 152

Gln Gln Tyr Tyr Ser Tyr Pro Leu Thr
1               5

<210> SEQ ID NO 153
<211> LENGTH: 11
<212> TYPE: PRT
<213> ORGANISM: Artificial Sequence
<220> FEATURE:
<223> OTHER INFORMATION: 10I23A LC CDR1

<400> SEQUENCE: 153

Gln Ser Leu Val His Ser Asn Gly Asn Thr Tyr
1               5                   10

<210> SEQ ID NO 154
<211> LENGTH: 3
<212> TYPE: PRT
<213> ORGANISM: Artificial Sequence

```
<220> FEATURE:
<223> OTHER INFORMATION: 10I23A LC CDR2

<400> SEQUENCE: 154

Lys Val Ser
1

<210> SEQ ID NO 155
<211> LENGTH: 9
<212> TYPE: PRT
<213> ORGANISM: Artificial Sequence
<220> FEATURE:
<223> OTHER INFORMATION: 10I23A LC CDR3

<400> SEQUENCE: 155

Ser Gln Ser Thr His Val Pro Trp Thr
1               5

<210> SEQ ID NO 156
<211> LENGTH: 11
<212> TYPE: PRT
<213> ORGANISM: Artificial Sequence
<220> FEATURE:
<223> OTHER INFORMATION: 12B18A LC CDR1

<400> SEQUENCE: 156

Gln Ser Leu Val His Ser Asn Gly Asn Thr Tyr
1               5                   10

<210> SEQ ID NO 157
<211> LENGTH: 3
<212> TYPE: PRT
<213> ORGANISM: Artificial Sequence
<220> FEATURE:
<223> OTHER INFORMATION: 12B18A LC CDR2

<400> SEQUENCE: 157

Lys Val Ser
1

<210> SEQ ID NO 158
<211> LENGTH: 9
<212> TYPE: PRT
<213> ORGANISM: Artificial Sequence
<220> FEATURE:
<223> OTHER INFORMATION: 12B18A LC CDR3

<400> SEQUENCE: 158

Ser Gln Ser Thr His Val Pro Phe Thr
1               5

<210> SEQ ID NO 159
<211> LENGTH: 11
<212> TYPE: PRT
<213> ORGANISM: Artificial Sequence
<220> FEATURE:
<223> OTHER INFORMATION: 17O12A LC CDR1

<400> SEQUENCE: 159

Gln Ser Leu Val His Ser Asn Gly Asn Thr Tyr
1               5                   10

<210> SEQ ID NO 160
<211> LENGTH: 3
<212> TYPE: PRT
<213> ORGANISM: Artificial Sequence
```

```
<220> FEATURE:
<223> OTHER INFORMATION: 17O12A LC CDR2

<400> SEQUENCE: 160

Arg Val Ser
1

<210> SEQ ID NO 161
<211> LENGTH: 9
<212> TYPE: PRT
<213> ORGANISM: Artificial Sequence
<220> FEATURE:
<223> OTHER INFORMATION: 17O12A LC CDR3

<400> SEQUENCE: 161

Phe Gln Ser Thr His Val Pro His Thr
1               5

<210> SEQ ID NO 162
<211> LENGTH: 11
<212> TYPE: PRT
<213> ORGANISM: Artificial Sequence
<220> FEATURE:
<223> OTHER INFORMATION: 15G23A LC CDR1

<400> SEQUENCE: 162

Gln Ser Leu Val His Ser Asn Gly Asn Thr Tyr
1               5                   10

<210> SEQ ID NO 163
<211> LENGTH: 3
<212> TYPE: PRT
<213> ORGANISM: Artificial Sequence
<220> FEATURE:
<223> OTHER INFORMATION: 15G23A LC CDR2

<400> SEQUENCE: 163

Lys Val Ser
1

<210> SEQ ID NO 164
<211> LENGTH: 10
<212> TYPE: PRT
<213> ORGANISM: Artificial Sequence
<220> FEATURE:
<223> OTHER INFORMATION: 15G23A LC CDR3

<400> SEQUENCE: 164

Ser Gln Ser Thr His Val Pro Pro Leu Thr
1               5                   10

<210> SEQ ID NO 165
<211> LENGTH: 11
<212> TYPE: PRT
<213> ORGANISM: Artificial Sequence
<220> FEATURE:
<223> OTHER INFORMATION: 17N8A LC CDR1

<400> SEQUENCE: 165

Gln Ser Leu Val His Ser Asn Gly Asn Thr Tyr
1               5                   10

<210> SEQ ID NO 166
<211> LENGTH: 3
<212> TYPE: PRT
<213> ORGANISM: Artificial Sequence
```

```
<220> FEATURE:
<223> OTHER INFORMATION: 17N8A LC CDR2

<400> SEQUENCE: 166

Lys Val Ser
1

<210> SEQ ID NO 167
<211> LENGTH: 9
<212> TYPE: PRT
<213> ORGANISM: Artificial Sequence
<220> FEATURE:
<223> OTHER INFORMATION: 17N8A LC CDR3

<400> SEQUENCE: 167

Ser Gln Ser Thr His Val Pro Leu Thr
1               5

<210> SEQ ID NO 168
<211> LENGTH: 11
<212> TYPE: PRT
<213> ORGANISM: Artificial Sequence
<220> FEATURE:
<223> OTHER INFORMATION: 18M19A LC CDR1

<400> SEQUENCE: 168

Gln Ser Leu Val His Ser Asn Gly Asn Thr Tyr
1               5                   10

<210> SEQ ID NO 169
<211> LENGTH: 3
<212> TYPE: PRT
<213> ORGANISM: Artificial Sequence
<220> FEATURE:
<223> OTHER INFORMATION: 18M19A LC CDR2

<400> SEQUENCE: 169

Lys Val Ser
1

<210> SEQ ID NO 170
<211> LENGTH: 9
<212> TYPE: PRT
<213> ORGANISM: Artificial Sequence
<220> FEATURE:
<223> OTHER INFORMATION: 18M19A LC CDR3

<400> SEQUENCE: 170

Ser Gln Ser Thr His Val Pro Trp Thr
1               5

<210> SEQ ID NO 171
<211> LENGTH: 11
<212> TYPE: PRT
<213> ORGANISM: Artificial Sequence
<220> FEATURE:
<223> OTHER INFORMATION: 11F6A LC CDR1

<400> SEQUENCE: 171

Gln Ser Leu Val His Ser Asn Gly Asn Thr Tyr
1               5                   10

<210> SEQ ID NO 172
<211> LENGTH: 3
<212> TYPE: PRT
<213> ORGANISM: Artificial Sequence
```

```
<220> FEATURE:
<223> OTHER INFORMATION: 11F6A LC CDR2

<400> SEQUENCE: 172

Lys Val Ser
1

<210> SEQ ID NO 173
<211> LENGTH: 9
<212> TYPE: PRT
<213> ORGANISM: Artificial Sequence
<220> FEATURE:
<223> OTHER INFORMATION: 11F6A LC CDR3

<400> SEQUENCE: 173

Ser Gln Ser Thr His Val Pro Leu Thr
1               5

<210> SEQ ID NO 174
<211> LENGTH: 7
<212> TYPE: PRT
<213> ORGANISM: Artificial Sequence
<220> FEATURE:
<223> OTHER INFORMATION: 19L14A LC CDR1

<400> SEQUENCE: 174

Ser Ser Val Ser Ser Ser Tyr
1               5

<210> SEQ ID NO 175
<211> LENGTH: 3
<212> TYPE: PRT
<213> ORGANISM: Artificial Sequence
<220> FEATURE:
<223> OTHER INFORMATION: 19L14A LC CDR2

<400> SEQUENCE: 175

Ser Thr Ser
1

<210> SEQ ID NO 176
<211> LENGTH: 9
<212> TYPE: PRT
<213> ORGANISM: Artificial Sequence
<220> FEATURE:
<223> OTHER INFORMATION: 19L14A LC CDR3

<400> SEQUENCE: 176

Gln Gln Tyr Ser Gly Tyr Pro Phe Thr
1               5

<210> SEQ ID NO 177
<211> LENGTH: 8
<212> TYPE: PRT
<213> ORGANISM: Artificial Sequence
<220> FEATURE:
<223> OTHER INFORMATION: HC CDR1
<220> FEATURE:
<221> NAME/KEY: MISC_FEATURE
<222> LOCATION: (6)..(6)
<223> OTHER INFORMATION: Xaa is Asp or Ala

<400> SEQUENCE: 177

Gly Tyr Thr Phe Thr Xaa Tyr Tyr
1               5
```

-continued

```
<210> SEQ ID NO 178
<211> LENGTH: 6
<212> TYPE: PRT
<213> ORGANISM: Artificial Sequence
<220> FEATURE:
<223> OTHER INFORMATION: LC CDR1
<220> FEATURE:
<221> NAME/KEY: MISC_FEATURE
<222> LOCATION: (1)..(1)
<223> OTHER INFORMATION: Xaa is Asp or Glu

<400> SEQUENCE: 178

Xaa Asn Val Gly Thr Tyr
1               5

<210> SEQ ID NO 179
<211> LENGTH: 9
<212> TYPE: PRT
<213> ORGANISM: Artificial Sequence
<220> FEATURE:
<223> OTHER INFORMATION: LC CDR3
<220> FEATURE:
<221> NAME/KEY: MISC_FEATURE
<222> LOCATION: (3)..(3)
<223> OTHER INFORMATION: Xaa is Ser or Thr

<400> SEQUENCE: 179

Gly Gln Xaa Tyr Ser Tyr Pro Leu Thr
1               5

<210> SEQ ID NO 180
<211> LENGTH: 8
<212> TYPE: PRT
<213> ORGANISM: Artificial Sequence
<220> FEATURE:
<223> OTHER INFORMATION: HC CDR1
<220> FEATURE:
<221> NAME/KEY: MISC_FEATURE
<222> LOCATION: (7)..(7)
<223> OTHER INFORMATION: Xaa is Ser or Tyr

<400> SEQUENCE: 180

Gly Tyr Thr Phe Thr Ser Xaa Trp
1               5

<210> SEQ ID NO 181
<211> LENGTH: 8
<212> TYPE: PRT
<213> ORGANISM: Artificial Sequence
<220> FEATURE:
<223> OTHER INFORMATION: HC CDR2
<220> FEATURE:
<221> NAME/KEY: MISC_FEATURE
<222> LOCATION: (8)..(8)
<223> OTHER INFORMATION: Xaa is Thr or Ala

<400> SEQUENCE: 181

Ile Asp Pro Ser Asp Ser Glu Xaa
1               5

<210> SEQ ID NO 182
<211> LENGTH: 13
<212> TYPE: PRT
<213> ORGANISM: Artificial Sequence
<220> FEATURE:
<223> OTHER INFORMATION: HC CDR3
<220> FEATURE:
<221> NAME/KEY: MISC_FEATURE
<222> LOCATION: (1)..(1)
<223> OTHER INFORMATION: Xaa is Ala or Ser
```

```
<220> FEATURE:
<221> NAME/KEY: MISC_FEATURE
<222> LOCATION: (11)..(11)
<223> OTHER INFORMATION: Xaa is Ile or Met

<400> SEQUENCE: 182

Xaa Arg Trp Gly Tyr Tyr Gly Lys Ser Ala Xaa Asp Tyr
1               5                   10

<210> SEQ ID NO 183
<211> LENGTH: 120
<212> TYPE: PRT
<213> ORGANISM: Artificial Sequence
<220> FEATURE:
<223> OTHER INFORMATION: Heavy chain variable region H1

<400> SEQUENCE: 183

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Trp Met His Trp Val Arg Gln Ala Pro Gly Gln Gly Leu Glu Trp Met
            35                  40                  45

Gly Asn Ile Asp Pro Ser Asp Ser Glu Thr His Tyr Asn Gln Lys Phe
        50                  55                  60

Lys Asp Arg Val Thr Leu Thr Val Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ser Arg Trp Gly Tyr Tyr Gly Lys Ser Ala Met Asp Tyr Trp Gly Gln
            100                 105                 110

Gly Thr Leu Val Thr Val Ser Ser
        115                 120

<210> SEQ ID NO 184
<211> LENGTH: 120
<212> TYPE: PRT
<213> ORGANISM: Artificial Sequence
<220> FEATURE:
<223> OTHER INFORMATION: Heavy chain variable region H2

<400> SEQUENCE: 184

Gln Val Gln Leu Val Gln Ser Gly Ala Glu Val Lys Lys Pro Gly Ala
1               5                   10                  15

Ser Val Lys Leu Ser Cys Lys Ala Ser Gly Tyr Thr Phe Thr Ser Tyr
                20                  25                  30

Trp Met His Trp Val Arg Gln Ala Pro Gly Gln Gly Leu Glu Trp Met
            35                  40                  45

Gly Asn Ile Asp Pro Ser Asp Ser Glu Thr His Tyr Asn Gln Lys Phe
        50                  55                  60

Lys Asp Arg Val Thr Leu Thr Val Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ser Arg Trp Gly Tyr Tyr Gly Lys Ser Ala Met Asp Tyr Trp Gly Gln
            100                 105                 110

Gly Thr Leu Val Thr Val Ser Ser
        115                 120
```

-continued

```
<210> SEQ ID NO 185
<211> LENGTH: 120
<212> TYPE: PRT
<213> ORGANISM: Artificial Sequence
<220> FEATURE:
<223> OTHER INFORMATION: Heavy chain variable region H3

<400> SEQUENCE: 185

Gln Val Gln Leu Val Gln Ser Gly Ala Glu Val Lys Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Ile
        35                  40                  45

Gly Asn Ile Asp Pro Ser Asp Ser Glu Thr His Tyr Asn Gln Lys Phe
    50                  55                  60

Lys Asp Arg Ala Thr Leu Thr Val Asp Thr Ser Ser Thr Ala Tyr
65                  70                  75                  80

Met Glu Leu Ser Ser Leu Arg Ser Glu Asp Thr Ala Val Tyr Tyr Cys
                85                  90                  95

Ser Arg Trp Gly Tyr Tyr Gly Lys Ser Ala Met Asp Tyr Trp Gly Gln
            100                 105                 110

Gly Thr Leu Val Thr Val Ser Ser
        115                 120

<210> SEQ ID NO 186
<211> LENGTH: 120
<212> TYPE: PRT
<213> ORGANISM: Artificial Sequence
<220> FEATURE:
<223> OTHER INFORMATION: Heavy chain variable region H4

<400> SEQUENCE: 186

Gln Val Gln Leu Val Gln Ser Gly Ala Glu Val Lys Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Arg Gln Arg Pro Gly Gln Gly Leu Glu Trp Ile
        35                  40                  45

Gly Asn Ile Asp Pro Ser Asp Ser Glu Thr His Tyr Asn Gln Lys Phe
    50                  55                  60

Lys Asp Arg Ala Thr Leu Thr Val Asp Thr Ser Ser Thr Ala Tyr
65                  70                  75                  80

Met Glu Leu Ser Ser Leu Arg Ser Glu Asp Thr Ala Val Tyr Tyr Cys
                85                  90                  95

Ser Arg Trp Gly Tyr Tyr Gly Lys Ser Ala Met Asp Tyr Trp Gly Gln
            100                 105                 110

Gly Thr Leu Val Thr Val Ser Ser
        115                 120

<210> SEQ ID NO 187
<211> LENGTH: 117
<212> TYPE: PRT
<213> ORGANISM: Artificial Sequence
<220> FEATURE:
<223> OTHER INFORMATION: Heavy chain variable region H5
```

-continued

<400> SEQUENCE: 187

```
Gln Ile Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ala Tyr
            20                  25                  30

Tyr Ile Asn Trp Val Arg Gln Ala Pro Gly Gln Arg Leu Glu Trp Ile
        35                  40                  45

Gly Trp Ile Tyr Pro Gly Ser Gly Asn Thr Lys Tyr Asn Glu Lys Phe
    50                  55                  60

Lys Gly Arg Val Thr Leu Thr Val Asp Thr Ser Ala Ser Thr Ala Tyr
65                  70                  75                  80

Ile Glu Leu Ser Ser Leu Arg Ser Glu Asp Thr Ala Val Tyr Tyr Cys
                85                  90                  95

Ala Arg Arg Gly Pro Trp Tyr Phe Asp Val Trp Gly Gln Gly Thr Thr
            100                 105                 110

Val Thr Val Ser Ser
        115
```

<210> SEQ ID NO 188
<211> LENGTH: 117
<212> TYPE: PRT
<213> ORGANISM: Artificial Sequence
<220> FEATURE:
<223> OTHER INFORMATION: Heavy chain variable region H6

<400> SEQUENCE: 188

```
Gln Ile Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ala Tyr
            20                  25                  30

Tyr Ile Asn Trp Val Arg Gln Ala Pro Gly Gln Arg Leu Glu Trp Ile
        35                  40                  45

Gly Trp Ile Tyr Pro Gly Ser Gly Asn Thr Lys Tyr Asn Glu Lys Phe
    50                  55                  60

Lys Gly Arg Val Thr Leu Thr Val Asp Thr Ser Ala Ser Thr Ala Tyr
65                  70                  75                  80

Ile Glu Leu Ser Ser Leu Arg Ser Glu Asp Thr Ala Val Tyr Phe Cys
                85                  90                  95

Ala Arg Arg Gly Pro Trp Tyr Phe Asp Val Trp Gly Gln Gly Thr Thr
            100                 105                 110

Val Thr Val Ser Ser
        115
```

<210> SEQ ID NO 189
<211> LENGTH: 117
<212> TYPE: PRT
<213> ORGANISM: Artificial Sequence
<220> FEATURE:
<223> OTHER INFORMATION: Heavy chain variable region H7

<400> SEQUENCE: 189

```
Gln Ile Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr Ala Tyr
            20                  25                  30

Tyr Ile Asn Trp Val Arg Gln Ala Pro Gly Gln Gly Leu Glu Trp Ile
        35                  40                  45
```

Gly Trp Ile Tyr Pro Gly Ser Gly Asn Thr Lys Tyr Asn Glu Lys Phe
            50                  55                  60

Lys Gly Arg Ala Thr Leu Thr Val Asp Thr Ser Ala Ser Thr Ala Tyr
 65                  70                  75                  80

Ile Glu Leu Ser Ser Leu Arg Ser Glu Asp Thr Ala Val Tyr Phe Cys
                 85                  90                  95

Ala Arg Arg Gly Pro Trp Tyr Phe Asp Val Trp Gly Gln Gly Thr Thr
            100                 105                 110

Val Thr Val Ser Ser
            115

<210> SEQ ID NO 190
<211> LENGTH: 107
<212> TYPE: PRT
<213> ORGANISM: Artificial Sequence
<220> FEATURE:
<223> OTHER INFORMATION: Light chain variable region L1

<400> SEQUENCE: 190

Ala Val Gln Leu Thr Gln Ser Pro Ser Phe Leu Ser Ala Ser Val Gly
 1               5                  10                  15

Asp Arg Val Thr Ile Thr Cys Arg Ala Ser Lys Ser Ile Ser Lys Tyr
                20                  25                  30

Leu Ala Trp Tyr Gln Gln Lys Pro Gly Lys Ala Asn Lys Leu Leu Ile
         35                  40                  45

Tyr Ser Gly Ser Thr Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Met Tyr Tyr Cys Gln Gln His Asn Glu Tyr Pro Trp
                 85                  90                  95

Thr Phe Gly Gly Gly Thr Lys Val Glu Ile Lys
            100                 105

<210> SEQ ID NO 191
<211> LENGTH: 107
<212> TYPE: PRT
<213> ORGANISM: Artificial Sequence
<220> FEATURE:
<223> OTHER INFORMATION: Light chain variable region L2

<400> SEQUENCE: 191

Ala Val Gln Leu Thr Gln Ser Pro Ser Phe Leu Ser Ala Ser Val Gly
 1               5                  10                  15

Gln Arg Ile Thr Ile Asn Cys Arg Ala Ser Lys Ser Ile Ser Lys Tyr
                20                  25                  30

Leu Ala Trp Tyr Gln Gln Lys Pro Gly Lys Ala Asn Lys Leu Leu Ile
         35                  40                  45

Tyr Ser Gly Ser Thr Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Met Tyr Tyr Cys Gln Gln His Asn Glu Tyr Pro Trp
                 85                  90                  95

Thr Phe Gly Gly Gly Thr Lys Val Glu Ile Lys
            100                 105

```
<210> SEQ ID NO 192
<211> LENGTH: 107
<212> TYPE: PRT
<213> ORGANISM: Artificial Sequence
<220> FEATURE:
<223> OTHER INFORMATION: Light chain variable region L3

<400> SEQUENCE: 192

Ala Val Gln Leu Thr Gln Ser Pro Ser Phe Leu Ser Ala Ser Val Gly
1               5                   10                  15

Gln Arg Ile Thr Ile Asn Cys Arg Ala Ser Lys Ser Ile Ser Lys Tyr
            20                  25                  30

Leu Ala Trp Tyr Gln Glu Lys Pro Gly Lys Ala Asn Lys Leu Leu Ile
        35                  40                  45

Tyr Ser Gly Ser Thr Leu Gln Ser Gly Ile Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Met Tyr Tyr Cys Gln Gln His Asn Glu Tyr Pro Trp
                85                  90                  95

Thr Phe Gly Gly Gly Thr Lys Val Glu Ile Lys
            100                 105

<210> SEQ ID NO 193
<211> LENGTH: 107
<212> TYPE: PRT
<213> ORGANISM: Artificial Sequence
<220> FEATURE:
<223> OTHER INFORMATION: Light chain variable region L4

<400> SEQUENCE: 193

Ala Val Gln Ile Thr Gln Ser Pro Ser Phe Leu Ser Ala Ser Val Gly
1               5                   10                  15

Gln Thr Ile Thr Ile Asn Cys Arg Ala Ser Lys Ser Ile Ser Lys Tyr
            20                  25                  30

Leu Ala Trp Tyr Gln Glu Lys Pro Gly Lys Ala Asn Lys Leu Leu Ile
        35                  40                  45

Tyr Ser Gly Ser Thr Leu Gln Ser Gly Ile Pro Ser Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Met Tyr Tyr Cys Gln Gln His Asn Glu Tyr Pro Trp
                85                  90                  95

Thr Phe Gly Gly Gly Thr Lys Val Glu Ile Lys
            100                 105

<210> SEQ ID NO 194
<211> LENGTH: 107
<212> TYPE: PRT
<213> ORGANISM: Artificial Sequence
<220> FEATURE:
<223> OTHER INFORMATION: Light chain variable region L5

<400> SEQUENCE: 194

Glu Ile Val Met Thr Gln Ser Pro Ala Thr Leu Ser Leu Ser Pro Gly
1               5                   10                  15

Glu Arg Ala Thr Leu Ser Cys Arg Ala Ser Glu Asn Val Gly Thr Tyr
            20                  25                  30

Val Ser Trp Tyr Gln Gln Lys Pro Gly Gln Ala Pro Asn Leu Leu Ile
        35                  40                  45
```

```
Tyr Gly Ala Ser Asn Arg Tyr Thr Gly Ile Pro Ala Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Val Tyr His Cys Gly Gln Thr Tyr Ser Tyr Pro Leu
                85                  90                  95

Thr Phe Gly Gln Gly Thr Lys Leu Glu Ile Lys
                100                 105

<210> SEQ ID NO 195
<211> LENGTH: 107
<212> TYPE: PRT
<213> ORGANISM: Artificial Sequence
<220> FEATURE:
<223> OTHER INFORMATION: Light chain variable region L6

<400> SEQUENCE: 195

Glu Ile Val Met Thr Gln Ser Pro Ala Thr Leu Ser Leu Ser Pro Gly
1               5                   10                  15

Glu Arg Ala Thr Leu Ser Cys Arg Ala Ser Glu Asn Val Gly Thr Tyr
                20                  25                  30

Val Ser Trp Tyr Gln Gln Lys Pro Gly Gln Ser Pro Asn Leu Leu Ile
            35                  40                  45

Tyr Gly Ala Ser Asn Arg Tyr Thr Gly Ile Pro Asp Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Val Tyr His Cys Gly Gln Thr Tyr Ser Tyr Pro Leu
                85                  90                  95

Thr Phe Gly Gln Gly Thr Lys Leu Glu Ile Lys
                100                 105

<210> SEQ ID NO 196
<211> LENGTH: 107
<212> TYPE: PRT
<213> ORGANISM: Artificial Sequence
<220> FEATURE:
<223> OTHER INFORMATION: Light chain variable region L7

<400> SEQUENCE: 196

Glu Ile Val Met Thr Gln Ser Pro Ala Thr Leu Ser Leu Ser Pro Gly
1               5                   10                  15

Glu Arg Ala Thr Leu Ser Cys Lys Ala Ser Glu Asn Val Gly Thr Tyr
                20                  25                  30

Val Ser Trp Tyr Gln Gln Lys Pro Gly Gln Ser Pro Asn Leu Leu Ile
            35                  40                  45

Tyr Gly Ala Ser Asn Arg Tyr Thr Gly Ile Pro Asp Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Val Tyr His Cys Gly Gln Thr Tyr Ser Tyr Pro Leu
                85                  90                  95

Thr Phe Gly Gln Gly Thr Lys Leu Glu Ile Lys
                100                 105

<210> SEQ ID NO 197
<211> LENGTH: 107
<212> TYPE: PRT
<213> ORGANISM: Artificial Sequence
```

<220> FEATURE:
<223> OTHER INFORMATION: Light chain variable region L8

<400> SEQUENCE: 197

Asn Ile Val Met Thr Gln Ser Pro Ala Thr Leu Ser Leu Ser Pro Gly
1               5                   10                  15

Glu Arg Ala Thr Leu Ser Cys Lys Ala Ser Glu Asn Val Gly Thr Tyr
            20                  25                  30

Val Ser Trp Tyr Gln Gln Lys Pro Gly Gln Ser Pro Asn Leu Leu Ile
        35                  40                  45

Tyr Gly Ala Ser Asn Arg Tyr Thr Gly Val Pro Asp Arg Phe Ser Gly
    50                  55                  60

Ser Gly Ser Ala Thr Asp Phe Thr Leu Thr Ile Ser Ser Leu Gln Pro
65                  70                  75                  80

Glu Asp Phe Ala Asp Tyr His Cys Gly Gln Thr Tyr Ser Tyr Pro Leu
                85                  90                  95

Thr Phe Gly Gln Gly Thr Lys Leu Glu Ile Lys
            100                 105

<210> SEQ ID NO 198
<211> LENGTH: 107
<212> TYPE: PRT
<213> ORGANISM: Artificial Sequence
<220> FEATURE:
<223> OTHER INFORMATION: Light chain variable region L9

<400> SEQUENCE: 198

Asp Val Gln Leu Thr Gln Ser Pro Ser Phe Leu Ser Ala Ser Val Gly
1               5                   10                  15

Asp Arg Val Thr Ile Thr Cys Arg Ala Ser Lys Ser Ile Ser Lys Tyr
            20                  25                  30

Leu Ala Trp Tyr Gln Gln Lys Pro Gly Lys Ala Asn Lys Leu Leu Ile
        35                  40                  45

Tyr Ser Gly Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Met Tyr Tyr Cys Gln Gln His Asn Glu Tyr Pro Trp
                85                  90                  95

Thr Phe Gly Gly Gly Thr Lys Val Glu Ile Lys
            100                 105

<210> SEQ ID NO 199
<211> LENGTH: 114
<212> TYPE: PRT
<213> ORGANISM: Artificial Sequence
<220> FEATURE:
<223> OTHER INFORMATION: H8 Heavy Chain Variable Region

<400> SEQUENCE: 199

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Ile
        35                  40                  45

Gly Asn Ile Asp Pro Ser Asp Ser Glu Thr His Tyr Ala Gln Lys Phe
    50                  55                  60

Gln Gly Arg Val Thr Leu Thr Val Asp Lys Ser Thr Ser Thr Val Tyr
65                  70                  75                  80

Met Glu Leu Ser Ser Leu Arg Ser Glu Asp Thr Ala Val Tyr Tyr Cys
            85                  90                  95

Ala Gly Thr Asp Leu Ala Tyr Trp Gly Gln Gly Thr Leu Val Thr Val
            100                 105                 110

Ser Ser

<210> SEQ ID NO 200
<211> LENGTH: 107
<212> TYPE: PRT
<213> ORGANISM: Artificial Sequence
<220> FEATURE:
<223> OTHER INFORMATION: L10 Light Chain Variable Region

<400> SEQUENCE: 200

Glu Ile Val Met Thr Gln Ser Pro Gly Thr Leu Ser Leu Ser Pro Gly
1               5                   10                  15

Glu Arg Ala Thr Leu Ser Cys His Ala Ser Gln Asn Ile Asn Val Trp
            20                  25                  30

Leu Ser Trp Tyr Gln Gln Lys Pro Gly Gln Ala Pro Arg Leu Leu Ile
        35                  40                  45

Tyr Lys Ala Ser Asn Leu His Thr Gly Ile Pro Asp Arg Phe Ser Gly
50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Gly Gln Ser Tyr Pro Phe
            85                  90                  95

Thr Phe Gly Gln Gly Thr Lys Val Glu Ile Lys
            100                 105

<210> SEQ ID NO 201
<211> LENGTH: 8
<212> TYPE: PRT
<213> ORGANISM: Artificial Sequence
<220> FEATURE:
<223> OTHER INFORMATION: H8 HC CDR1

<400> SEQUENCE: 201

Gly Tyr Thr Phe Thr Ser Tyr Trp
1               5

<210> SEQ ID NO 202
<211> LENGTH: 8
<212> TYPE: PRT
<213> ORGANISM: Artificial Sequence
<220> FEATURE:
<223> OTHER INFORMATION: H8 HC CDR2

<400> SEQUENCE: 202

Ile Asp Pro Ser Asp Ser Glu Thr
1               5

<210> SEQ ID NO 203
<211> LENGTH: 7
<212> TYPE: PRT
<213> ORGANISM: Artificial Sequence
<220> FEATURE:
<223> OTHER INFORMATION: H8 HC CDR3

```
<400> SEQUENCE: 203

Ala Gly Thr Asp Leu Ala Tyr
1               5

<210> SEQ ID NO 204
<211> LENGTH: 6
<212> TYPE: PRT
<213> ORGANISM: Artificial Sequence
<220> FEATURE:
<223> OTHER INFORMATION: L10 LC CDR1

<400> SEQUENCE: 204

Gln Asn Ile Asn Val Trp
1               5

<210> SEQ ID NO 205
<211> LENGTH: 3
<212> TYPE: PRT
<213> ORGANISM: Artificial Sequence
<220> FEATURE:
<223> OTHER INFORMATION: L10 LC CDR2

<400> SEQUENCE: 205

Lys Ala Ser
1

<210> SEQ ID NO 206
<211> LENGTH: 9
<212> TYPE: PRT
<213> ORGANISM: Artificial Sequence
<220> FEATURE:
<223> OTHER INFORMATION: L10 LC CDR3

<400> SEQUENCE: 206

Gln Gln Gly Gln Ser Tyr Pro Phe Thr
1               5

<210> SEQ ID NO 207
<211> LENGTH: 323
<212> TYPE: PRT
<213> ORGANISM: Homo sapiens

<400> SEQUENCE: 207

Met Trp Pro Leu Val Ala Ala Leu Leu Leu Gly Ser Ala Cys Cys Gly
1               5                   10                  15

Ser Ala Gln Leu Leu Phe Asn Lys Thr Lys Ser Val Glu Phe Thr Phe
            20                  25                  30

Cys Asn Asp Thr Val Val Ile Pro Cys Phe Val Thr Asn Met Glu Ala
        35                  40                  45

Gln Asn Thr Thr Glu Val Tyr Val Lys Trp Lys Phe Lys Gly Arg Asp
    50                  55                  60

Ile Tyr Thr Phe Asp Gly Ala Leu Asn Lys Ser Thr Val Pro Thr Asp
65                  70                  75                  80

Phe Ser Ser Ala Lys Ile Glu Val Ser Gln Leu Leu Lys Gly Asp Ala
                85                  90                  95

Ser Leu Lys Met Asp Lys Ser Asp Ala Val Ser His Thr Gly Asn Tyr
            100                 105                 110

Thr Cys Glu Val Thr Glu Leu Thr Arg Glu Gly Glu Thr Ile Ile Glu
        115                 120                 125

Leu Lys Tyr Arg Val Val Ser Trp Phe Ser Pro Asn Glu Asn Ile Leu
    130                 135                 140
```

```
Ile Val Ile Phe Pro Ile Phe Ala Ile Leu Leu Phe Trp Gly Gln Phe
145                 150                 155                 160

Gly Ile Lys Thr Leu Lys Tyr Arg Ser Gly Gly Met Asp Glu Lys Thr
                165                 170                 175

Ile Ala Leu Leu Val Ala Gly Leu Val Ile Thr Val Ile Val Ile Val
                180                 185                 190

Gly Ala Ile Leu Phe Val Pro Gly Glu Tyr Ser Leu Lys Asn Ala Thr
            195                 200                 205

Gly Leu Gly Leu Ile Val Thr Ser Thr Gly Ile Leu Ile Leu Leu His
        210                 215                 220

Tyr Tyr Val Phe Ser Thr Ala Ile Gly Leu Thr Ser Phe Val Ile Ala
225                 230                 235                 240

Ile Leu Val Ile Gln Val Ile Ala Tyr Ile Leu Ala Val Val Gly Leu
                245                 250                 255

Ser Leu Cys Ile Ala Ala Cys Ile Pro Met His Gly Pro Leu Leu Ile
                260                 265                 270

Ser Gly Leu Ser Ile Leu Ala Leu Ala Gln Leu Leu Gly Leu Val Tyr
            275                 280                 285

Met Lys Phe Val Ala Ser Asn Gln Lys Thr Ile Gln Pro Pro Arg Lys
        290                 295                 300

Ala Val Glu Glu Pro Leu Asn Ala Phe Lys Glu Ser Lys Gly Met Met
305                 310                 315                 320

Asn Asp Glu
```